United States Patent
Milosevic et al.

(10) Patent No.: US 11,155,589 B2
(45) Date of Patent: Oct. 26, 2021

(54) GENERATION OF ANTIGEN-SPECIFIC TCRS

(71) Applicants: MEDIGENE IMMUNOTHERAPIES GMBH, Planegg-Martinsried (DE); HELMHOLTZ ZENTRUM MÜNCHEN DEUTSCHES FORSCHUNGSZENTRUM FÜR GESUNDHEIT UND UMWELT (GMBH), Neuherberg (DE)

(72) Inventors: Slavoljub Milosevic, Munich (DE); Christian Ellinger, Munich (DE); Carina Wehner, Munich (DE); Dolores Schendel, Munich (DE)

(73) Assignees: Medigene Immunotherapies GmbH, Planegg-Martinsried (DE); Helmholtz Zentrum München Deutsches Forschungszentrum für Gesundheit und Umwelt (GmbH), Neuherberg (DE)

( * ) Notice: Subject to any disclaimer, the term of this patent is extended or adjusted under 35 U.S.C. 154(b) by 79 days.

(21) Appl. No.: 16/065,024

(22) PCT Filed: Dec. 22, 2016

(86) PCT No.: PCT/EP2016/082443
§ 371 (c)(1),
(2) Date: Jun. 21, 2018

(87) PCT Pub. No.: WO2017/109109
PCT Pub. Date: Jun. 29, 2017

(65) Prior Publication Data
US 2019/0002515 A1 Jan. 3, 2019

(30) Foreign Application Priority Data

Dec. 23, 2015 (EP) .................................. 15202329
Sep. 23, 2016 (EP) .................................. 16190399

(51) Int. Cl.

| | |
|---|---|
| C07K 14/47 | (2006.01) |
| A61K 35/17 | (2015.01) |
| A61P 35/00 | (2006.01) |
| C12N 5/0784 | (2010.01) |
| A61K 38/00 | (2006.01) |
| C12N 5/0783 | (2010.01) |
| A61K 39/00 | (2006.01) |

(52) U.S. Cl.
CPC .......... *C07K 14/4748* (2013.01); *A61K 35/17* (2013.01); *A61K 38/00* (2013.01); *A61K 39/001191* (2018.08); *A61P 35/00* (2018.01); *C12N 5/0638* (2013.01); *C12N 5/0639* (2013.01); *A61K 39/001184* (2018.08); *A61K 2039/5154* (2013.01); *C07K 2319/02* (2013.01); *C07K 2319/03* (2013.01); *C07K 2319/06* (2013.01); *C12N 2501/22* (2013.01); *C12N 2501/2304* (2013.01); *C12N 2501/24* (2013.01); *C12N 2502/1114* (2013.01); *C12N 2506/115* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 4,703,004 | A | 10/1987 | Hopp et al. |
| 4,851,341 | A | 7/1989 | Hopp et al. |
| 5,591,828 | A | 1/1997 | Bosslet et al. |
| 5,766,886 | A | 6/1998 | Studnicka et al. |
| 6,372,716 | B1 | 4/2002 | Bush et al. |
| 6,566,329 | B1 | 5/2003 | Meyn et al. |
| 6,685,940 | B2 | 2/2004 | Andya et al. |
| 10,882,891 | B2 | 1/2021 | Milosevic et al. |
| 2002/0045241 | A1 | 4/2002 | Schendel |
| 2005/0037421 | A1 | 2/2005 | Honda et al. |
| 2005/0042718 | A1 | 2/2005 | Bazin et al. |
| 2005/0112141 | A1 | 5/2005 | Terman |
| 2005/0136049 | A1 | 6/2005 | Ledbetter et al. |
| 2018/0245242 | A1 | 8/2018 | Schendel |
| 2018/0256716 | A1 | 8/2018 | Schendel |

FOREIGN PATENT DOCUMENTS

| | | |
|---|---|---|
| DE | 19625191 A1 | 1/1998 |
| EP | 0404097 A2 | 12/1990 |
| EP | 0451216 A1 | 10/1991 |
| EP | 1910521 A1 | 4/2008 |

(Continued)

OTHER PUBLICATIONS

Kavanagh (Blood, 107: 1963-1969, 2006 (Year: 2006).*

(Continued)

*Primary Examiner* — Robert M Kelly

(74) *Attorney, Agent, or Firm* — Clark & Elbing LLP

(57) ABSTRACT

The present invention contemplates methods for the generation of human antigen-specific T lymphocytes. The methods employ MHC class-II targeting signals fused to an antigen or fragment thereof to obtain MHC class presentation of RNA coded proteins. Accordingly, the present invention concerns expression vectors comprising MHC class-II targeting signal and at least one antigen or fragment thereof and its use for the in vitro generation of antigen-specific T lymphocytes. T cell clones and T cell receptors (TCRs) specific for tumor antigens or viral antigens are also described.

20 Claims, 12 Drawing Sheets

Figure 1:
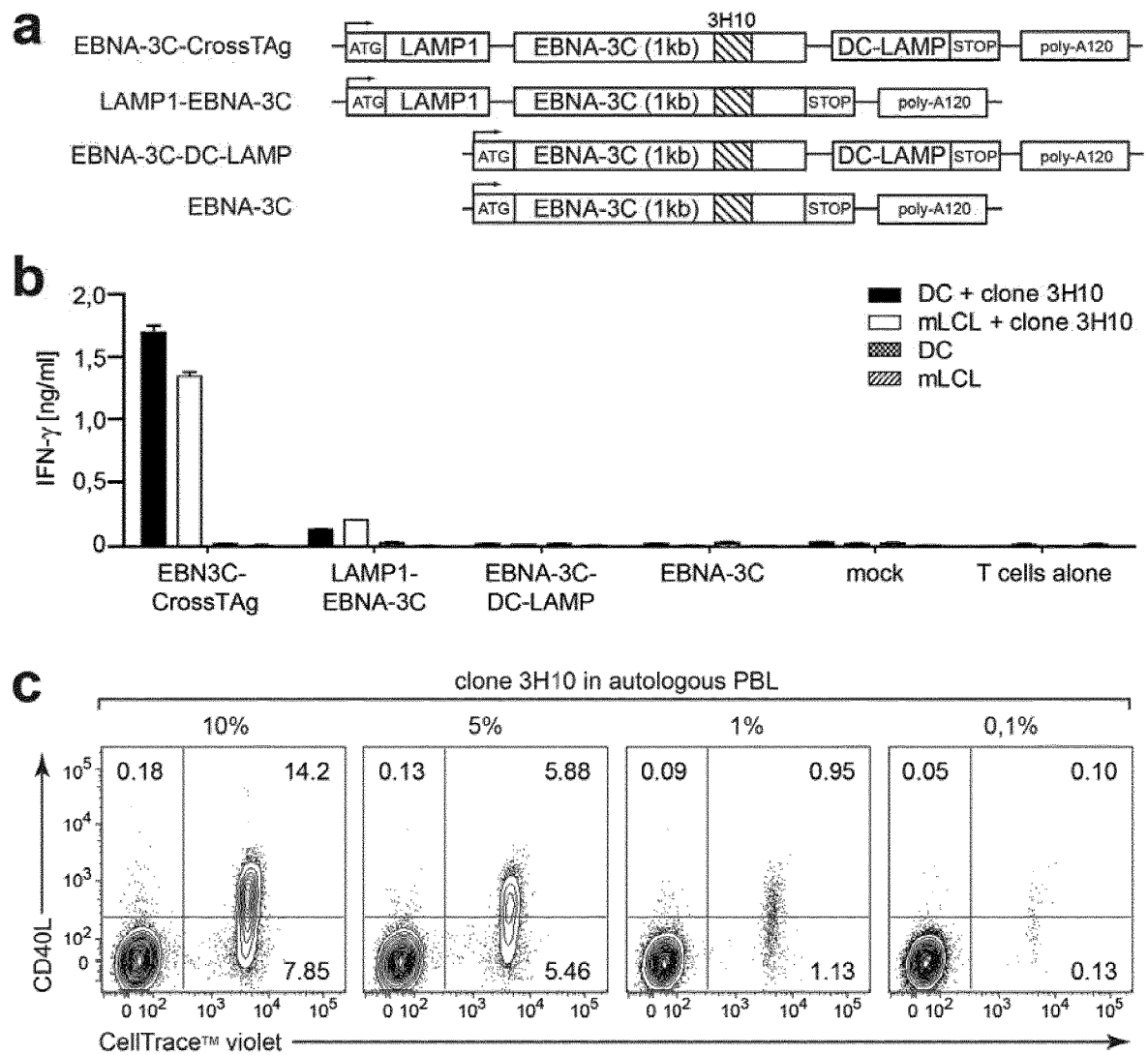

Specification includes a Sequence Listing.

(56) References Cited

FOREIGN PATENT DOCUMENTS

| | | | |
|---|---|---|---|
| EP | 2700708 A2 * | 2/2014 | ........... C12N 5/0639 |
| JP | H05-504621 | 7/1993 | |
| JP | H06502529 | 3/1994 | |
| JP | H06-506362 | 7/1994 | |
| JP | H07-502165 | 3/1995 | |
| JP | H08-502246 | 3/1996 | |
| JP | 2007097580 A | 4/2007 | |
| JP | 2004535168 A | 11/2014 | |
| WO | WO-9107508 | 5/1991 | |
| WO | WO-9202629 | 2/1992 | |
| WO | WO-9209305 A1 | 6/1992 | |
| WO | WO-9305813 | 4/1993 | |
| WO | WO-9311161 A1 | 6/1993 | |
| WO | WO 9311794 | 6/1993 | |
| WO | WO-9404686 A1 | 3/1994 | |
| WO | WO-9405801 | 3/1994 | |
| WO | WO-9405801 A1 | 3/1994 | |
| WO | WO-0155366 A1 | 8/2001 | |
| WO | WO-0162908 A2 | 8/2001 | |
| WO | WO-0192291 A2 | 12/2001 | |
| WO | WO-2004044004 A2 | 5/2004 | |
| WO | WO-2005116074 A2 | 12/2005 | |
| WO | WO-2005116646 A1 | 12/2005 | |
| WO | WO-2007131092 A2 | 11/2007 | |
| WO | WO-2011107409 A1 | 9/2011 | |
| WO | WO 2013/187906 A1 | 12/2013 | |
| WO | WO-2014089335 A2 | 6/2014 | |
| WO | WO-2015136072 A1 | 9/2015 | |
| WO | WO 2016/057986 A1 | 4/2016 | |
| WO | WO-2016193299 A1 | 12/2016 | |
| WO | WO-2016193300 A1 | 12/2016 | |
| WO | WO-2016193301 A1 | 12/2016 | |
| WO | WO-2017109109 A1 | 6/2017 | |
| WO | WO-2017109110 A1 | 6/2017 | |

OTHER PUBLICATIONS

Burdek (Journal of Translational Medicine, 8(90): 1-13, 2010 (Year: 2010).*
Spranger (J Immunol 2010; 185:738-747, 2010 (Year: 2010).*
Wehner (Journal for Immunotherapy of Cancer, 1(Suppl 1(: P239, 2013, abstract, (Year: 2013).*
Wehner (Thesis, 1-177, Jul. 2013 (Year: 2013).*
Bonehill, (The American Society of Gene Therapy, pp. 1-11, 2008) (Year: 2008).*
Allard (Vaccine, 26: 3735-3741, 2008), (Year: 2008).*
Boullart, A.C.I. et al., "Maturation of monocyte-derived dendritic cells with Toll-like receptor 3 and 7/8 ligands combined with prostaglandin E2 results in high interleukin-12 production and cell migration," *Cancer Immunol Immunother* 57:1589-97, Springer Publishing Group, United States (2008).
Wehner, C. et al., "Isolation of antigen-specific CD8+ T lymphocytes in vitro and in vivo," *J Immother Cancer* 1(suppl):P239, BioMed Central, England (2013).
Zerial, M. et al., "The transmembrane segment of the human transferrin receptor functions as a signal peptide," *The EMBO Journal* 5: 1543-1550, IRL Press, England (1986).
Wehner, Carina: "Induktion Tumorantigen-spezifischer CD8 + T-Lymphozyten in vitro und in vivo-Dissertation", Jul. 1, 2013 (Jul. 1, 2013). XP55358705, Retrieved from the Internet: URL:https://edoc.ub.uni-muenchen.de/20384/1/Wehner_Carina.pdf [retrieved on Mar. 24, 2017], 177 pages.
GenBank, "*Homo sapiens* MAGE family member A4 (MAGEA4), transcript variant 4, mRNA," Accession No. NM_001011550.1, accessed at https://www.ncbi.nlm.nih.gov/nuccore/NM_001011550, accessed on Jun. 23, 2018.
GenBank, "*Homo sapiens* mRNA for NY-ESO-1 protein," Accession No. AJ003149.1, accessed at https://www.ncbi.nlm.nih.gov/nuccore/AJ003149, accessed on Oct. 7, 2008.
GenBank, "*Homo sapiens* SSX4 (SSX4) mRNA, complete cds," Accession No. U90841.1, accessed at https://www.ncbi.nlm.nih.gov/nuccore/U90841, accessed on Mar. 18, 1998.
GenBank, "*Homo sapiens* XAGE-1 mRNA, complete cds," Accession No. AF251237.1, accessed at https://www.ncbi.nlm.nih.gov/nuccore/AF251237, accessed on Aug. 23, 2000.
International Preliminary Report on Patentability for Application No. PCT/EP2016/082445, dated Jun. 26, 2018, 8 pages.
International Search Report and Written Opinion for Application No. PCT/EP2016/082445, dated Apr. 12, 2017, 13 pages.
Mortenson, E.D., et al., "Effective Anti-neu-initiated Antitumor Responses Require the Complex Role of CD4+ T Cells,"Clinical Cancer Research, 19(6):1476-1486, The Association, United States (Mar. 2013).
Shultz, L.D., et al., "Humanized Mice In Translational Biomedical Research," Nature Reviews Immunology, 7(2):118-130, Nature Publishing Group, England (Feb. 2007).
Spranger, S., et al., "Generation of Th1-Polarizing Dendritic Cells Using the TLR7/8 Agonist CL075,"Journal of Immunology, 185(1):738-747, American Association of Immunologists, United States (Jul. 2010).
Spranger, S., et al., "NOD/Scid Il-2rg(Null) Mice: a Preclinical Model System to Evaluate Human Dendritic Cell-based Vaccine Strategies in Vivo,"Journal of Translational Medicine, 10:30, BioMed Central, England (Feb. 2012).
Rosenberg, S.A., et al., "Cancer Immunotherapy: Moving Beyond Current Vaccines," Nature Medicine 10(9):909-915, Nature Publishing Company, United States (2004).
Ellinger, Christian: "Gezielte MHC-Klasse-II—Kreuzprasentation fur die Generierung und Isolierung Tumor/Testis-Antigen-spezifischer CD4 + T-Lymphozyten—Dissertation," Jul. 16, 2013 (Jul. 16, 2013). XP55358711, Retrieved from the Internet: URL:https://edoc.ub.uni-muenchen.de/19870/1/Ellinger Christian.pdf, [retrieved-on Mar. 24, 2017], 155 pages.
Abraham, R.T. and Weiss, A., "Jurkat T Cells and Development of the T-cell Receptor Signalling Paradigm," Nature Reviews. Immunology 4(4):301-308, Nature Pub. Group, England (Apr. 2004).
Ahlgren, K.M., et al., "T Cell Receptor—Vbeta Repertoires in Lung and Blood CD4+ and CD8+ T Cells of Pulmonary Sarcoidosis Patients," BMC Pulmonary Medicine 14(1):50, BioMed Central, England (Mar. 2014).
Altschul, S.F., et al., "Basic Local Alignment Search Tool," Journal of Molecular Biology 215(3):403-410, Elsevier, England (Oct. 1990).
Arbabi Ghahroudi, M., et al., "Selection and Identification of Single Domain Antibody Fragments from Camel Heavy-chain Antibodies," FEBS Letters 414(3):521-526, John Wiley & Sons Ltd., England (Sep. 1997).
Balow, J.P. and Kerase, K.P., "Isolation of Newly Expressed Surface T Cell Antigen Receptor Complexes by Serial Precipitation with Anti-TCR Antibodies and Immobilized Streptavidin," Journal of Immunological Methods 189(2):251-258, Elsevier, Netherlands (Feb. 1996).
Bernett, M.J., et al., "Engineering Fully Human Monoclonal Antibodies from Murine Variable Regions," Journal of Molecular Biology 396(5):1474-1490, Elsevier, England (Mar. 2010).
Bird, R.E., et al., "Single-chain Antigen-binding Proteins," Science 242(4877):423-426, Association for the Advancement of Science, United States (Oct. 1988).
Bonehill A. et al., "Messenger RNA-electroporated dendritic cells presenting MAGE-A3 simultaneously in HLA class I and class II molecules," J Immunol 172(11):6649-6657, The American Association of Immunologists, United States (2004).
Brennan, M., et al., "Preparation of Bispecific Antibodies by Chemical Recombination of Monoclonal Immunoglobulin G1 Fragments," Science 229(4708):81-83, American Association for the Advancement of Science, United States (Jul. 1985).
Brewer, J.L. and Ericson, S.G., "An Improved Methodology to Detect Human T Cell Receptor beta Variable Family Gene Expression Patterns," Journal of Immunological Methods 302(1-2):54-67, Elsevier, Netherlands (Jul. 2005).
Busch, D.H., et al., "Evolution of a Complex T Cell Receptor Repertoire During Primary and Recall Bacterial Infection," The

(56) References Cited

OTHER PUBLICATIONS

Journal of Experimental Medicine 188(1):61-70, Rockefeller University Press, United States (Jul. 1998).
BV/Hu_TRBVMab.html, last accessed Jul. 9, 2018, 3 pages (2003).
Byers, V.S. and Baldwin, R.W., "Rationale for Clinical Use of Immunotoxins in Cancer and Autoimmune Disease," Seminars in Cell Biology 2(1):59-70, Academic Press, England (Feb. 1991).
Call, M.E. and Wucherpfennig, K.W., "The T Cell Receptor: Critical Role of the Membrane Environment in Receptor Assembly and Function," Annual Review of Immunology 23:101-125, Annual Reviews Inc., United States (2005).
Chiocchia, G., et al., "Therapy against murine collagen-induced arthritis with T cell receptor $V_\beta$-specific antibodies*," Eur. J. Immunol. 21:2899-2905, Wiley-VCH, Germany (1991).
Chu, T.H. et al., "Highly Efficient Eukaryotic Gene Expression vectors For Peptide Secretion," Biotechniques Pept Res 8:101-7, Future Science Group, England, (1995).
Cohen, C.J., et al., "Enhanced Antitumor Activity of T Cells Engineered to Express T-cell Receptors with a Second Disulfide Bond," Cancer Research 67(8):3898-3903, American Association for Cancer Research, United States (Apr. 2007).
Cohen, C.J., et al., "Enhanced Antitumor Activity of Murine-human Hybrid T-cell Receptor (TCR) in Human Lymphocytes is Associated with Improved Pairing and TCR/CD3 Stability," Cancer Research 66(17):8878-8886, American Association for Cancer Research, United States (Sep. 2006).
Conrath, K.E., et al., "Beta-lactamase Inhibitors Derived From Single-domain Antibody Fragments Elicited in the Camelidae," Antimicrobial Agents and Chemotherapy 45(10):2807-2812, American Society for Microbiology, United States (Oct. 2001).
Coren, L., et al., "Production of Retroviral constructs for effective transfer and expression of T-cell receptor genes using Golden Gate Cloning," Biotechniques 58(3):135-139, Future Medicine, United States (Mar. 2015).
Cortez-Retamozo, V., et al. , "Efficient Cancer Therapy with a Nanobody-based Conjugate," Cancer Research 64(8):2853-2857, American Association for Cancer Research, United States (Apr. 2004).
De Alboran, I.M., et al., "Attenuation of autoimmune disease and lymphocyte accumulation in MRL//pr mice by treatment with anti-$V_\beta$ antibodies*," Eur. J. Immunol. 22:2153-2158, Wiley-VCH, Germany ( Apr. 1992).
Delobel, A., et al., "Therapeutic Antibody Glycosylation Analysis: a Contract Research Organization Perspective in the Frame of Batch Release or Comparability Support," Methods in Molecular Biology 988:115-143, Humana Press, United States (2013).
Desmet, J., et al., Chapter 22—"Humanization by Resurfacing," in Antibody Engineering, vol. 1, second edition, Kontermann, R, and Dubel, S., eds., pp. 341-342, Springer-Verlag Berlin Heidelberg, Germany (2010).
Desmyter, A., et al., "Antigen Specificity and High Affinity Binding Provided by One Single Loop of a Camel Single-domain Antibody," The Journal of Biological Chemistry 276(28):26285-26290, American Society for Biochemistry and Molecular Biology, United States (Jul. 2001).
Diener, E., et al., "Specific Immunosuppression by Immunotoxins Containing Daunomycin," Science 231(4734):148-150, American Association for the Advancement of Science, United States (Jan. 1986).
Dreyer, A.M., et al., "An efficient system to generate monoclonal antibodies against membrane-associated proteins by immunization with antigen-expressing mammalian cells," BMC Technology 10:87, Bio Med Central, England (2010).
Fanger, M.W., et al., "Bispecific Antibodies and Targeted Cellular Cytotoxicity," Immunology Today 12(2):51-54, Elsevier Science Publishers, England (Feb. 1991).
Fanger, M.W., et al., "Bispecific Antibodies," Critical Reviews in Immunology 12(3-4):101-24, Begell House, United States (1992).

Fanger, M.W., et al., "Use of Bispecific Antibodies in the Therapy of Tumors," in Immunoconjugate Therapy of Hematologic Malignancies, Chapter 10, Rosen, S., ed., pp. 181-194, Springer US, United States (1993).
Folch, G. and Lefranc, M.P., "The Human T Cell Receptor Beta Variable (TRBV) Genes," Experimental and Clinical Immunogenetics 17(1):42-54, Karger, Switzerland (2000).
Greenberg, A.S., et al., "A New Antigen Receptor Gene Family that Undergoes Rearrangement and Extensive Somatic Diversification in Sharks," Nature 374(6518):168-173, Nature Publishing Group, England (Mar. 1995).
Gruber, M., et al., "Efficient Tumor Cell Lysis Mediated by a Bispecific Single Chain Antibody Expressed in *Escherichia Coli*," The Journal of Immunology 152(11):5368-5374, The American Association of Immunologists, Inc., United States (1994).
Hamers-Casterman, C., et al., "Naturally Occurring Antibodies Devoid of Light Chains," Nature 363(6428):446-448, Nature Publishing Group, England (Jun. 1993).
Harlow, et al. (Eds), Antibodies A Laboratory Manual, Cold Spring Harbor Laboratory, Chapter 6, NY (1988).
Higgins, P.J., et al., "In Vitro Inhibition of a Variety of Human Immunodeficiency Virus Isolates by a Broadly Reactive, V3-directed Heteroconjugate Antibody In Vitro Inhibition of a Variety of Human Immunodeficiency Virus Isolates by a Broadly Reactive, V3-directed Heteroconjugate Antibody," The Journal of Infectious Diseases 166(1):198-202, Oxford University Press, United States (Jul. 1992).
Hildinger, M., et al., "Design of 5' Untranslated Sequences in Retroviral Vectors Developed for Medical Use," Journal of Virology 73(5):4083-4089, American Society for Microbiology, United States (May 1999).
Hirsch, T., et al., "Effects of In Vivo Administration of anti-T3 Monoclonal Antibody on T cell Function in Mice—I. Immunosuppression of transplantation responses," Journal of Immunology 140(11): 3766-3772, American Association of Immunologists, United States (1988).
Holliger, P., et al., "Diabodies: Small Bivalent and Bispecific Antibody Fragments," Proceedings of the National Academy of Sciences USA 90(14):6444-6448, National Academy of Sciences, United States (Jul. 1993).
Huston, J.S., et al., "Protein Engineering of Antibody Binding Sites: Recovery of Specific Activity in an Anti-digoxin Single-chain Fv Analogue Produced in *Escherichia Coli*," Proceedings of the National Academy of Sciences USA 85(16):5879-5883, National Academy of Sciences, United States (Aug. 1988).
IMGT Repertoire (IG and TR) IGMT Web Resources, "Reagents monoclonal antibodies: anti-mouse TRAV," accessed at http://www.imgt.org/IMGTrepertoire/index.php?section=Regulation&repertoire=antibodies&species=mouse&group=TRAV.
IMGT Repertoire (IG and TR), "Reagents monoclonal antibodies: anti-mouse TRBV," accessed at http://www.imgt.org/IMGTrepertoire/index.php?section=Regulation&repert.
IMGT Repertoire (IG and TR), IGMT Web Resources, "Reagents Monoclonal antibodies: anti-human TRBV," accessed at http://www.imgt.org/IMGTrepertoire/Regulation/antibodies/human/TRB/TR.
International Search Report and Written Opinion for International Application No. PCT/EP2016/062366, European Patent Office, Rijswijk, dated Aug. 31, 2016, 17 pages.
International Search Report and Written Opinion for International Application No. PCT/EP2016/062367, European Patent Office, Rijswijk, dated Aug. 2, 2016, 14 pages.
International Search Report and Written Opinion for International Application No. PCT/EP2016/062370, European Patent Office, Rijswijk, dated Jul. 8, 2016, 12 pages.
IOTest Beta Mark, "25 T-Cell Repertoire assays," IOTest® Beta Mark PN IM3497 TCR Vβ Repertoire Kit, accessed at https://www.bccytometry.com/PDF/DataSheet/IM3497DS.pdf, last accessed Jun. 20, 2007, 20 pages.
Irving, R.A., et al., "Ribosome Display and Affinity Maturation: From Antibodies to Single V-domains and Steps Towards Cancer Therapeutics," Journal of Immunological Methods 248(1-2):31-45, Elsevier Science Publishers, Netherlands (Feb. 2001).

(56) References Cited

OTHER PUBLICATIONS

Karlin, S. and Altschul, S.F., "Applications and Statistics for Multiple High-Scoring Segments in Molecular Sequences," Proceedings of the National Academy of Sciences of the United States of America 90(12):5873-5877, National Academy of Sciences, United States (Jun. 1993).
Kessels, H.W.H.G., et al., "Changing T Cell Specificity by Retroviral T Cell Receptor Display," Proceedings of the National Academy of Sciences of the United States of America 97(26):14578-14583, National Academy of Sciences, United States (Dec. 2000).
Kipriyanov, S.M., et al., "Recombinant Single-chain Fv Fragments Carrying C-terminal Cysteine Residues: Production of Bivalent and Biotinylated Miniantibodies," Molecular Immunology 31(14):1047-1058, Pergamon Press, England (1994).
Kipriyanov, S.M., et al., "Single-chain Antibody Streptavidin Fusions: Tetrameric Bifunctional Scfv-complexes With Biotin Binding Activity and Enhanced Affinity to Antigen," Human Antibodies and Hybridomas 6(3):93-101, Butterworth-Heinemann, United States (1995).
Kohler, G. and Milstein, C., "Continuous Cultures of Fused Cells Secreting Antibody of Predefined Specificity," Nature 256(5517):495-497, Macmillan Journals Ltd., England (Aug. 1975).
Kontermann, "Dual targeting strategies with bispecific antibodies," mAbs 4(2):182-197, Taylor & Francis, England (2012).
Lee, N.E. and Davis, M.M., "T Cell Receptor beta-chain Genes in BW5147 and Other AKR Tumors. Deletion Order of Murine V beta Gene Segments and Possible 5' Regulatory Regions," Journal of Immunology 140(5):1665-1675, American Association of Immunologists, United States (Mar. 1988).
Lefranc, M.P., et al., "IMGT Unique Numbering for Immunoglobulin and T Cell Receptor Variable Domains and Ig Superfamily V-like Domains," Developmental and Comparative Immunology 27(1):55-77, Elsevier Science, United States (Jan. 2003).
Lefranc, M.P., et al., "IMGT, the International ImMunoGeneTics Information System," Nucleic Acids Research 33:D593-D597, Oxford University Press, England (Jan. 2005).
Letourneur, F. and Malissen, B., "Derivation of a T Cell Hybridoma Variant Deprived of Functional T Cell Receptor alpha and beta Chain Transcripts Reveals a Nonfunctional alpha-mRNA of BW5147 Origin," European Journal of Immunology 19(12):2269-2274, Wiley-VCH, Germany (Dec. 1989).
Lu, J., et al., "Analysis of T-cell Repertoire in Hepatitis-associated Aplastic Anemia," Blood 103(12):4588-4593, American Society of Hematology, United States (Jun. 2004).
Maeda, T., et al., "Amelioration of Acute Graft-Versus-Host Disease and Re-Establishment of Tolerance by Short-Term Treatment With an Anti-TCR Antibody," Journal of Immunology 153(9):4311-4320, American Association of Immunologists, United States (Nov. 1994).
Mamedov, I.Z., et al., "Preparing Unbiased T-Cell Receptor and Antibody cDNA Libraries for the Deep Next Generation Sequencing Profiling," Frontiers in Immunology 4:456, Frontiers Research Foundation, Switzerland (2013).
Milstein, C. and Cuello, A.C., "Hybrid Hybridomas and their Use in Immunohistochemistry," Nature 305(5934):537-540, Nature Publishing Group, England (Oct. 1983).
Muyldermans, S. and Lauwereys, M., "Unique Single-Domain Antigen Binding Fragments Derived From Naturally Occurring Camel Heavy-Chain Antibodies," Journal of Molecular Recognition 12(2):131-140, John Wiley & Sons, England (Mar.-Apr. 1999).
Muyldermans, S., "Single Domain Camel Antibodies: Current Status," Reviews in Molecular Biotechnology 74(4):277-302, Elsevier Science Publishers, Netherlands (2001).
Nguyen, V.K., et al., "Functional Heavy-Chain Antibodies in Camelidae," Advances in Immunology 79:261-296, Academic Press, United States (2001).
Nguyen, V.K., et al., "Heavy-Chain Antibodies in Camelidae; a Case of Evolutionary Innovation," Immunogenetics 54(1):39-47, Springer Verlag, United States (Apr. 2002).
Nguyen, V.K., et al., "Loss of Splice Consensus Signal Is Responsible for the Removal of the Entire C(H)1 Domain of the Functional Camel IGG2A Heavy-Chain Antibodies," Molecular Immunology 36(8):515-524, Pergamon Press, England (Jun. 1999).
Nguyen, V.K., et al., "The Specific Variable Domain of Camel Heavy-chain Antibodies Is Encoded in the Germline," Journal of Molecular Biology 275(3):413-418, Elsevier, England (Jan. 1998).
Nuttall, S.D., et al., "Isolation of the New Antigen Receptor From Wobbegong Sharks, and Use as a Scaffold for the Display of Protein Loop Libraries," Molecular Immunology 38(4):313-326, Pergamon Press, England (Aug. 2001).
Office Action for Japanese Application No. JP2017-563246, dated Dec. 11, 2018, The Japan Patent Office, Tokyo, Japan, 6 pages.
Office Action for Japanese Application No. JP2017-563247, dated Dec. 11, 2018, The Japan Patent Office, Tokyo, Japan, 6 pages.
Office Action for New Zealand Patent IP No. 737400, dated Sep. 3, 2018, New Zealand Intellectual Property Office, New Zealand, 7 pages.
Office Action for New Zealand Patent IP No. 737423, dated Aug. 2, 2018, New Zealand Intellectual Property Office, New Zealand, 6 pages.
Office Action for New Zealand Patent IP No. 737851, dated Aug. 16, 2018, New Zealand Intellectual Property Office, New Zealand, 6 pages.
IMGT Repertoire (IG and TR), "Reagents monoclonal antibodies: anti-mouse TRBV," accessed at http://www.imgt.org/IMGTrepertoire/index.php?section=Regulation&repertoire=antibodies&species=mouse&group=TRBV, last accessed Jul. 9, 2018, 2 pages (2011).
Olsson, T., et al., "Depletion of Vβ5.2/5.3 T cells with a humanized antibody in patients with multiple sclerosis," European Journal of Neurology 9:153-164, Wiley Blackwell, United States (2002).
Penaranda, C., et al., "Anti-CD3 Therapy Promotes Tolerance by Selectively Depleting Pathogenic Cells While Preserving Regulatory T cells," Journal of Immunology 187(4):2015-2022, The American Association of Immunologists, United States (2011).
Pilch, H., et al., "Improved Assessment of T-cell Receptor (TCR) VB Repertoire in Clinical Specimens: Combination of TCR-CDR3 Spectratyping With Flow Cytometry-based TCR VB Frequency Analysis," Clinical and Diagnostic Laboratory Immunology 9(2):257-266, American Society for Microbiology, United States (Mar. 2002).
Poljak, R.J., "Production and Structure of Diabodies," Structure 2(12):1121-1123, Cell Press, United States (1994).
RecName: Full=Lysosome-associated membrane glycoprotein 3; (LAMP-3),UniprotAC:Q9UQV4 (LAMP3_HUMAN), Nov. 11, 2015, <URL: https://www.uniprot.org/uniprot/09UQV4.txt?version=101>.
RecName: Full=Lysosome-associated membrane glycoprotein 1, Uniprot AC:P11279 (LAMP1_HUMAN), Dec. 9, 2015, <URL: https://www.uniprot.org/uniprot/P 11279. txt?version= 155>.
Riechmann, L. and Muyldermans, S., "Single Domain Antibodies: Comparison of Camel VH and Camelised Human VH Domains," Journal of Immunological Methods 231(1-2):25-38, Elsevier, Netherlands (Dec. 1999).
Roux, K.H., et al., "Structural Analysis of the Nurse Shark (New) Antigen Receptor (NAR): Molecular Convergence of NAR and Unusual Mammalian Immunoglobulins," Proceedings of the National Academy of Sciences of the United States of America 95(20):11804-11809, National Academy of Sciences, United States (Sep. 1998).
Schambach, A., et al., "Context Dependence of Different Modules for Posttranscriptional Enhancement of Gene Expression From Retroviral Vectors," Molecular Therapy 2(5):435-445, Cell Press, United States (Nov. 2000).
Shevach, E.M., Current Protocols in Immunology, Chapter 13 Complement, pp. 13.0.1-13.0.4, Jun. 2005.
Sommermeyer, D. and Uckert, W., "Minimal Amino Acid Exchange in Human TCR Constant Regions Fosters Improved Function of TCR Gene-Modified T Cells," Journal of Immunology 184(11):6223-6231, American Association of Immunologists, United States (Jun. 2010).
Su, C., et al., "Evolutionary Dynamics of the T-Cell Receptor VB Gene Family as Inferred from the Human and Mouse Genomic Sequences," Molecular Biology and Evolution 18(4):503-513, Oxford Academic, England (2001).

(56) References Cited

OTHER PUBLICATIONS

Traunecker, A., et al., "Janusin: New Molecular Design for Bispecific Reagents," International Journal of Cancer 7:51-52, Alan R. Liss, Inc., United States (1992).

Urlaub, G. and Chasin, L.A., "Isolation of Chinese Hamster Cell Mutants Deficient in Dihydrofolate Reductase Activity," Proceedings of the National Academy of Sciences USA 77(7):4216-4220, National Academy of Sciences, United States (Jul. 1980).

Van Der Linden, R.H., et al., "Improved Production and Function of Llama Heavy Chain Antibody Fragments by Molecular Evolution," Journal of Biotechnology 80(3):261-270, Elsevier Science Publishers, Netherlands (Jul. 2000).

Ward, E.S., et al., "Binding Activities of a Repertoire of Single Immunoglobulin Variable Domains Secreted from *Escherichia Coli*," Nature 341(6242):544-546, Nature Publishing Group, England (Oct. 1989).

Woolven, B.P., et al., "The Structure of the Llama Heavy Chain Constant Genes Reveals a Mechanism for Heavy-chain Antibody Formation," Immunogenetics 50(1-2):98-101, Springer Verlag, United States (Oct. 1999).

Zumla, et al., "Use of a Murine T-Cell Hybridoma Expressing Human T-Cell Receptor alpha and beta Products as a tool for the production of Human T-Cell Receptor-Specific Monoclonal Antibodies," Human Immunology 35(3):141-148, American Society for Histocompatibility and Immunogenetics, United States (1992).

Anonymous: "Immunomic Therapeutics—3D Animation Script—Final," Aug. 31, 2015, XP055266237, Retrieved from the Internet (URL:http://www.immunomix.com/wp-content/uploads/2015/09/IMMUNOMIX_ARKITEK_V4_Script_FINAL_083115.pdf), retrieved on Apr. 18, 2016.

Arruda, L.B., et al., "Dendritic Cell-lysosomal-associated Membrane Protein (LAMP) and LAMP-1-HIV-1 Gag Chimeras Have Distinct Cellular Trafficking Pathways and Prime T and B Cell Responses to a Diverse Repertoire of Epitopes," Journal of Immunology 177(4):2265-2275, American Association of Immunologists, United States (Aug. 2006).

Becker, C., et al., "Adoptive Tumor Therapy With T Lymphocytes Enriched Through an IFN-gamma Capture Assay," Nature Medicine 7(10):1159-1162, Nature Publishing Company, United States (Oct. 2001).

Burdek, M., et al., "Three-day Dendritic Cells for Vaccine Development: Antigen Uptake, Processing and Presentation," Journal of Translational Medicine 8:90, BioMed Central, England (Sep. 2010).

Ellinger, C., et al., "MHC Class-II Expression Targeting (CrossTAg) for the Generation of Tumor-Antigen-Specific CD4+ T Lymphocytes," Abstract—CIMT Cancer Immunotherapy Annual Meeting, Mainz, Germany (2013), XP055266213, accessed at https://www.medigene.com/fileadmin/download/abstracts/12_ellinger_-_mhc_class-ii_expression_targeting_crosstag_-cimt_2013.pdf, accessed Nov. 8, 2018.

Engels, B., et al., "Relapse or Eradication of Cancer Is Predicted by Peptide-major Histocompatibility Complex Affinity," Cancer Cell 23(4):516-526, Cell Press, United States (Apr. 2013).

Extended European Search Report for EP Application No. EP15202329, Munich, Germany, dated Aug. 29, 2016, 12 pages.

Frentsch, M., et al., "Direct Access to CD4+ T Cells Specific for Defined Antigens According to CD154 Expression," Nature Medicine 11(10):1118-1124, Nature Publishing Company, United States (2005).

GenBank, "Human GAGE-1 protein mRNA, complete cds," Accession No. U19142.1, accessed at https://www.ncbi.nlm.nih.gov/nuccore/U19142, accessed on Dec. 4, 1995.

GenBank, "Lysosome-associated membrane glycoprotein 1 precursor," Accession No. NP_005552, accessed at https://www.ncbi.nlm.nih.gov/protein/NP_005552, accessed on Jun. 23, 2018.

GenBank, "Lysosome-associated Membrane Glycoprotein 3 Precursor," Accession No. NP_055213, accessed at https://www.ncbi.nlm.nih.gov/protein/NP_055213.2, accessed on Jun. 11, 2018.

Hinrichs, C.S. and Rosenberg, S.A., "Exploiting the Curative Potential of Adoptive T-cell Therapy for Cancer," Immunological Reviews 257(1):56-71, Blackwell, England (Jan. 2014).

International Preliminary Report on Patentability for Application No. PCT/EP2016/082443, European Patent Office, Rijswijk, dated Jun. 26, 2018, 9 pages.

International Search Report and Written Opinion for International Application No. PCT/EP2016/082443, European Patent Office, Rijswijk, dated May 23, 2017, 16 pages.

Javorovic, M., et al., "Inhibitory Effect of RNA Pool Complexity on Stimulatory Capacity of RNA-pulsed Dendritic Cells," Journal of immunotherapy 31(1):52-62, Lippincott Williams & Wilkins, United States (Jan. 2008).

Kavanagh, D.G., et al., "Expansion of HIV-specific CD4+ and CD8+ T Cells by Dendritic Cells Transfected With mRNA Encoding Cytoplasm—or Lysosome—Targeted Nef," Blood 107(5):1963-1969, American Society of Hematology, United States (Mar. 2006).

Kempkes, B., et al., "Immortalization of Human B Lymphocytes by a Plasmid Containing 71 Kilobase Pairs of Epstein-barr Virus DNA," Journal of Virology 69(1):231-238, American Society for Microbiology, United States (Jan. 1995).

Knabel, M., et al., "Reversible MHC Multimer Staining for Functional Isolation of T-cell Populations and Effective Adoptive Transfer," Nature Medicine 8(6):631-637, Nature Publishing Company, United States (Jun. 2002).

Milosevic, S., et al., "Identification of Major Histocompatibility Complex Class II-restricted Antigens and Epitopes of the Epstein-barr Virus by a Novel Bacterial Expression Cloning Approach," Journal of Virology 80(21):10357-10364, American Society For Microbiology, United States (Nov. 2006).

Moosmann, A., et al., "B Cells Immortalized by a Mini-Epstein-Barr Virus Encoding a Foreign Antigen Efficiently Reactivate Specific Cytotoxic T Cells," Blood 100(5):1755-1764, American Society of Hematology, United States (Sep. 2002).

Regn, S., et al., "Ex Vivo Generation of Cytotoxic T Lymphocytes Specific for One or Two Distinct Viruses for the Prophylaxis of Patients Receiving an Allogeneic Bone Marrow Transplant," Bone Marrow Transplantation 27(1):53-64, Nature Publishing Group, England (Jan. 2001).

Schendel, D.J., et al., "Human CD8+ T lymphocytes," in: The Immunology Methods Manual, Lefkovits, Ed, pp. 670-690, 1997.

Schoenbrunn, A., et al., "A Converse 4-1BB and CD40 Ligand Expression Pattern Delineates Activated Regulatory T Cells (Treg) and Conventional T Cells Enabling Direct Isolation of Alloantigen-reactive Natural Foxp3+ Treg," Journal of Immunology 189(12):5985-5994, American Association of Immunologists, United States (Dec. 2012).

Steinle, A., et al., "In Vivo Expansion of HLA-B35 Alloreactive T Cells Sharing Homologous T Cell Receptors: Evidence for Maintenance of an Oligoclonally Dominated Allospecificity by Persistent Stimulation With an Autologous MHC/peptide Complex," The Journal of Experimental Medicine 181(2):503-513, Rockefeller University Press, United States (Feb. 1995).

Su, Z., et al., "Antigen Presenting Cells Transfected With LMP2a Rna Induce CD4+ LMP2a-specific Cytotoxic T Lymphocytes Which Kill via a Fas-independent Mechanism," Leukemia & Lymphoma 43(8):1651-1662, Informa Healthcare, England (Aug. 2002).

Wehner, C., et al., "Generation of Tumor Antigen-specific CD4+ and CD8+ T Cells by Simultaneous MHC-I and -II Epitope Presentation in Vitro and in Vivo," Journal for Immunotherapy of Cancer 2 (Suppl 3):P65, BioMed Central, England (2014).

Wilde, S., et al., "Dendritic Cells Pulsed With RNA Encoding Allogeneic MHC and Antigen Induce T Cells With Superior Anti-tumor Activity and Higher TCR Functional Avidity," Blood 114(10):2131-2139, American Society of Hematology, United States (Sep. 2009).

Wu, T.C., et al., "Engineering an Intracellular Pathway for Major Histocompatibility Complex Class II Presentation of Antigens," Proceedings of the National Academy of Sciences of the United States of America 92(25):11671-11675, National Academy of Sciences, United States (Dec. 1995).

(56) References Cited

OTHER PUBLICATIONS

Yu, X., et al., "Antigen-armed Antibodies Targeting B Lymphoma Cells Effectively Activate Antigen-specific CD4+ T Cells," Blood 125(10):1601-1610, American Society of Hematology, United States (Mar. 2015).

Van Nuffel, An M.T. et al., "Dendritic cells loaded with mRNA encoding full-length tumor antigens prime CD4+ and CD8+ T cells in melanoma patients," *Molecular Therapy* 20:1063-1074, Elsevier, Netherlands (2012).

Office Action for U.S. Appl. No. 15/579,117, dated Sep. 25, 2019 (16 pages).

Bacher et al., "Characterization of antigen-specific naive and memory T cell subsets," Miltenyi Biotec. (2015) (5 pages).

Cohen et al., "Isolation of neoantigen-specific T cells from tumor and peripheral lymphocytes," J Clin Invest. 125(10):3981-3991 (2015).

\* cited by examiner

GENERATION OF ANTIGEN-SPECIFIC TCRS

FIELD OF THE INVENTION

The present invention contemplates methods for the generation of human antigen-specific T lymphocytes. The methods employ MHC class-II targeting signals fused to an antigen or fragment thereof to obtain MHC class I and II presentation of RNA-coded proteins. Accordingly, the present invention concerns expression vectors comprising MHC class-II targeting signals and at least one antigen or fragment thereof and its use for the in vitro generation of antigen-specific T lymphocytes. T cell clones and T cell receptors (TCRs) specific for tumor antigens or viral antigens are also described.

BACKGROUND OF THE INVENTION

The adoptive T cell transfer uses T cell-based cytotoxic responses to control chronic viral infections and tumors. T cells that have a natural or genetically engineered reactivity to a patient's cancer are generated in vitro and then transferred back into the patient. The adoptive transfer of autologous tumor-infiltrating lymphocytes (TIL) has been used to successfully treat patients with advanced tumors. The principal limitations of TIL therapy for broad application in the clinic are the oftentimes poor immunogenicity of tumors as well as the mechanisms of negative T cell selection in the thymus that efficiently delete T cells with auto-antigen-specificity. Therefore, in many cases, neither T cells with high avidity for tumor-specific antigens nor T cells with the desired specificity can be isolated from patient blood or tumor resections. For this, the transfer of genetically re-directed peripheral blood lymphocytes (PBL) offers a possibility to overcome these limitations.

Further, in cancerous and chronic infections T lymphocytes lose function and become exhausted.

With the help of T cell receptor (TCR) gene therapy millions of tumor-reactive T cells can be rapidly generated from patient blood. TCR gene therapy paves the way to a flexible method to transfer tumor-specificity to expandable and functionally promising T cell subpopulations. It comprises the transfer of isolated TCR genes of defined antigen-specific T cell clones into recipient T lymphocytes of human leukocyte antigen (HLA)-matched donors to equip them with required antigen specificities.

Adoptive T cell therapy with $CD8^+$ cytotoxic T lymphocytes (CTL) is a promising immunotherapy, for cancerous or viral diseases. To increase clinical responses, complementary transfer of $CD4^+$ helper T cells offers a possibility to enhance $CD8^+$ CTL responses. $CD4^+$ T lymphocytes are known to provide pivotal help for $CD8^+$ CTL, as well as to have a critical effect on the generation of long-lasting $CD8^+$ memory T cells. Rapid and efficient isolation and characterization of tumor antigen-specific $CD4^+$ and $CD8^+$ T lymphocytes is therefore of importance.

Many tumors express MHC class II molecules and therefore TCRs from $CD4^+$ T cells are particularly useful to attack directly attack these tumors.

In order to extend the capacity to use adoptive cell therapy (ACT) to treat patients with more rapidly growing tumors or chronic viral diseases, it is a goal to transfer enriched, peptide-specific effector T cells (both CD4 T helper cells and cytotoxic T lymphocytes) that have been selected for their ligand specificities to effectively attack viruses or tumor cells while avoiding serious attack of normal tissues. These cells are to be rapidly expanded to large numbers ex vivo and then used for ACT. Alternatively, the T cell receptors (TCR) of such ligand-specific T cells can be cloned and expressed as TCR transgenes in activated lymphocytes, using either recipient peripheral blood lymphocytes or activated T cell clones with defined specificities that grow well and do not have the capacity to attack normal host tissues.

As a consequence, antigen-specific TCRs and efficient methods for the isolation of these TCRs are needed.

OBJECTIVES AND SUMMARY OF THE INVENTION

Therefore, it is an objective of the invention to provide efficient methods for the isolation of T cells with antigen-specific TCRs. It would be desirable to provide a method for the generation of CD4 TCRs and/or CD8 TCRs. Further it is an objective of the invention to provide TCRs or functional parts thereof, such as CDR3 regions. It would be advantageous to achieve TCRs that exhibit a high and/or optimal affinity against tumor antigens.

Therefore, a first aspect of the invention contemplates a method of generating human antigen-specific T lymphocytes comprising the following steps:
A) expression of at least one fusion protein comprising
    at least one antigen or a fragment thereof,
    an endoplasmatic reticulum (ER)-translocation signal sequence preceding the N-terminus of the antigen, and
    a transmembrane and cytoplasmic domain comprising an endosomal/lysosomal targeting sequence following the C-terminus of the antigen,
in antigen presenting cells; and
B) exposing of a cell population comprising T lymphocytes to the antigen presenting cells of step A) in vitro in order to activate antigen-specific T lymphocytes specific for the antigen expressed by the antigen presenting cell.

The fusion of the targeting sequence, in particular in combination with the ER-translocation signal sequence, to the desired antigen or fragment thereof allows the efficient loading of MHC class-II complexes, also for cellular proteins which are usually presented via the MHC class-I complex. Also the loading of the MHC class-I complexes is achieved by the above described method. Therefore, the method allows the generation of $CD4^+$ TCRs as well as $CD8^+$ TCRs.

Expression of the at least one fusion protein in step A) may be transient expression or stable expression, preferably transient expression, for example by introducing ivt-RNA coding for the at least one fusion protein. The expression of ivt-RNA has the advantage that quality-controlled ivt-RNA can be rapidly produced and carries no immunogenic protein contaminants.

In specific embodiments, the fusion protein may comprise at least two antigens or fragments thereof.

In some embodiments the method may further comprise the step of enrichment of activated T lymphocytes. This enrichment step typically comprises the following steps:
(a) contacting the cell population comprising activated antigen-specific T lymphocytes with at least one binding molecule which specifically binds to at least one marker protein specifically expressed by activated T lymphocytes;
(b) isolating T lymphocytes to which the at least one binding molecule is bound.

In preferred embodiments, the at least one marker protein specifically expressed by activated T lymphocytes is selected from the group comprising Ox40, CD137, CD40L, PD-1, IL-2 receptor, interferon γ, IL-2, GM-CSF and TNF-α. In addition, in step (a) the cells may be further contacted with a binding molecule that specifically binds to CD4 and/or with a binding molecule that specifically binds to CD8.

In specific embodiments selecting activated CD4 T cells comprises the following steps:
(a1) contacting the cell population of step B) with an antibody against CD40 in order to block the interaction between CD40-CD40L of the antigen presenting cells and the antigen-specific T lymphocytes and to accumulate CD40L at the surface of T lymphocytes;
(a2) contacting the cell population comprising activated antigen-specific T lymphocytes with an anti-CD40L antibody;
(b) isolating the T lymphocytes marked with an anti-CD40L antibody and an anti-CD4 antibody.

Another embodiment refers to the method according to any one of the preceding claims, wherein the method further comprises the step
C2) identification of antigen-specific T lymphocytes, comprising the following steps:
a) incubation of expanded cell clones of the cell population comprising activated antigen-specific T lymphocytes with
   (i) antigen presenting cells as defined in step A), and
   (ii) control antigen presenting cells;
b) comparison of the activation profile of the incubation with (i) and (ii) for each cell clone;
c) identification of antigen-specific cell clones based on the comparison of b);
wherein the activation by (i) but not by (ii) indicates that the cell clone is antigen-specific; the activation by (i) and by (ii) indicates that the cell clone is antigen unspecific; activation neither by (i) nor by (ii) indicates that the cell clone is not activated.

In step B) the antigen presenting cells are added to the cell population comprising T lymphocytes at least once, or at least twice, or at least three times, or three times. The time interval between repeated additions of antigen presenting cells may be 7 to 21 days, 12 to 16 days, or 13 to 15 day, or 14 days.

The ER translocation signal sequence is derived from an endosomal/lysosomal associated protein. The endosomal/lysosomal associated protein may be selected from the group consisting of LAMP1, LAMP2, DC-LAMP, CD68 or CD1b, preferably the endosomal/lysosomal associated protein is LAMP1. Preferably, the ER translocation signal sequence is human. In specific embodiments the ER translocation signal sequence comprises the sequence SEQ ID NO: 33 or a fragment thereof. In more specific embodiments the ER translocation signal sequence consists of the following sequence SEQ ID NO: 33.

The transmembrane and cytoplasmic domain comprising an endosomal/lysosomal targeting sequence may be derived from LAMP1 or DC-LAMP, preferably DC-LAMP. Preferably the transmembrane and cytoplasmic domain comprising an endosomal/lysosomal targeting sequence is human.

Typically, the antigen presenting cells are selected from dendritic cells, activated B cells, monocytes, macrophages, EBV-transformed lymphoblastoid cell lines, preferably dendritic cells, more preferably monocyte derived dendritic cells.

Usually, the cell population comprising T lymphocytes is a population of peripheral blood lymphocytes. The cell population comprising T lymphocytes may be a population of unseparated peripheral blood lymphocytes. The cell population may be enriched for T lymphocytes, preferably $CD8^+$ and/or $CD4^+$ T lymphocytes by means known to the person skilled in the art.

Another aspect of the application is a T lymphocyte obtainable by the methods described herein.

A further aspect of the invention refers to an expression vector comprising:
  a human endoplasmatic reticulum (ER)-translocation signal, and
  a human transmembrane and cytoplasmic domain comprising an endosomal/lysosomal targeting sequence.

The vector may comprise a promotor for in-vitro mRNA transcription. The ER translocation signal sequence is derived from an endosomal/lysosomal associated protein, for example LAMP1, LAMP2, DC-LAMP, CD68, CD1b, most preferably LAMP1. Preferably, the ER translocation signal sequence is human. In specific embodiments the ER translocation signal sequence comprises the sequence SEQ ID NO: 33 or a fragment thereof. In more specific embodiments the ER translocation signal sequence consists of the following sequence SEQ ID NO: 34.

The endosomal/lysosomal targeting sequence may be derived from LAMP1 or DC-LAMP, preferably DC-LAMP. The endosomal/lysosomal targeting sequence is typically a part of a transmembrane and cytoplasmic domain. Thus, the transmembrane and cytoplasmic domain comprising an endosomal/lysosomal targeting sequence may be derived from LAMP1 or DC-LAMP, preferably DC-LAMP. Preferably the transmembrane and cytoplasmic domain comprising an endosomal and/or lysosomeal targeting sequence is human. Typically, the endosomal/lysosomal targeting sequence comprises the motif Y-XX (X stands for any naturally occurring amino acid) followed by a hydrophobic amino acid (SEQ ID NO: 38). Preferably, the endosomal/lysosomal targeting sequence is YQRI (SEQ ID NO: 39). The transmembrane and cytoplasmic domain comprising an endosomal/lysosomal targeting sequence may comprise the sequence SEQ ID NO: 54 or a fragment thereof. For example, the transmembrane and cytoplasmic domain comprising an endosomal/lysosomal targeting sequence may comprise the sequence SEQ ID NO: 35 or a fragment thereof.

In some embodiments the expression vector further comprises restriction sites between the ER translocation signal sequence and the human transmembrane and cytoplasmic domain comprising an endosomal/lysosomal targeting sequence. In other embodiments, the vector further comprises at least one antigen, or a fragment thereof which is inserted between human endoplasmatic reticulum (ER)-translocation signal sequence, and the human transmembrane and cytoplasmic domain comprising an endosomal/lysosomal targeting sequence.

In specific embodiments, the vector comprises a sequence encoding at least two antigens or fragments thereof. In some embodiments the vector comprises nucleic acid sequence encoding a full length amino acid sequence of an antigen. Alternatively, the vector comprises a fragment of a nucleic acid sequence encoding an amino acid sequence of an antigen.

Typically, the antigen is a tumor antigen or a viral antigen. The tumor antigen may be selected from the group consisting of viral tumor antigen, tumor-specific antigen, tumor associated antigen and an antigen carrying patient specific mutations and being expressed in tumor cells of the patient. The tumor antigen is a tumor associated antigen, preferably the tumor associated antigen is a cancer/testis antigen (C/T antigen). The C/T antigen may be selected from the group comprising MAGE family members, for example MAGE-A1, MAGE-A3, MAGE-A4, but not limited to these, tumor antigens comprising single point mutations, NY-ESO1, tumor/testis-antigen 1B, GAGE-1, SSX-4, XAGE-1, BAGE, GAGE, SCP-1, SSX-2, SSX-4, CTZ9, CT10, SAGE and CAGE. Preferably the C/T antigen may be selected from the group consisting of GAGE-1, SSX-4 and XAGE-1.

Another aspect of the invention refers to the use of the expression vector as described herein for in vitro generation of antigen-specific T lymphocytes.

A further aspect of the invention refers to T-lymphocytes for use in a method of preventing or treating cancer comprising administering to a mammal the T-lymphocytes generated by methods as described herein.

Another aspect refers to a method for generating an antigen-specific TCR comprising the steps of the methods described above and further comprising the step of isolating a TCR from the activated antigen-specific lymphocyte generated by the methods as described herein.

Another aspect refers to a TCRs specific for GAGE-1, SSX-4 and XAGE-1, respectively.

FIGURE LEGENDS

FIG. 1: Targeted MHC class-II presentation for the activation and isolation of antigen-specific CD4+ T cells. (a) Schematic representation of the various EBNA-3C constructs used to validate the functionality and necessity of the CrossTAg-signal. The ORF (ATG to STOP), the different components of the CrossTAg-signal (LAMP1 and DC-LAMP), the HLA-DR11-restricted EBNA-3C epitope (3H10) and the polyA120 stretch are depicted. (b) The CrossTAg-signal facilitates efficient MHC class-II cross-presentation. IFN-γ secretion of EBNA-3C-specific CD4+ T cell clone 3H10 at 16 h of co-culture with ivt-RNA-transfected APC (monocyte-derived DC prepared in three days (3d-mDC) or mini-Epstein-Barr virus-(EBV)-transformed lymphoblastoid cell lines (mLCL)). Values are presented as the mean+SD of triplicates. (c) Expression of the activation marker CD40L is suitable for the isolation of antigen-specific CD4+ T cells. CellTrace™ violet labeled 3H10 cells were mixed with autologous PBL in decreasing concentrations and co-cultured with EBNA-3C-CrossTAg ivt-RNA-transfected mDC (APC) of the autologous donor. Activation-induced CD40L expression on CD4+ T cells was assessed at 6 h of co-culture.

Figure 2:
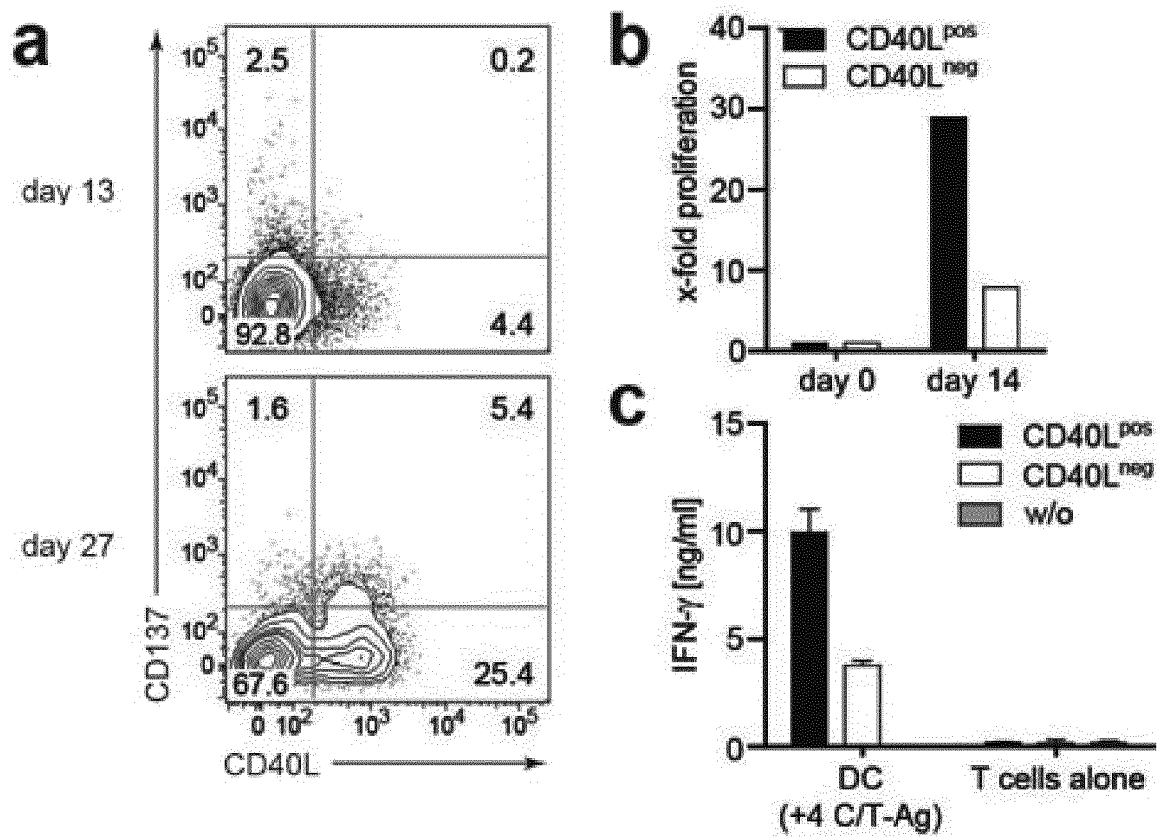

FIG. 2: Induction and enrichment of C/T-antigen-specific CD4+ T cells from unseparated PBL. (a) Activation-induced CD40L and CD137 surface expression on CD4+ T cells from C/T-antigen-primed PBL. Activation marker expression was measured 6 h after specific re-stimulation of the PBL in vitro culture on day 13 and 27, respectively. (b) Direct comparison of proliferative capacity of bulk $CD40L^{positive}$ and $CD40L^{negative}$ CD4+ T cell lines. On day 28, CD4+ T cells were separated from the primed PBL culture according to their CD40L expression. Total cell numbers were assessed after FACS separation (day 0) and at the end of the 14 day interval following specific re-stimulation (day 14). Depicted is the x-fold proliferation relative to day 0. (c) Comparison of induced cytokine secretion following antigen-specific re-stimulation. IFN-γ secretion of bulk $CD40L^{positive}$ and $CD40L^{negative}$ CD4+ T cell lines was measured at 16 h of co-culture with CrossTAg-antigen ivt-RNA-transfected mDC. Values are presented as the mean+SD of triplicates.

Figure 3:
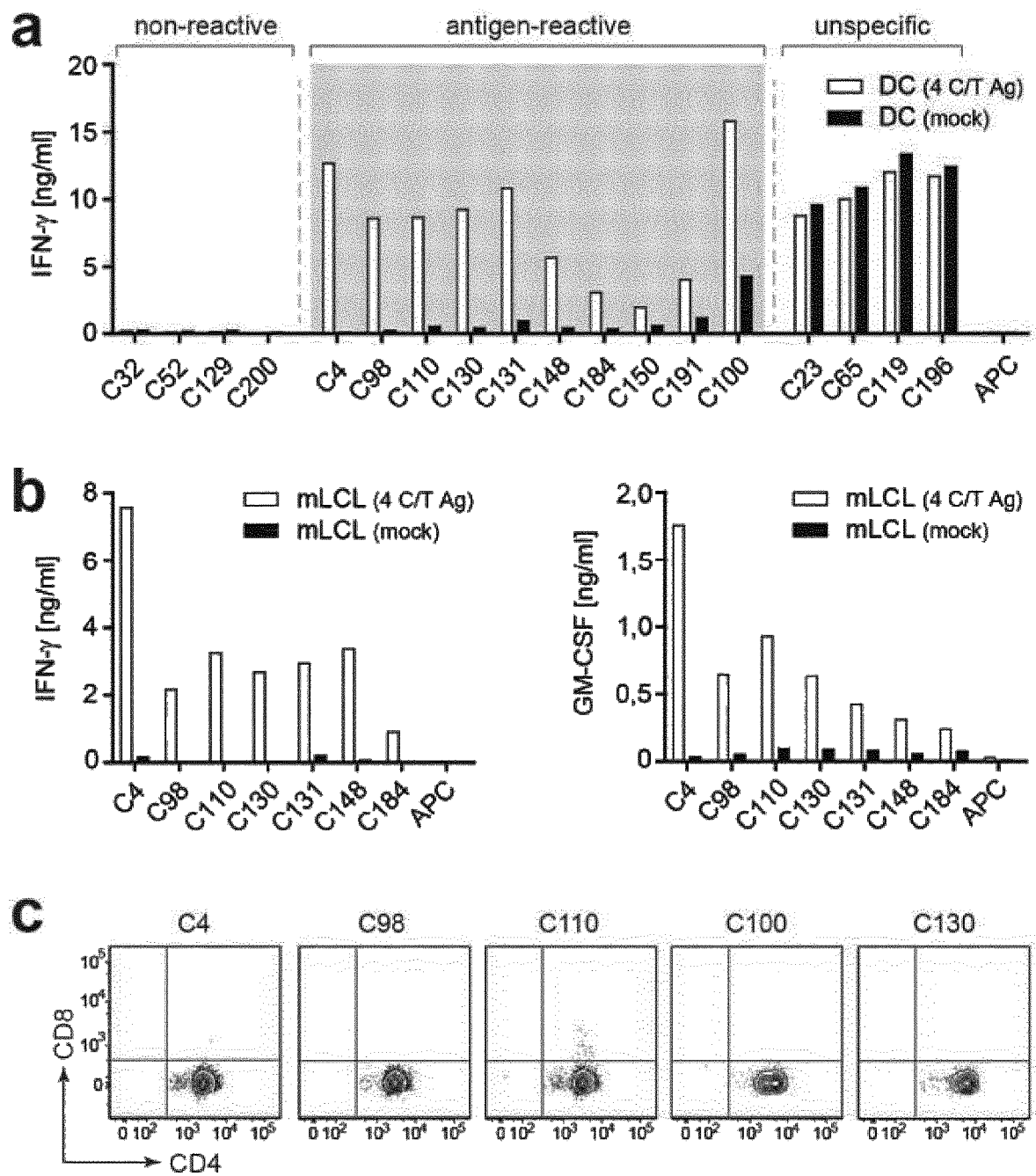

FIG. 3: Screening for C/T-antigen-specific CD4+ T cell clones. (a) Exemplary screening data of clones derived from the C/T-antigen-primed PBL culture. IFN-γ secretion was assessed at 16 h of co-culture with CrossTAg-antigen ivt-RNA-transfected mDC (mixture of 4 antigens). Bars represent single values. (b) Validation of C/T-antigen reactivity of selected T cell clones. Cytokine secretion (IFN-γ and GM-CSF) was assessed after co-culture with ivt-RNA-transfected mLCL (mixture of 4 antigens). Data is depicted as single values. (c) Confirmation of CD4 co-receptor expression. Exemplary clones are shown.

Figure 4:
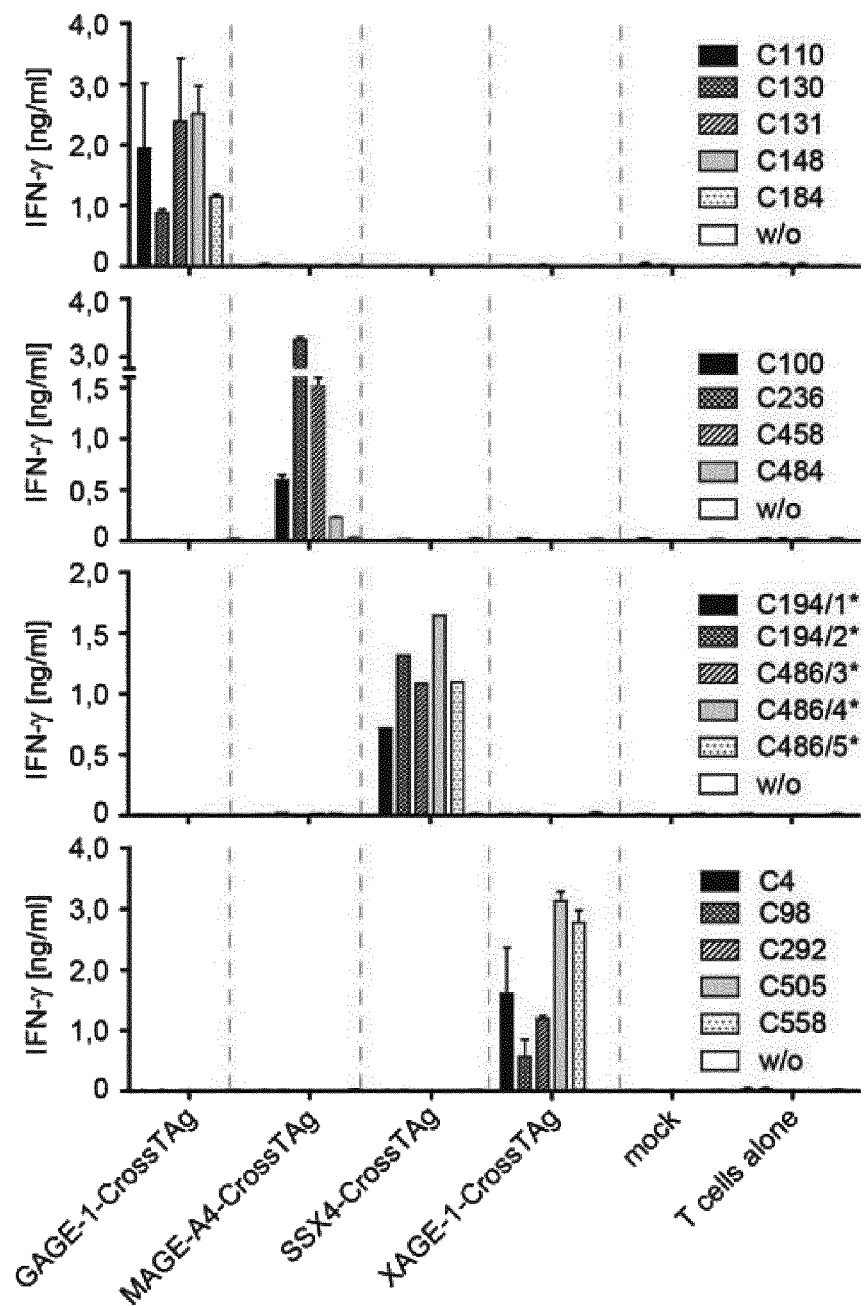

FIG. 4: Assessment of antigen-specificity. Exemplary data for CD4+ T cell clones found to display single C/T-antigen-specificity. IFN-γ secretion was measured after co-culture with ivt-RNA-transfected mLCL. Values are presented as the mean+SD of duplicates or as single data points where indicated (*).

Figure 5:
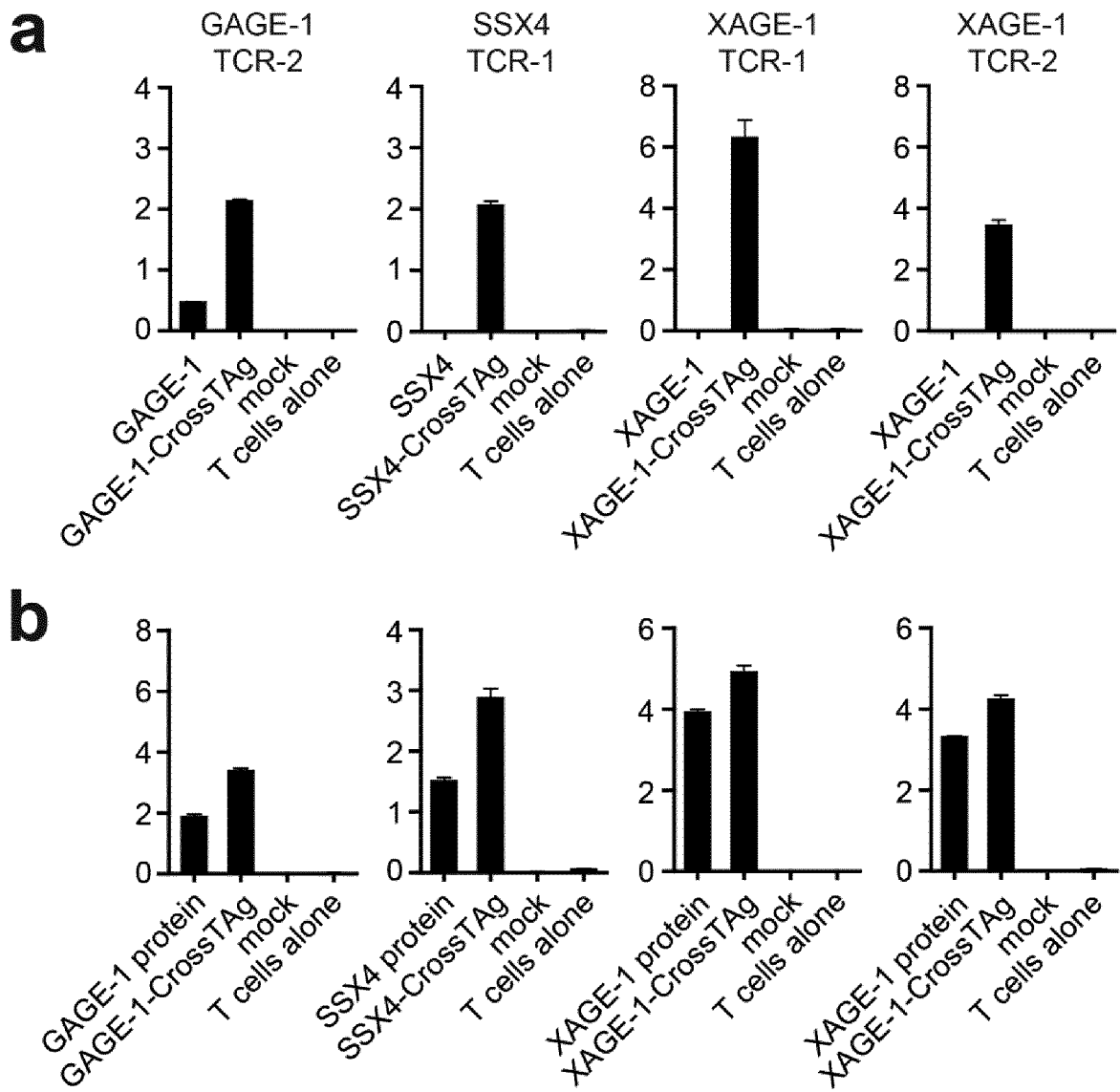

FIG. 5: Necessity of CrossTAg-signal and protein recognition. (a) Necessity of the CrossTAg-signal for ivt-RNA-based CD4+ T cell clone activation. (b) Recognition of physiologically processed, exogenous recombinant proteins. Stimulatory capacity of antigen-CrossTAg ivt-RNA-transfected APC (mLCL) in direct comparison to mLCL transfected with antigen-ivt-RNA lacking the CrossTAg-signal (a) or mLCL loaded with recombinant protein (b) as measured by IFN-γ secretion of isolated CD4+ T cell clones carrying unique TCRs. Mock APC and T cells alone served as controls. Values are presented as the mean+SD of triplicates.

Figure 6:
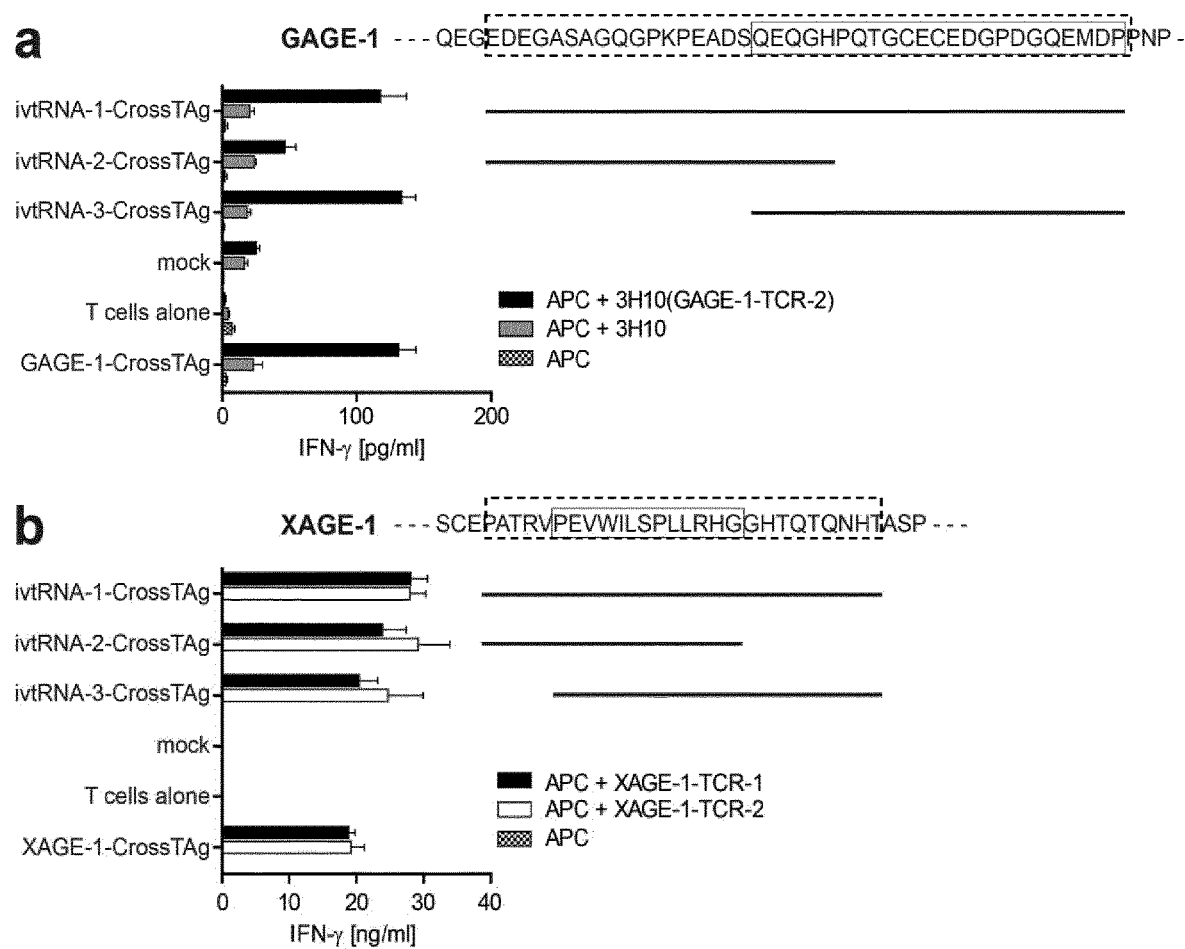

FIG. 6: Definition of MHC class-II epitope core sequences. The peptide fragments found by direct MHC class-II epitope identification (DEPI) (box with dashed line) were validated using short CrossTAg-ivt-RNA constructs. GAGE-1-TCR-2 transgenic 3H10 T cells (a) or XAGE-1-TCR-1 and-TCR-2 T cells (b) were co-cultured either with overlapping short CrossTAg-ivt-RNA construct-(indicated as black bars) or full-length antigen-CrossTAg ivt-RNA-transfected APC (mLCL). IFN-γ secretion was assessed at 16 h of co-culture and recognized epitope core sequences are depicted (box with solid line). Co-cultures with mock transfected APC or T cells alone served as controls. Values are presented as the mean+SD of triplicates.

Figure 7:
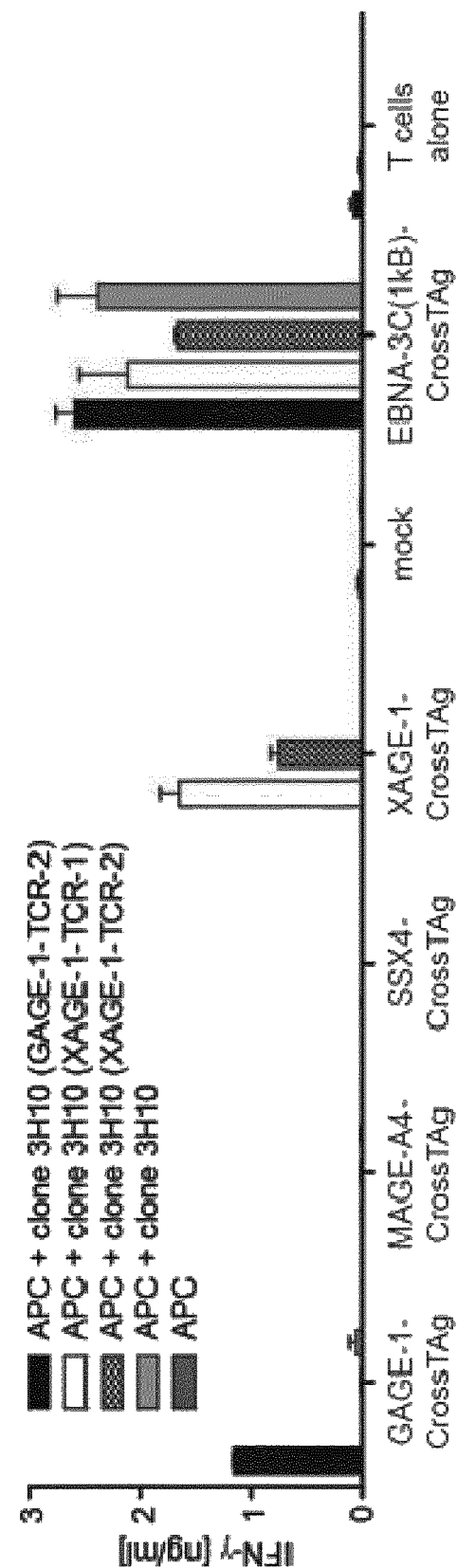

FIG. 7: Transgenic expression of C/T-antigen-specific CD4+ T cell receptors. 3H10 T cells were transfected with ivt-RNA coding for corresponding TCR-α and-β chains of CD4+ T cell clones GAGE-1-TCR-1, XAGE-1-TCR-1 or-TCR-2. TCR-transgenic 3H10 cells were co-cultured with antigen-loaded APC (mLCL) and IFN-γ secretion was detected at 16 h of co-culture. Co-cultures with mock transfected APC or T cells alone served as controls. Values are presented as the mean+SD of triplicates.

Figure 8:
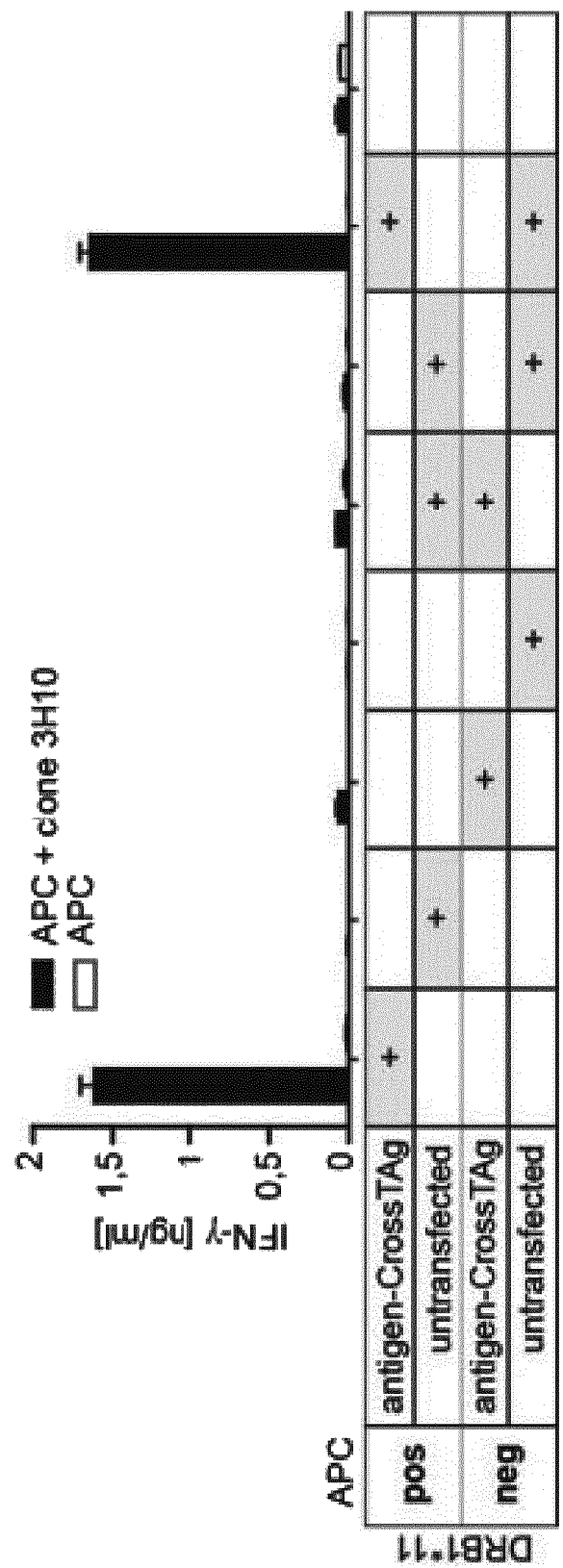

FIG. 8: CrossTAg signal facilitates MHC class-II loading via cell internal [endogenous] presentation pathways. HLA-DRB1*11:01-positive and HLA-DRB1*11:01-negative DCs were transfected with EBNA-3C-CrossTAg ivt-RNA. Transfected and un-transfected DCs were co-incubated in all possible combinations and 12 h later co-cultured with EBNA-3C-specific CD4+ T cell clone 3H10. IFN-γ secretion of 3H10 cells was measured at 16 h of co-culture with DCs. Values are presented as the mean+SD of triplicates.

Figure 9:
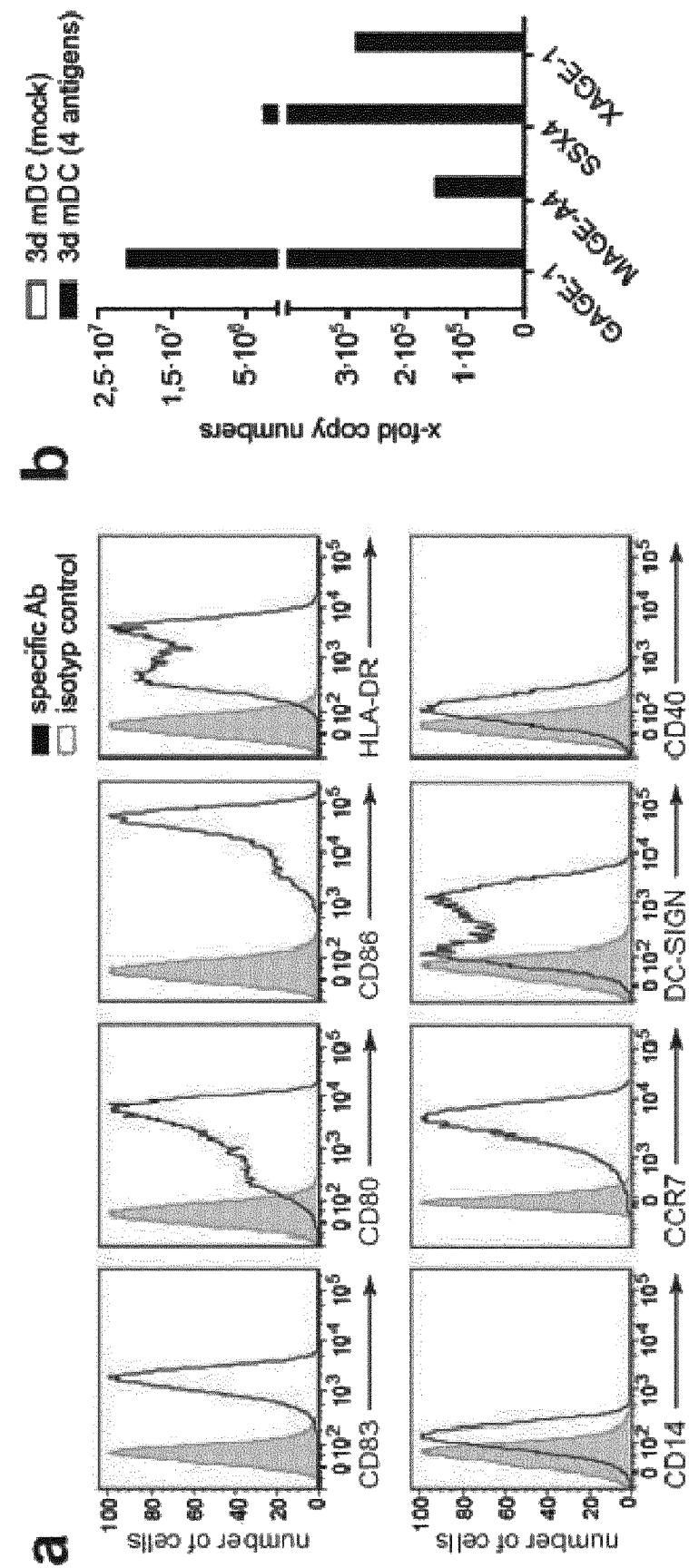

FIG. 9: Characterization of 3d mDCs for PBL priming. (a) Surface marker expression as detected by staining with monoclonal antibodies (open curves) and matched isotype controls (filled grey curves). (b) Antigen mRNA levels of ivt-RNA-transfected mDC. Depicted is the x-fold increase in antigen mRNA copy numbers in relation to non-transfected mDC. Antigen mRNA copy numbers were assessed by qRT-PCR using antigen-specific primers.

Figure 10:
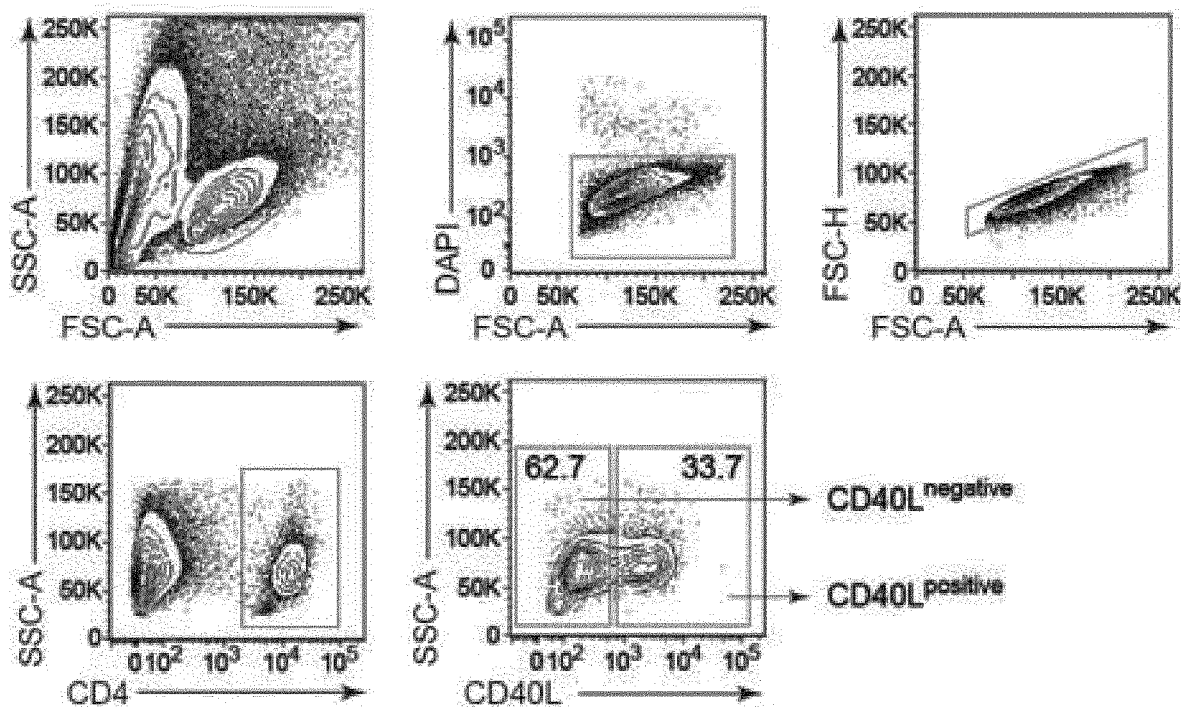

FIG. 10: Gating strategy for CD40L-based sorting of C/T-antigen-specific CD4+ T cells. Lymphocytes were selected according to their forward (FSC; FSC-A: forward scatter area; FSC-H: forward scatter height) and sideward scatter (SSC-A). DAPI was used for the exclusion of dead cells. CD4-positive cells of the single cell fraction (FSC-A/FSC-H) were subsequently sorted according to their CD40L expression and established as bulk CD40L$^{positive}$ and CD40L$^{negative}$ CD4$^+$ T cell lines. Additionally, CD40L$^{positive}$ CD4$^+$ T cells were sorted into 96-well plates on a single cell basis.

Figure 11:
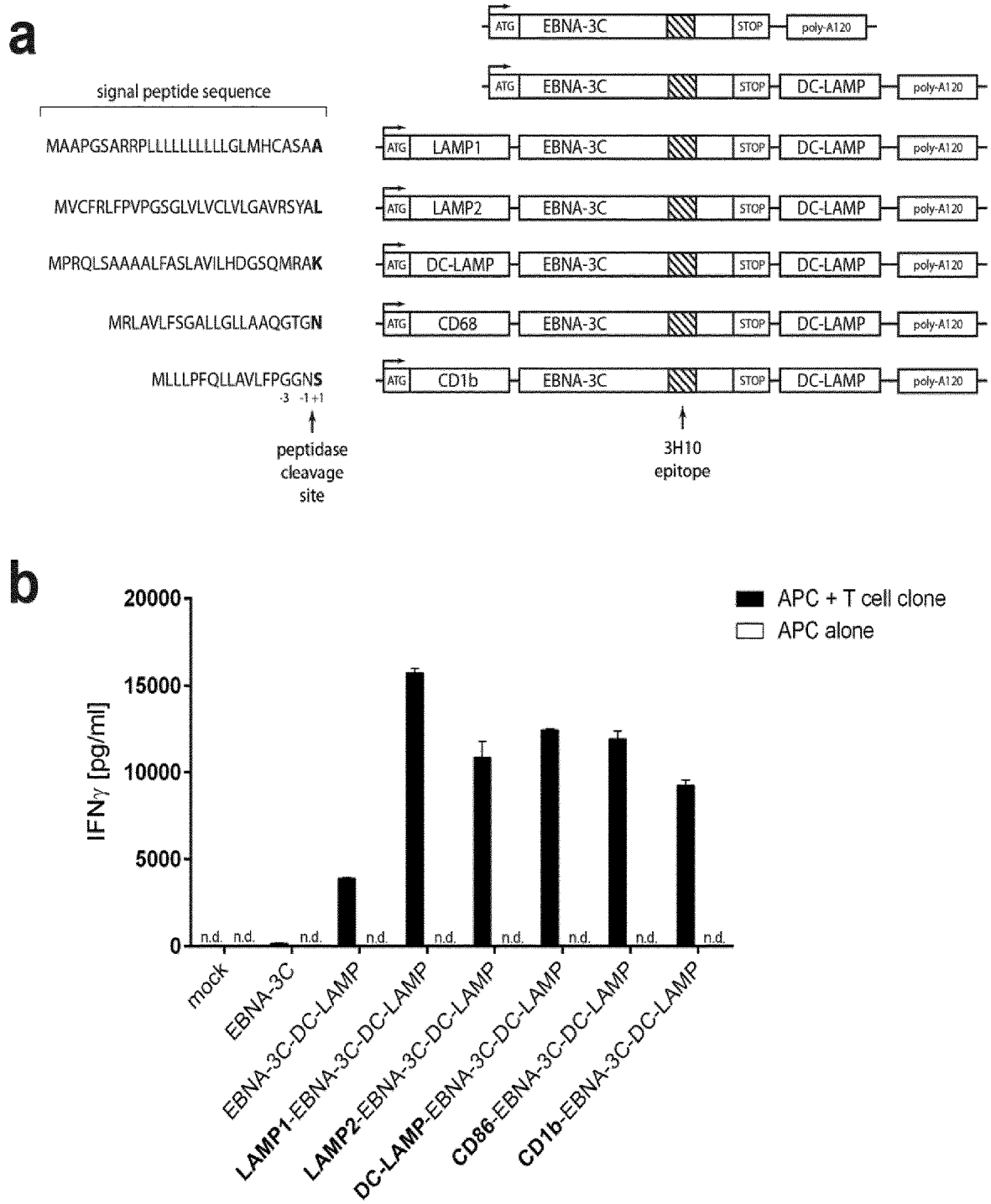

FIG. 11: Alternative ER translocation signal sequences (a) Schematic depiction of vector constructs used for ivt-RNA production. The target antigen of the characterized CD4$^+$ T cell clone 3H10 (EBNA-3C-specific, HLA-DRB1*11:01-restricted) was cloned into the pGEM vector system comprising combinations of ER translocation signals of human LAMP1, LAMP2, DC-LAMP, CD68 or CD1b (5' to the antigen sequence) and the endosomal/lysosomal targeting sequence of human DC-LAMP (3' to the antigen sequence), the endosomal/lysosomal targeting sequence of DC-LAMP alone or no translocation and targeting sequence. In addition, amino acid sequences of the employed signal peptide sequences (ER translocation signals) are depicted indicating the predicted peptidase cleavage sites. (b) Cells of CD4$^+$ T cell clone 3H10 were co-cultured with single ivt-RNA species-transfected APC (mLCL). Co-cultures with mock transfected APC served as controls. IFN-γ secretion was detected by standard IFN-γ ELISA 16 h after the start of the co-culture. Values are presented as the mean+SD of triplicates.

Figure 12:
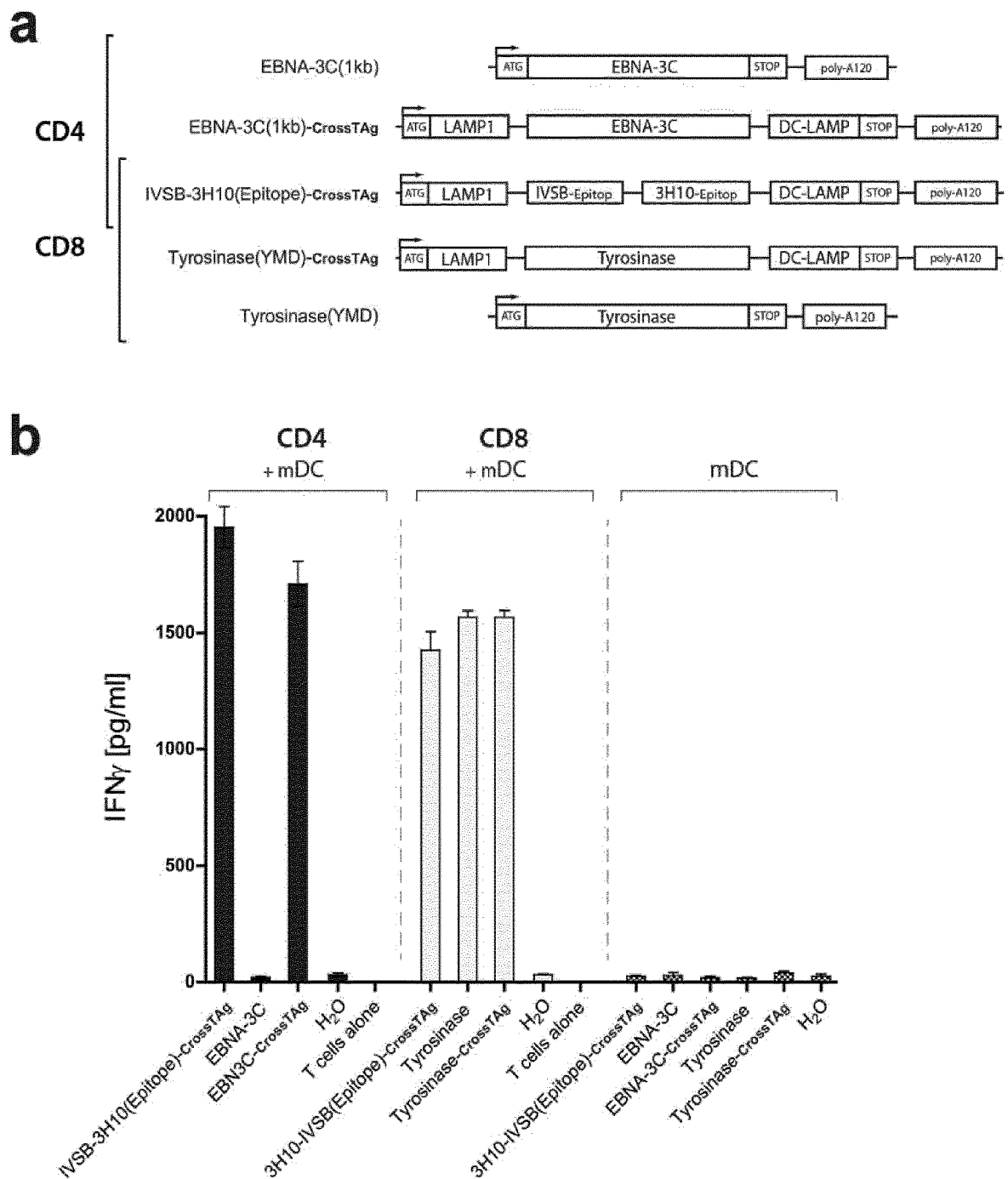

FIG. 12: Simultaneous MHC class-II and MHC class-I presentation using the CrossTAg targeting signal. (a) Schematic depiction of the vector constructs used for ivt-RNA production. The target antigens of a characterized CD4$^+$ T cell clone 3H10 (EBNA-3C-specific, HLA-DRB1*11:01-restricted) and a characterized CD8$^+$ T cell clone IVSB (tyrosinase-specific, HLA-A2*01:01-restricted) were cloned into the pGEM vector system with or without the CrossTAg targeting sequences. EBNA-3C was cloned as a 1 kb fragment (aa 421-780) of the full gene sequence and contains the epitope for clone 3H10. For the generation of the IVSB-3H10(Epitope)-CrossTAg construct, instead of a full antigen sequence, mini-genes comprising the epitopes of clone 3H10 (EBNA-3C, aa 628-641, VVRMFMRERQLPQS; SEQ ID NO: 36) and clone IVSB (tyrosinase, aa 369-377, YMDGTMSQV; SEQ ID NO: 37) were cloned sequentially into the pGEM-CrossTAg vector backbone. To facilitate the stabilization of transcribed ivt-RNA species in the cytoplasm, all pGEM vector constructs carry a poly-A tail comprising 120 adenine base pairs (poly-A120) 3' of the open reading frame (ORF). (b) Separate fractions of mature DC (mDC) of a HLA-A2*01:01-, HLA-DRB1*11:01-double positive donor were transfected with single ivt-RNA species listed in (a). Seven hours after transfection, 1*10$^5$ cells of the distinct mDC populations were co-cultured with 1*10$^5$ cells of CD4$^+$ T cell clone 3H10 or CD8$^+$ T cell clone IVSB (1:1 ratio). Co-cultures with mock transfected mDC (H$_2$O) or T cells alone served as controls. IFN-γ secretion was detected by standard IFN-γ ELISA 16 h after the start of the co-culture. Values are presented as the mean+SD of triplicates.

DETAILED DESCRIPTION OF THE INVENTION

Before the invention is described in detail with respect to some of its preferred embodiments, the following general definitions are provided.

The present invention as illustratively described in the following may suitably be practiced in the absence of any element or elements, limitation or limitations, not specifically disclosed herein.

The present invention will be described with respect to particular embodiments and with reference to certain figures but the invention is not limited thereto but only by the claims.

Where the term "comprising" is used in the present description and claims, it does not exclude other elements. For the purposes of the present invention, the term "consisting of" is considered to be a preferred embodiment of the term "comprising of". If hereinafter a group is defined to comprise at least a certain number of embodiments, this is also to be understood to disclose a group which preferably consists only of these embodiments.

Where an indefinite or definite article is used when referring to a singular noun, e.g. "a", "an" or "the", this includes a plural of that noun unless something else is specifically stated.

As used herein, the term "expression" refers to the process by which a polypeptide is produced based on the nucleic acid sequence of a gene. Accordingly the term "expressed" protein or polypeptide comprises, without limitation, intracellular, transmembrane and secreted proteins or polypeptides.

Technical terms are used by their common sense. If a specific meaning is conveyed to certain terms, definitions of terms will be given in the following in the context of which the terms are used.

One aspect of the present invention refers to a method of generating human antigen-specific T lymphocytes comprising the following steps:

A) expression of at least one fusion protein comprising
   at least one antigen or a fragment thereof,
   an endoplasmatic reticulum (ER)-translocation signal sequence preceding the N-terminus of the antigen, and
   a transmembrane and cytoplasmic domain comprising an endosomal/lysosomal targeting sequence following the C-terminus of the antigen,
in antigen presenting cells; and B) exposing of a cell population comprising T lymphocytes to the antigen presenting cells of step A) in vitro in order to activate antigen-specific T lymphocytes specific for the antigen expressed by the antigen presenting cell.

The fragment may be a sequence of the antigen that is specific for this antigen, i.e. does not occur in another protein or peptide of a mammal, especially of a human. The fragment may be shorter than the sequence of the antigen, such as at least 5%, at least 10%, at least 30%, at least 50%, at least 70%, at least 90% shorter than the antigen. The fragment may have a length of at least 9, at least 10, at least 11, at least 12, at least 13, at least 14, at least 15 or more amino acids.

In one embodiment the fusion protein comprises at least two antigens or fragments thereof. The fusion protein may comprise at least three, at least 4, at least 5, at least 6, at least 7, at least 8, at least 9, at least 10 antigens or fragments thereof. The fusion protein may comprise less than 100, less than 50, less than 40, less than 30, less than 20, less than 10 antigens or fragments thereof.

The term "activate antigen-specific T lymphocytes" refers to the activation of naive T cells (de novo induction) and to the activation of memory T lymphocytes (reactivation).

Typically the antigen presenting cells and the cell population comprising T lymphocytes are from the same donor. Also allorestricted set-ups as described in EP1910521 are contemplated, in which a nucleic acid encoding a MHC molecule is expressed in the antigen presenting cells of the donor who does not carry the MHC gene corresponding to said MHC molecule that is transferred.

Expression of the at least one fusion protein in step A) may be transient expression or stable expression. In preferred embodiments the expression is transient expression, for example by introducing ivt-RNA coding for the at least one fusion protein. The expression of ivt-RNA has the advantage that quality-controlled ivt-RNA can be rapidly produced and carries no immunogenic protein contaminants.

By the exposure of the T lymphocytes, also termed priming, a number of different activated lymphocyte populations emerge in vitro. Typically, exposing in step B) is co-culturing the antigen presenting cells with a cell population comprising T lymphocytes. T cells recognizing the MHC:epitope complexes of the antigen presenting cells are activated, a fraction of which are specific for the complexes of MHC molecules presenting an epitope of the antigen expressed in step A). These sought-after T cells must be separated from T cells that recognize MHC molecules irrespective of peptide or MHC molecules that present epitopes that are not derived from the antigen expressed in step A).

For the exposure of the antigen presenting cells in step B), the antigen presenting cells are added to a population comprising T lymphocytes at least once. The first addition of the antigen presenting cells is also termed priming. The antigen presenting cells can be added several times, for example, at least twice or at least three times. The second and every subsequent addition of antigen presenting cells is also termed restimulation, since in these steps the already activated T lymphocytes receive an additional stimulus for further proliferation. In certain embodiments the antigen presenting cells are added once. In other embodiments, the antigen presenting cells are added twice. In another embodiment, the antigen presenting cells are added three times. Further embodiments relate to methods in which the antigen presenting cells are added three or more times. The new APC can be added to the T cell cultures every 7 to 21 days, or every 12 to 16 days, or every 13 to 15 days, or every 14 days. The skilled person understands that the cells are provided with fresh culture medium on a regular basis that contains supplementary cytokines.

Exposing the cell population comprising T lymphocytes to the antigen presenting cells in vitro means that the exposure occurs not in an organism, such as a mammal, but the exposure takes place in in vitro cell culture. The cell culture conditions are known to the skilled person and comprise addition of cytokines, for example IL-2, IL-4, IL-7 and/or IL-15 among others, depending on the type of the T cell which is generated (Schendel, D J. et al. Human CD8+T lymphocytes. 1997. In: The Immunology Methods Manual. (I. Lefkovits, Ed.) pp 670-690.; Regn, S., et al. 2001. The generation of monospecific and bispecific anti-viral cytotoxic T lymphocytes (CTL) for the prophylaxis of patients receiving an allogeneic bone marrow transplant. Bone Marrow Transplant. 27: 53-64; Su, Z. et al. Antigen presenting cells transfected with LMP2a RNA induce CD4+ LMP2a-specific cytotoxic T lymphocytes which kill via a Fas-independent mechanism. Leuk. Lymphoma 43(8): 1651-62.).

In some embodiments, the method may further comprise the step of enrichment of activated and/or antigen specific T lymphocytes. This enrichment step typically comprises the following steps:
(a) contacting the cell population comprising activated antigen-specific T lymphocytes with at least one binding molecule which specifically binds to a marker protein specifically expressed by activated T lymphocytes or with at least one MHC molecule presenting an epitope of the desired antigen;
(b) isolating T lymphocytes to which the at least one binding molecule or the at least one MHC molecule presenting an epitope of the desired antigen is bound.

In particular embodiments, the method may comprise the step of enrichment of activated T lymphocytes. This enrichment step typically comprises the following steps:
(a) contacting the cell population comprising activated antigen-specific T lymphocytes with at least one binding molecule which specifically binds to a marker protein specifically expressed by activated T lymphocytes;
(b) isolating T lymphocytes to which the at least one binding molecule is bound.

In other specific embodiments, the method may comprise the step of enrichment of T lymphocytes which are specific for the desired antigen. This enrichment step typically comprises the following steps:
(a) contacting the cell population comprising activated antigen-specific T lymphocytes with a MHC molecule presenting an epitope of the desired antigen;
(b) isolating T lymphocytes to which the at least one MHC molecule presenting an epitope of the desired antigen is bound.

The enrichment of activated T lymphocytes based on marker proteins specifically expressed by activated T lymphocytes allows to enrich for a broad spectrum of activated T cells independent of the restriction and the specific epitope.

The binding molecule which specifically binds to the marker protein may without limitation be an antibody, a derivative of an antibody, a fragment of an antibody, or a conjugate of the aforementioned with a further molecule. The binding protein may be labeled, for example in order to facilitate sorting procedures, such as FACS or MACS.

The marker protein specifically expressed by activated T lymphocytes, may be any surface protein or secreted protein that is expressed by activated T lymphocytes and is substantially not expressed by non-activated T lymphocytes. In preferred embodiments, the at least one marker protein specifically expressed by activated T lymphocytes is selected from the group comprising Ox40, CD137, CD40L, PD-1, IL-2 receptor, interferon γ, IL-2, GM-CSF and TNF-α. Using these markers allows the enrichment of activated T lymphocytes independent from the specific epitope presented by the TCR. This method facilitates the isolation of T cells recognizing all potential immunogenic epitopes of a selected antigen and is, for example, particularly useful, for poorly defined antigens.

In the enrichment step the selected cells can be pooled into subpopulations or directly isolated as single cell clones. In specific embodiments the cells are in a first enrichment step pooled and in a further enrichment step separated into single clones. Single clone separation may occur without limitation via limited dilution or automated single cell sorting employing FACS or MACS. Preferably single cell sorting is carried out by FACS.

In specific embodiments selecting activated CD4 T cells comprises the following steps:

(a1) contacting the antigen presenting cells expressing at least one fusion protein of step A) with an antibody against CD40 in order to block the interaction between CD40-CD40L of the antigen presenting cells and the antigen-specific T lymphocytes and to accumulate CD40L at the surface of T lymphocytes;
(a2) contacting the cell population comprising activated antigen-specific T lymphocytes with an anti-CD40L antibody;
(b) isolating the T lymphocytes marked with an anti-CD40L antibody and an anti-CD4 antibody.

In order to employ the selection of activated T cells by secreted proteins, for example cytokines like interferon-γ, bi-specific molecules recognizing T-cell surface markers and targeted cytokines capture the secreted cytokine at the cell surface which then can be detected by a labeled detection antibody as described in Becker et al. (Becker, C et al. 2001. Adoptive tumor therapy with T lymphocytes enriched through an IFN capture assay. Nature Med. 7(10): 1159-1162.).

In addition, in step (a) the cells may be further contacted with a binding molecule that specifically binds to CD4 and/or with a binding molecule that specifically binds to CD8.

Alternatively, the enrichment may be carried out by employing MHC molecules presenting an epitope of the desired antigen (i.e. the antigen exogenously expressed by the antigen presenting cell of step A). The MHC molecules may be labeled, for example in order to facilitate sorting procedures, such as FACS or MACS. The low affinity interaction between TCR and corresponding peptide:MHC complexes can be overcome by the assembly of soluble multimers of peptide:MHC molecules as described in Wilde et al. (Dendritic cells pulsed with RNA encoding allogeneic MHC and antigen induce T cells with superior antitumor activity and higher TCR functional avidity. Blood 114(10): 2131-2139; 2009) such as, without limitation, dimers, trimers, tetramers, pentamers, hexamers, heptamers or octamers. Further, so called peptid:MHC streptamers can be employed which bind reversibly to TCRs and thus allow the isolation of high affinity TCRs without the risk of inducing functional changes or activation induced cell death (Knabel et al. (2002) Reversible MHC multimer staining for functional isolation of T-cell populations and effective adoptive transfer. Nature Medicine, 8(6), 631-7.). The reversible properties of T cell:streptamer interaction is based on a modified form of streptavidin (strep-tactin) which acts as the backbone of the streptamer.

This approach allows the targeted enrichment of epitope specific TCRs with a specific restriction.

The isolation of the activated and/or antigen-specific T lymphocytes may be carried out by fluorescence-activated cell sorting (FACS) as well as magnetic-activated cell sorting (MACS). For FACS the binding molecule specifically binding to the marker protein or the MHC molecule presenting an epitope of the desired antigen is labeled with a fluorescent dye. FACS is particular useful for the isolation of small numbers with high purity. For MACS the binding molecule specifically binding to the marker protein or the MHC molecule presenting an epitope of the desired antigen is labeled with a magnetic particle, such as a magnetic bead. MACS is particularly suited for the fast sorting of bulk cultures.

In addition, in step (a) the cells may be further contacted with a binding molecule that specifically binds to CD4 to further enrich for CD4 and/or with a binding molecule that specifically binds to CD8.

Another embodiment refers to the method according to any one of the preceding claims, wherein the method further comprises the step C2) identification of antigen-specific T lymphocytes, comprising the following steps:
a) incubation of expanded cell clones of the cell population comprising activated antigen-specific T lymphocytes with
  (i) antigen presenting cells as defined in step A), and
  (ii) control antigen presenting cells;
b) comparison of the activation profile of the incubation with (i) and (ii) for each cell clone;
c) identification of antigen-specific cell clones based on the comparison of b);
wherein the activation by (i) but not by (ii) indicates that the cell clone is antigen-specific.

The step C2) identification of antigen-specific T lymphocytes may be carried out after the step C1) enrichment of activated T lymphocytes or alternatively may be carried out after step B) exposing the cell population comprising T lymphocytes to the antigen presenting cells without the enrichment step C1).

A further embodiment refers to the method according to any one of the preceding claims, wherein the method further comprises the step
C2) identification of antigen-specific T lymphocytes, comprising the following steps:
a) incubation of at least one fraction of cells of the cell population comprising activated antigen-specific T lymphocytes with
  (i) antigen presenting cells as defined in step A), and
  (ii) control antigen presenting cells or in the absence of antigen presenting cells;
b) comparison of the activation profile of the incubation with (i) and (ii) for the at least one fraction of cells;
c) identification of a fraction of cells which is antigen-specific based on the comparison of b);
wherein the activation by (i) but not by (ii) indicates that the fraction of cells is antigen-specific.

Another embodiment refers to the method according to any one of the preceding claims, wherein the method further comprises the step
C2) identification of antigen-specific T lymphocytes, comprising the following steps:
a) incubation of expanded T cell clones of the cell population comprising activated antigen-specific T lymphocytes with
  (i) antigen presenting cells as defined in step A), and
  (ii) control antigen presenting cells or in the absence of antigen presenting cells;
b) comparison of the activation profile of the incubation with (i) and (ii) for each cell clone;
c) identification of antigen-specific cell clones based on the comparison of b);
wherein the activation by (i) but not by (ii) indicates that the cell clone is antigen-specific.

The activation profile of the T lymphocytes can be determined for example by measuring activation-induced cytokine release or antigen-directed killing capacity.

To measure activation-induced cytokine secretion, T cells may be co-cultured with antigen-loaded APCs. Different effector cell to target cell (E:T) ratios may be employed. T cells incubated with control antigen presenting, i.e. mock-transfected APCs, or in the absence of stimulating cells may be used as negative controls. The culture supernatants are assessed by a standard enzyme-linked immunosorbent assay (ELISA). Examples for markers are, without limitation, granulocyte-macrophage colony-stimulating factor (GM-CSF), interferon-γ (IFN-γ), IL-2 and TNF-α secretion. IFN- γ, IL-2 and TNF-α secretion upon antigen encounter correlates with enhanced anti-tumor function and is therefore particularly useful when measuring antigen-induced cytokine secretion of CD8$^+$ cytotoxic T cells. Additionally, IFN-γ and granulocyte-macrophage colony-stimulating factor (GM-CSF) are well-defined cytokines for the assessment of antigen-specific CD4$^+$ T helper-1 (Th1)-polarized T cell clones.

If multiple antigens are used concurrently for primary T cell induction, individual APC populations expressing each priming antigen may be mixed in equal proportions and used in T cell co-cultures. Therefore, the initial screening assays performed to assess specificity only allow prediction of the overall antigen-reactivity with respect to the total deployed target antigens. The assessment of single-antigen specificities requires the subsequent co-culture of antigen-reactive T cells with single-species ivtRNA-transfected APCs.

Further the cytotoxic activity of individual T cell clones may be measured for example by chromium release assays. In such assays, target cells are labeled with radioactive chromium and exposed to T cells. Upon killing, radioactive chromium is released into the supernatant and detectable within 4 hours after the start of the co-culture. Specific chromium release is normalized to spontaneous release assessed by incubating target cells in the absence of effector cells. Accordingly, high amounts of chromium in the supernatant correlate with excellent cytolytic T cell activity. Chromium release assays are preferably performed to screen for tumor antigen-specific CD8$^+$ T cells.

Antigen presenting cells suitable for the use in the identification of antigen-specific T lymphocytes may be for example tumor cell lines expressing the desired antigen and the required MHC molecules, established antigen presenting cell lines expressing common MHC molecules, or antigen presenting cells derived from the same donor as the population comprising T lymphocytes.

One example of a established antigen presenting cell line is the human lymphoid T2 cell line expressing the frequent HLA-A*02:01 allele, which exhibits defective intrinsic epitope presentation and can be externally loaded with short peptides, for example synthetic peptides: This cell line can be used for screening of HLA-A*02:01-restricted CD8$^+$ T lymphocytes. Another example is the human K562 cell line, lacking HLA class I and II expression in which any HLA molecule of interest can be stably or transiently introduced and therefore can serve both for CD8$^+$ T lymphocyte and CD4$^+$ T lymphocyte screening.

Donor derived antigen presenting cells may be for example isolated monocytes which are maturated to dendritic cells. Maturated dendritic cells exhibit optimal activation capacity.

A further example for useful donor-derived APCs are Epstein-Barr virus (EBV)-immortalized B lymphocytes, so called lymphoblastoid cell lines (LCL). Since LCLs naturally originate from B cells, these APCs feature proficient function in antigen processing and presentation. Furthermore, LCLs express co-stimulatory molecules like B7.1 (CD80) and B7.2 (CD86) as well as appropriate adhesion molecules that help to enhance their stimulatory capacity. Genome-reduced mutant EBV (mini-EBV) strains can be used to generate mini-EBV-transformed B cells (mLCL) that lack most of the lytic cycle genes, consequently reducing EBV-dependent activation of T lymphocytes (Kempkes, B. et al. (1995) Immortalization of human B lymphocytes by a plasmid containing 71 kilobase pairs of Epstein-Barr virus DNA. J Virol 69(1): 231-238, 1995; Moosmann, et al. (2002) B cells immortalized by a mini-Epstein-Barr virus encoding a foreign antigen efficiently reactivate specific cytotoxicT cells. Blood 100(5): 1755-1764).

Donor-derived LCL/mLCL may be used to assess T cell specificity, particularly when large numbers of isolated T cell clones need to be evaluated. Antigen loading of LCL/mLCL may be accomplished by for example by retroviral transduction ivtRNA transfection and external peptide or protein supply.

The isolation of the antigen-specific T lymphocytes is based on the comparison of the activation profile of the T lymphocytes incubated (i) with antigen presenting cells expressing the desired antigen and (ii) with control antigen presenting cells or in the absence of antigen presenting cells.

The activation by (i) antigen presenting cells expressing the desired antigen and not by (ii) control antigen presenting cells or in the absence of antigen presenting cells indicates that the T cell clone is antigen-specific. Activated in comparison to not activated means that there is a reduction of at least 30%, of at least 40%, of at least 50%, of at least 60%, of a least 70%, of at least 80% of the value (i.e. IFN-γ secretion) of the T lymphocytes incubated with antigen presenting cells expressing the desired antigen.

The ER translocation signal sequence may be derived from an endosomal/lysosomal associated protein.

The ER-translocation signal sequence used in the disclosed method may be the sorting sequence of an endosomal/lysosomal localized protein. Endosomal/lysosomal localized proteins as used herein refer to proteins which are localized in the membrane or the lumen of the endosomes and/or the lysosomes of a cell.

Examples for endosomal or lysosomal localized proteins are glycosidases such as, alpha-galactosidase A/GLA, endo-beta-N-acetylglucosaminidase H/Endo H, alpha-N-acetylgalactosaminidase/NAGA, galactosylceramidase/GALC, alpha-N-acetylglucosaminidase/NAGLU, glucosylceramidase/GBA, alpha-galactosidase/a-Gal, heparanase/HPSE, alpha-L-fucosidase, heparinase I, tissue alpha-L-fucosidase/FUCA1, heparinase II, beta-galactosidase-1/GLB1, heparinase III, beta-glucuronidase/GUSB, hexosaminidase A/HEXA, beta (1-3)-galactosidase, hyaluronan Lyase, beta (1-4)-galactosidase, hyaluronidase 1/HYAL1, chitinase 3-like 1, hyaluronidase 4/HYAL4, chitinase 3-like 2, alpha-L-iduronidase/IDUA, chitinase 3-like 3/ECF-L, chitobiase/CTBS, chitotriosidase/CHIT1, lactase-like protein/LCTL, chondroitin B Lyase/chondroitinase B, lysosomal alpha-glucosidase, chondroitinase ABC, MBD4, chondroitinase AC, NEU-1/Sialidase-1, cytosolic beta-glucosidase/GBA3, O-GlcNAcase/OGA, endo-beta-N-acetylglucosaminidase F1/Endo F1, PNGase F, endo-beta-N-acetylglucosaminidase F3/Endo F3, SPAM1; lysosomal proteases such as, AMSH/STAMBP, cathepsin H, cathepsin 3, cathepsin K, cathepsin 6, cathepsin L, cathepsin 7/cathepsin 1, cathepsin 0, cathepsin A/lysosomal carboxypeptidase A, cathepsin S, cathepsin B, cathepsin V, cathepsin C/DPPI, cathepsin X/Z/P, cathepsin D, galactosylceramidase/GALC, cathepsin F, öegumain/asparaginyl endopeptidase; sulfatases such as arylsulfatase A/ARSA, iduronate 2-sulfatase/IDS, arylsulfatase B/ARSB, N-acetylgalactosamine-6-sulfatase/GALNSv, arylsulfatase G/ARSG, sulfamidase/SGSH, glucosamine (N-acetyl)-6-sulfatase/GNS, sulfatase-2/SULF2; or other lysosomal proteins such as BAD-LAMP/LAMP5; hyaluronidase 1/HYAL1; CD63; LAMP1/CD107a; CD-M6PR; LAMP2/CD107b; clathrin Heavy Chain 1/CHC17; Rab27a; clathrin Heavy Chain 2/CHC22; UNC13D, CD68, CD1b or DC-LAMP.

The ER translocation signal sequence is derived from an endosomal/lysosomal associated protein. The endosomal/ lysosomal associated protein may be LAMP1, LAMP2, DC-LAMP, CD68 or CD1b, preferably LAMP1. Preferably, the ER translocation signal is human. The ER translocation signal sequence may comprise the sequence of at least one of SEQ ID NO: 33, SEQ ID NO: 40, SEQ ID NO: 42, SEQ ID NO: 44 and SEQ ID NO: 46. In some embodiments the ER translocation signal sequence may consist of one of the sequences selected from the group consisting of SEQ ID NO: 34, SEQ ID NO: 41, SEQ ID NO: 43, SEQ ID NO: 45, SEQ ID NO: 47. In specific embodiments the ER translocation signal sequence comprises the sequence SEQ ID NO: 33 or a fragment thereof. In more specific embodiments the ER translocation signal sequence consists of the following sequence SEQ ID NO: 34.

The endosomal/lysosomal targeting sequence may be derived from LAMP1 or DC-LAMP, preferably DC-LAMP. The endosomal/lysosomal targeting sequence is typically a part of a transmembrane and cytoplasmic domain. Thus, the transmembrane and cytoplasmic domain comprising an endosomal/lysosomal targeting sequence may be derived from LAMP1 or DC-LAMP, preferably DC-LAMP. Preferably the transmembrane and cytoplasmic domain comprising an endosomal/lysosomal targeting sequence is human. Typically the endosomal/lysosomal targeting sequence comprises the motif Y-XX followed by a hydrophobic amino acid. Preferably, the endosomal/lysosomal targeting signal sequence is YQRI. The transmembrane and cytoplasmic domain comprising an endosomal/lysosomal targeting sequence may comprise the sequence SEQ ID NO: 54 or a fragment thereof. For example, the transmembrane and cytoplasmic domain comprising an endosomal/lysosomal targeting sequence may comprise the sequence SEQ ID NO: 35 or a fragment thereof.

The term hydrophobic amino acid is well known to the skilled person. Examples for hydrophobic amino acids are Ala, Ile, Leu, Phe, Val, Pro, Gly, Met, Trp, Tyr, Pro, Cys.

Typically, the antigen presenting cells are selected from dendritic cells, activated B cells, monocytes, macrophages, EBV-transformed lymphoblastoid cell lines, preferably dendritic cells, more preferably monocyte derived dendritic cells.

The antigen presenting cells may comprise different populations of antigen presenting cells, each population expressing a different antigen fusion protein.

In some embodiments, the antigen presenting cells are mature dendritic cells generated by a method comprising the following steps: i) provision of monocytes; ii) incubation of the monocytes of step i) with IL-4 and GM-CSF; iii) incubation of the monocytes of step ii) with IL-4 and GM-CSF in combination with a maturation cocktail. The maturation cocktail may comprise at least one of the components selected from the group consisting of IL-B, TNF-α, INF-γ, TLR7/8 agonist, PGE2 and TLR3 agonist or a combination thereof. For example, the TLR7/8 agonist may be R848 and/or the TLR3 agonist may be poly(I:C). The incubation of step ii) may last for at least 2 days. The incubation of step iii) may last for at least 12 hours, preferably 24 hours.

Usually, the cell population comprising T lymphocytes is a population of peripheral blood lymphocytes. The cell population comprising T lymphocytes may be a population of unseparated peripheral blood lymphocytes. The cell population may be enriched for T lymphocytes, preferably CD8$^+$ and/or CD4$^+$ T lymphocytes.

A further aspect of the invention refers to an expression vector comprising:

a human endoplasmatic reticulum (ER)-translocation signal sequence, and a human transmembrane and cytoplasmic domain comprising an endosomal/lysosomal targeting sequence.

The vector may comprise a promotor for in vitro mRNA transcription. The ER translocation signal sequence is derived from an endosomal/lysosomal associated protein, for example LAMP1, LAMP2, DC-LAMP, CD68, CD1b, preferably LAMP1. Preferably, the ER translocation signal is human. In specific embodiments the ER translocation signal comprises the sequence SEQ ID NO: 33 or a fragment thereof. In more specific embodiments the ER translocation signal consists of the following sequence SEQ ID NO: 34.

The endosomal/lysosomal targeting sequence may be derived from LAMP1 or DC-LAMP, preferably DC-LAMP. The endosomal/lysosomal targeting sequence is typically a part of a transmembrane and cytoplasmic domain. Thus, the transmembrane and cytoplasmic domain comprising an endosomal/lysosomal targeting sequence may be derived from LAMP1 or DC-LAMP, preferably DC-LAMP. Preferably the transmembrane and cytoplasmic domain comprising an endosomal/lysosomal targeting sequence is human. Typically the endosomal/lysosomal targeting sequence comprises the motif Y-XX followed by a hydrophobic amino acid (X stands for any natural occurring amino acid). Preferably, the endosomal/lysosomal targeting signal is YQRI. The transmembrane and cytoplasmic domain comprising an endosomal/lysosomal targeting sequence may comprise the sequence SEQ ID NO: 54 or a fragment thereof. For example, the transmembrane and cytoplasmic domain comprising an endosomal/lysosomal targeting sequence may comprise the sequence SEQ ID NO: 35 or a fragment thereof.

In some embodiments the expression vector further comprises restriction sites between the ER translocation signal and the human transmembrane and cytoplasmic domain comprising an endosomal/lysosomal targeting sequence. In other embodiments, the vector further comprises at least one antigen, or a fragment thereof which is inserted between human endoplasmatic reticulum (ER)-translocation signal, and the human transmembrane and cytoplasmic domain comprising an endosomal/lysosomal targeting sequence.

In specific embodiments, the vector comprises a sequence encoding at least two antigens or fragments thereof. The vector may comprise a sequence encoding at least three, at least 4, at least 5, at least 6, at least 7, at least 8, at least 9, at least 10 antigens or fragments thereof. The vector may comprise a sequence encoding less than 100, less than 50, less than 40, less than 30, less than 20, less than 10 antigens or fragments thereof.

In some embodiments the vector comprises a nucleic acid sequence encoding a full length amino acid sequence of an antigen. Alternatively, the vector comprises a fragment of a nucleic acid sequence encoding an amino acid sequence of an antigen. As shown in FIG. 12, antigen presenting cells in which a vector comprising fragments of two different antigens has been introduced can induce activation of different TCRs specific for the two antigens.

Typically, the antigen is a tumor antigen or a viral antigen. The tumor antigen may be selected from the group consisting of viral tumor antigen, tumor-specific antigen, tumor associated antigen and an antigen carrying patient specific mutations and being expressed in tumor cells of the patient.

Viral tumor antigens also termed oncogenic viral antigens are antigens of oncogenic viruses, such as the oncogenic DNA viruses for example viruses, such as hepatitis B viruses, herpesviruses, and papillomaviruses and oncogenic RNA viruses. Tumor specific antigens refer to tumor associated mutations which are exclusively expressed by tumor cells. The group of tumor associated antigens comprises for example tissue specific cancer/testis antigens or tissue differentiation antigens such as MART-1, Tyrosinase or CD20. Preferably the tumor antigen is a tumor associated antigen, more preferably the tumor associated antigen is a cancer/testis antigen (C/T antigen). The C/T antigen may be selected from the group comprising MAGE family members, for example MAGE-A1, MAGE-A3, MAGE-A4, but not limited to these, tumor antigens comprising single point mutations, NY-ESO1, tumor/testis-antigen 1B, GAGE-1, SSX-4, XAGE-1, BAGE, GAGE, SCP-1, SSX-2, SSX-4, CTZ9, CT10, SAGE and CAGE. Preferably the C/T antigen may be selected from the group consisting of GAGE-1, SSX-4 and XAGE-1. Preferably the antigen carrying patient specific mutations and being expressed in tumor cells of the patient is not expressed in non-cancerous cells of the patient.

Another aspect of the invention refers to an antigen presenting cell, in particular dendritic cell, expressing at least one fusion protein comprising
  at least one antigen or a fragment thereof,
  an endoplasmatic reticulum (ER)-translocation signal sequence preceding the N-terminus of the antigen, and
  a transmembrane and cytoplasmic domain comprising an endosomal/lysosomal targeting sequence following the C-terminus of the antigen.

Another aspect of the invention refers to the use of the expression vector as described herein for in vitro generation of antigen-specific T lymphocytes.

A further aspect of the invention refers to T-lymphocytes for use in a method of preventing or treating cancer comprising administering to a mammal the T-lymphocytes generated by methods as described herein.

Another aspect refers to a method for generating an antigen-specific TCR comprising steps of the methods described above and further comprising the step of isolating a TCR from the activated antigen-specific lymphocyte generated by the methods as described herein.

The isolation of the TCR and the subsequent sequence analysis is for example described in Steinle et al. (In vivo expansion of HLA-B35 alloreactive T cells sharing homologous T cell receptors: evidence for maintenance of an oligoclonally dominated allospecificity by persistent stimulation with an autologous MHC/peptide complex. The Journal of Experimental Medicine, 181(2), 503-13; 1995). The sequence analysis may be carried out for example by PCR or by next generation sequencing methods. Methods for identifying the sequence of a nucleic acid are well known to those skilled in the art.

The TCR is composed of two different protein chains, a and b. The TCR α chain comprises variable (V), joining (J) and constant (C) regions. The TCR α chain comprises variable (V), diversity (D), joining (J) and constant (C) regions. The rearranged V(D)J regions of both the TCR α and the TCR β chain contain hypervariable regions (CDR, complementarity determining regions), among which the CDR3 region determines the specific epitope recognition.

One aspect of the invention refers to a TCR specific for GAGE-1. In one embodiment the TCR specific for GAGE-1 specifically recognizes at least one of the amino acid sequences selected from the group consisting of SEQ ID NO: 48 and SEQ ID NO:49 or fragments thereof. The fragment may have a length of at least 9, at least 10, at least 11, at least 12, at least 13, at least 14, at least 15 or more amino acids. The TCR may specifically bind to at least one of the amino acid sequences selected from the group consisting of SEQ ID NO: 48 and SEQ ID NO:49 or fragments thereof.

The TCR specific for GAGE-1 may comprise a TCR α chain having an amino acid sequence which is at least 50%, at least 60%, at least 70%, at least 80%, at least 85%, at least 90%, at least 95%, at least 96%, at least 97%, at least 98%, at least 99% identical to SEQ ID No: 7 and a TCR β chain having an amino acid sequence which is at least 50%, at least 60%, at least 70%, at least 80%, at least 85%, at least 90%, at least 95%, at least 96%, at least 97%, at least 98%, at least 99% identical to SEQ ID No: 8.

Certain embodiments relate to a TCR receptor specific for GAGE-1 comprising a TCR α chain having the amino acid sequence of SEQ ID No: 7 and a TCR β chain comprising the amino acid sequence of SEQ ID No: 8.

Further, the application is related to a TCR receptor specific for GAGE-1 comprising a TCR α chain and a TCR β chain, wherein
  the TCR α chain comprises an amino acid sequence which is at least 80% identical to SEQ ID No: 7 and comprises a CDR3 having the sequence of SEQ ID No: 3;
  the TCR β chain comprises an amino acid sequence which is at least 80% identical to SEQ ID No: 8 and comprises a CDR3 having the sequence of SEQ ID No: 4.

Certain embodiments relate to a TCR receptor specific for GAGE-1 comprising TCR α chain and a TCR β chain, wherein
  the TCR α chain comprises an amino acid sequence which is at least 50%, at least 60%, at least 70%, at least 80%, at least 85%, at least 90%, at least 95%, at least 96%, at least 97%, at least 98%, at least 99% identical to SEQ ID No: 7 and comprises a CDR3 having the sequence of SEQ ID No: 3;
  the TCR β chain comprises an amino acid sequence which is at least 50%, at least 60%, at least 70%, at least 80%, at least 85%, at least 90%, at least 95%, at least 96%, at least 97%, at least 98%, at least 99% identical to SEQ ID No: 8 and comprises a CDR3 having the sequence of SEQ ID No: 4.

Certain embodiments refer to a TCR receptor specific for GAGE-1 comprising a TCR α chain encoded by a nucleotide sequence which is at least 50%, at least 60%, at least 70%, at least 80%, at least 85%, at least 90%, at least 95%, at least 96%, at least 97%, at least 98%, at least 99% identical to SEQ ID No: 5 and a TCR β chain encoded by a nucleotide sequence which is at least 50%, at least 60%, at least 70%, at least 80%, at least 85%, at least 90%, at least 95%, at least 96%, at least 97%, at least 98%, at least 99% identical to SEQ ID No: 6.

Certain embodiments relate to a TCR receptor specific for GAGE-1 comprising a TCR α chain encoded by the nucleotide sequence SEQ ID No: 5 and a TCR β chain encoded by the nucleotide sequence SEQ ID No: 6.

Further, the application is related to a TCR receptor specific for GAGE-1 comprising a TCR α chain and a TCR β chain, wherein
  the TCR α chain is encoded by a nucleotide sequence which is at least 80% identical to SEQ ID No: 5 and comprises a CDR3 region encoded by the nucleotide sequence set out in SEQ ID No: 1;
  the TCR β chain is encoded by a nucleotide sequence which is at least 80% identical to SEQ ID No: 6 and comprises a CDR3 region encoded by the nucleotide sequence set out SEQ ID No: 2.

Certain embodiments relate to a TCR receptor specific for GAGE-1 comprising TCR α chain and a TCR β chain, wherein
the TCR α chain is encoded by a nucleotide sequence which is at least 50%, at least 60%, at least 70%, at least 80%, at least 85%, at least 90%, at least 95%, at least 96%, at least 97%, at least 98%, at least 99% identical to SEQ ID No: 5 and comprises a CDR3 region encoded by the nucleotide sequence set out in SEQ ID No: 1;
the TCR β chain is encoded by a nucleotide sequence which is at least 50%, at least 60%, at least 70%, at least 80%, at least 85%, at least 90%, at least 95%, at least 96%, at least 97%, at least 98%, at least 99% identical to SEQ ID No: 6 and comprises a CDR3 region encoded by the nucleotide sequence set out in SEQ ID No: 2.

Another aspect of the application refers to a TCR specific for SSX-4 comprising a TCR α chain having an amino acid sequence which is at least 50%, at least 60%, at least 70%, at least 80%, at least 85%, at least 90%, at least 95%, at least 96%, at least 97%, at least 98%, at least 99% identical to SEQ ID No: 15 and a TCR β chain having an amino acid sequence which is at least 50%, at least 60%, at least 70%, at least 80%, at least 85%, at least 90%, at least 95%, at least 96%, at least 97%, at least 98%, at least 99% identical to SEQ ID No: 16.

Certain embodiments relate to a TCR receptor specific for SSX-4 comprising a TCR α chain having the amino acid sequence of SEQ ID No: 15 and a TCR β chain comprising the amino acid sequence of SEQ ID No: 16.

Further, the application is related to a TCR receptor specific for SSX-4 comprising a TCR α chain and a TCR β chain, wherein
the TCR α chain comprises an amino acid sequence which is at least 80% identical to SEQ ID No: 15 and comprises a CDR3 having the sequence of SEQ ID No: 11;
the TCR β chain comprises an amino acid sequence which is at least 80% identical to SEQ ID No: 16 and comprises a CDR3 having the sequence of SEQ ID No: 12.

Certain embodiments relate to a TCR receptor specific for SSX-4 comprising TCR α chain and a TCR β chain, wherein
the TCR α chain comprises an amino acid sequence which is at least 50%, at least 60%, at least 70%, at least 80%, at least 85%, at least 90%, at least 95%, at least 96%, at least 97%, at least 98%, at least 99% identical to SEQ ID No: 15 and comprises a CDR3 having the sequence of SEQ ID No: 11;
the TCR β chain comprises an amino acid sequence which is at least 50%, at least 60%, at least 70%, at least 80%, at least 85%, at least 90%, at least 95%, at least 96%, at least 97%, at least 98%, at least 99% identical to SEQ ID No: 16 and comprises a CDR3 having the sequence of SEQ ID No: 12.

Certain embodiments refer to a TCR receptor specific for SSX-4 comprising a TCR α chain encoded by a nucleotide sequence which is at least 50%, at least 60%, at least 70%, at least 80%, at least 85%, at least 90%, at least 95%, at least 96%, at least 97%, at least 98%, at least 99% identical to SEQ ID No: 13 and a TCR β chain encoded by a nucleotide sequence which is at least 50%, at least 60%, at least 70%, at least 80%, at least 85%, at least 90%, at least 95%, at least 96%, at least 97%, at least 98%, at least 99% identical to SEQ ID No: 14.

Certain embodiments relate to a TCR receptor specific for SSX-4 comprising a TCR α chain encoded by the nucleotide sequence SEQ ID No: 13 and a TCR β chain encoded by the nucleotide sequence SEQ ID No: 14.

Further, the application is related to a TCR receptor specific for SSX-4 comprising a TCR α chain and a TCR β chain, wherein
the TCR α chain is encoded by a nucleotide sequence which is at least 80% identical to SEQ ID No: 13 and comprises a CDR3 region encoded by the nucleotide sequence set out in SEQ ID No: 9;
the TCR β chain is encoded by a nucleotide sequence which is at least 80% identical to SEQ ID No: 14 and comprises a CDR3 region encoded by the nucleotide sequence set out SEQ ID No: 10.

Certain embodiments relate to a TCR receptor specific for SSX-4 comprising TCR α chain and a TCR β chain, wherein
the TCR α chain is encoded by a nucleotide sequence which is at least 50%, at least 60%, at least 70%, at least 80%, at least 85%, at least 90%, at least 95%, at least 96%, at least 97%, at least 98%, at least 99% identical to SEQ ID No: 13 and comprises a CDR3 region encoded by the nucleotide sequence set out in SEQ ID No: 9;
the TCR β chain is encoded by a nucleotide sequence which is at least 50%, at least 60%, at least 70%, at least 80%, at least 85%, at least 90%, at least 95%, at least 96%, at least 97%, at least 98%, at least 99% identical to SEQ ID No: 14 and comprises a CDR3 region encoded by the nucleotide sequence set out in SEQ ID No: 10.

One aspect of the invention refers to a TCR specific for XAGE-1. In one embodiment the TCR specific for XAGE-1 specifically recognizes at least one of the amino acid sequences selected from the group consisting of SEQ ID NO: 50 and SEQ ID NO: 51 or fragments thereof. The fragment may have a length of at least 9, at least 10, at least 11, at least 12, at least 13, at least 14, at least 15 or more amino acids. The TCR may specifically bind to at least one of the amino acid sequences selected from the group consisting of SEQ ID NO: 50 and SEQ ID NO: 51 or fragments thereof.

The TCR specific for XAGE-1 may comprise a TCR α chain having an amino acid sequence which is at least 50%, at least 60%, at least 70%, at least 80%, at least 85%, at least 90%, at least 95%, at least 96%, at least 97%, at least 98%, at least 99% identical to SEQ ID No: 23 and a TCR β chain having an amino acid sequence which is at least 50%, at least 60%, at least 70%, at least 80%, at least 85%, at least 90%, at least 95%, at least 96%, at least 97%, at least 98%, at least 99% identical to SEQ ID No: 24.

Certain embodiments relate to a TCR receptor specific for XAGE-1 comprising a TCR α chain having the amino acid sequence of SEQ ID No: 23 and a TCR β chain comprising the amino acid sequence of SEQ ID No: 24.

Further, the application is related to a TCR receptor specific for XAGE-1 comprising a TCR α chain and a TCR β chain, wherein
the TCR α chain comprises an amino acid sequence which is at least 80% identical to SEQ ID No: 23 and comprises a CDR3 having the sequence of SEQ ID No: 19;
the TCR β chain comprises an amino acid sequence which is at least 80% identical to SEQ ID No: 24 and comprises a CDR3 having the sequence of SEQ ID No: 20.

Certain embodiments relate to a TCR receptor specific for XAGE-1 comprising TCR α chain and a TCR β chain, wherein
  the TCR α chain comprises an amino acid sequence which is at least 50%, at least 60%, at least 70%, at least 80%, at least 85%, at least 90%, at least 95%, at least 96%, at least 97%, at least 98%, at least 99% identical to SEQ ID No: 23 and comprises a CDR3 having the sequence of SEQ ID No: 19;
  the TCR β chain comprises an amino acid sequence which is at least 50%, at least 60%, at least 70%, at least 80%, at least 85%, at least 90%, at least 95%, at least 96%, at least 97%, at least 98%, at least 99% identical to SEQ ID No: 24 and comprises a CDR3 having the sequence of SEQ ID No: 20.

Certain embodiments refer to a TCR receptor specific for XAGE-1 comprising a TCR α chain encoded by a nucleotide sequence which is at least 50%, at least 60%, at least 70%, at least 80%, at least 85%, at least 90%, at least 95%, at least 96%, at least 97%, at least 98%, at least 99% identical to SEQ ID No: 21 and a TCR β chain encoded by a nucleotide sequence which is at least 50%, at least 60%, at least 70%, at least 80%, at least 85%, at least 90%, at least 95%, at least 96%, at least 97%, at least 98%, at least 99% identical to SEQ ID No: 22.

Certain embodiments relate to a TCR receptor specific for XAGE-1 comprising a TCR α chain encoded by the nucleotide sequence SEQ ID No: 21 and a TCR β chain encoded by the nucleotide sequence SEQ ID No: 22.

Further, the application is related to a TCR receptor specific for XAGE-1 comprising a TCR α chain and a TCR β chain, wherein
  the TCR α chain is encoded by a nucleotide sequence which is at least 80% identical to SEQ ID No: 21 and comprises a CDR3 region encoded by the nucleotide sequence set out in SEQ ID No: 17;
  the TCR β chain is encoded by a nucleotide sequence which is at least 80% identical to SEQ ID No: 22 and comprises a CDR3 region encoded by the nucleotide sequence set out SEQ ID No: 18.

Certain embodiments relate to a TCR receptor specific for XAGE-1 comprising TCR α chain and a TCR β chain, wherein
  the TCR α chain is encoded by a nucleotide sequence which is at least 50%, at least 60%, at least 70%, at least 80%, at least 85%, at least 90%, at least 95%, at least 96%, at least 97%, at least 98%, at least 99% identical to SEQ ID No: 21 and comprises a CDR3 region encoded by the nucleotide sequence set out in SEQ ID No: 17;
  the TCR β chain is encoded by a nucleotide sequence which is at least 50%, at least 60%, at least 70%, at least 80%, at least 85%, at least 90%, at least 95%, at least 96%, at least 97%, at least 98%, at least 99% identical to SEQ ID No: 22 and comprises a CDR3 region encoded by the nucleotide sequence set out in SEQ ID No: 18.

Another aspect of the application refers to a TCR specific for XAGE-1 comprising a TCR α chain having an amino acid sequence which is at least 50%, at least 60%, at least 70%, at least 80%, at least 85%, at least 90%, at least 95%, at least 96%, at least 97%, at least 98%, at least 99% identical to SEQ ID No: 31 and a TCR β chain having an amino acid sequence which is at least 50%, at least 60%, at least 70%, at least 80%, at least 85%, at least 90%, at least 95%, at least 96%, at least 97%, at least 98%, at least 99% identical to SEQ ID No: 32.

Certain embodiments relate to a TCR receptor specific for XAGE-1 comprising a TCR α chain having the amino acid sequence of SEQ ID No: 31 and a TCR β chain comprising the amino acid sequence of SEQ ID No: 32.

Further, the application is related to a TCR receptor specific for XAGE-1 comprising a TCR α chain and a TCR β chain, wherein
  the TCR α chain comprises an amino acid sequence which is at least 80% identical to SEQ ID No: 31 and comprises a CDR3 having the sequence of SEQ ID No: 27;
  the TCR β chain comprises an amino acid sequence which is at least 80% identical to SEQ ID No: 32 and comprises a CDR3 having the sequence of SEQ ID No: 28.

Certain embodiments relate to a TCR receptor specific for XAGE-1 comprising TCR α chain and a TCR β chain, wherein
  the TCR α chain comprises an amino acid sequence which is at least 50%, at least 60%, at least 70%, at least 80%, at least 85%, at least 90%, at least 95%, at least 96%, at least 97%, at least 98%, at least 99% identical to SEQ ID No: 31 and comprises a CDR3 having the sequence of SEQ ID No: 27;
  the TCR β chain comprises an amino acid sequence which is at least 50%, at least 60%, at least 70%, at least 80%, at least 85%, at least 90%, at least 95%, at least 96%, at least 97%, at least 98%, at least 99% identical to SEQ ID No: 32 and comprises a CDR3 having the sequence of SEQ ID No: 28.

Certain embodiments refer to a TCR receptor specific for XAGE-1 comprising a TCR α chain encoded by a nucleotide sequence which is at least 50%, at least 60%, at least 70%, at least 80%, at least 85%, at least 90%, at least 95%, at least 96%, at least 97%, at least 98%, at least 99% identical to SEQ ID No: 29 and a TCR β chain encoded by a nucleotide sequence which is at least 50%, at least 60%, at least 70%, at least 80%, at least 85%, at least 90%, at least 95%, at least 96%, at least 97%, at least 98%, at least 99% identical to SEQ ID No: 30.

Certain embodiments relate to a TCR receptor specific for XAGE-1 comprising a TCR α chain encoded by the nucleotide sequence SEQ ID No: 29 and a TCR β chain encoded by the nucleotide sequence SEQ ID No: 30.

Further, the application is related to a TCR receptor specific for XAGE-1 comprising a TCR α chain and a TCR β chain, wherein
  the TCR α chain is encoded by a nucleotide sequence which is at least 80% identical to SEQ ID No: 29 and comprises a CDR3 region encoded by the nucleotide sequence set out in SEQ ID No: 25;
  the TCR β chain is encoded by a nucleotide sequence which is at least 80% identical to SEQ ID No: 30 and comprises a CDR3 region encoded by the nucleotide sequence set out SEQ ID No: 26.

Certain embodiments relate to a TCR receptor specific for XAGE-1 comprising TCR α chain and a TCR β chain, wherein
  the TCR α chain is encoded by a nucleotide sequence which is at least 50%, at least 60%, at least 70%, at least 80%, at least 85%, at least 90%, at least 95%, at least 96%, at least 97%, at least 98%, at least 99% identical to SEQ ID No: 29 and comprises a CDR3 region encoded by the nucleotide sequence set out in SEQ ID No: 25;

the TCR β chain is encoded by a nucleotide sequence which is at least 50%, at least 60%, at least 70%, at least 80%, at least 85%, at least 90%, at least 95%, at least 96%, at least 97%, at least 98%, at least 99% identical to SEQ ID No: 30 and comprises a CDR3 region encoded by the nucleotide sequence set out in SEQ ID No: 26.

The present application also relates to the nucleic acid molecules coding for the TCRs as defined above.

Useful changes in the overall nucleic acid sequence may be to codon optimization. Alterations may be made which lead to conservative substitutions within the expressed amino acid sequence. These variations can be made in complementarity determining and non-complementarity determining regions of the amino acid sequence of the TCR chain that do not affect function. Usually, additions and deletions should not be performed in the CDR3 region.

The concept of "conservative amino acid substitutions" is understood by the skilled artisan, and preferably means that codons encoding positively-charged residues (H, K, and R) are substituted with codons encoding positively-charged residues, codons encoding negatively-charged residues (D and E) are substituted with codons encoding negatively-charged residues, codons encoding neutral polar residues (C, G, N, Q, S, T, and Y) are substituted with codons encoding neutral polar residues, and codons encoding neutral non-polar residues (A, F, I, L, M, P, V, and W) are substituted with codons encoding neutral non-polar residues. These variations can spontaneously occur, be introduced by random mutagenesis, or can be introduced by directed mutagenesis. Those changes can be made without destroying the essential characteristics of these polypeptides. The ordinarily skilled artisan can readily and routinely screen variant amino acids and/or the nucleic acids encoding them to determine if these variations substantially reduce or destroy the ligand binding capacity by methods known in the art.

Epitope tags are short stretches of amino acids to which a specific antibody can be raised, which in some embodiments allows one to specifically identify and track the tagged protein that has been added to a living organism or to cultured cells. Detection of the tagged molecule can be achieved using a number of different techniques. Examples of such techniques include: immunohistochemistry, immunoprecipitation, flow cytometry, immunofluorescence microscopy, ELISA, immunoblotting ("Western"), and affinity chromatography. Epitope tags add a known epitope (antibody binding site) on the subject protein, to provide binding of a known and often high-affinity antibody, and thereby allowing one to specifically identify and track the tagged protein that has been added to a living organism or to cultured cells.

In the context of the present invention, a "functional" TCR α- and/or β-chain fusion protein shall mean a TCR or TCR variant, for example modified by addition, deletion or substitution of amino acids, that maintains at least substantial biological activity. In the case of the α- and/or β-chain of a TCR, this shall mean that both chains remain able to form a T-cell receptor (either with a non-modified α- and/or β-chain or with another inventive fusion protein α- and/or β-chain) which exerts its biological function, in particular binding to the specific peptide-MHC complex of said TCR, and/or functional signal transduction upon specific peptide: MHC interaction.

In specific embodiments the TCR may be modified, to be a functional T-cell receptor (TCR) α- and/or β-chain fusion protein, wherein said epitope-tag has a length of between 6 to 15 amino acids, preferably 9 to 11 amino acids. In another embodiment the TCR may be modified to be a functional T-cell receptor (TCR) α- and/or β-chain fusion protein wherein said T-cell receptor (TCR) α- and/or β-chain fusion protein comprises two or more epitope-tags, either spaced apart or directly in tandem. Embodiments of the fusion protein can contain 2, 3, 4, 5 or even more epitope-tags, as long as the fusion protein maintains its biological activity/activities ("functional").

Preferred is a functional T-cell receptor (TCR) α- and/or β-chain fusion protein according to the present invention, wherein said epitope-tag is selected from, but not limited to, CD20 or Her2/neu tags, or other conventional tags such as a myc-tag, FLAG-tag, T7-tag, HA (hemagglutinin)-tag, His-tag, S-tag, GST-tag, or GFP-tag. myc, T7, GST, GFP tags are epitopes derived from existing molecules. In contrast, FLAG is a synthetic epitope tag designed for high antigenicity (see, e.g., U.S. Pat. Nos. 4,703,004 and 4,851,341). The myc tag can preferably be used because high quality reagents are available to be used for its detection. Epitope tags can of course have one or more additional functions, beyond recognition by an antibody. The sequences of these tags are described in the literature and well known to the person of skill in art.

Another aspect of the invention is directed to a T cell expressing a TCR as defined above.

In addition, the invention refers to a vector comprising one or more of the nucleic acid sequences coding for a TCR as defined above. The vector is preferably a plasmid, shuttle vector, phagemide, cosmid, expression vector, retroviral vector, adenoviral vector or particle and/or vector to be used in gene therapy.

A "vector" is any molecule or composition that has the ability to carry a nucleic acid sequence into a suitable host cell where synthesis of the encoded polypeptide can take place. Typically and preferably, a vector is a nucleic acid that has been engineered, using recombinant DNA techniques that are known in the art, to incorporate a desired nucleic acid sequence (e.g., a nucleic acid of the invention). The vector may comprise DNA or RNA and/or comprise liposomes. The vector may be a plasmid, shuttle vector, phagemide, cosmid, expression vector, retroviral vector, adenoviral vector or particle and/or vector to be used in gene therapy. A vector may include nucleic acid sequences that permit it to replicate in a host cell, such as an origin of replication. A vector may also include one or more selectable marker genes and other genetic elements known to those of ordinary skill in the art. A vector preferably is an expression vector that includes a nucleic acid according to the present invention operably linked to sequences allowing for the expression of said nucleic acid.

In another aspect of the invention, a cell is provided in which the above a nucleic acid sequence coding for a TCR as described above has been introduced. In the T cell the above described vector comprising a nucleic acid sequence coding for the above described TCR may be introduced or in vitro transcribed RNA coding for said TCR may be introduced. The cell may be a peripheral blood lymphocyte such as a T cell. The method of cloning and exogenous expression of the TCR is for example described in Engels et al. (Relapse or eradication of cancer is predicted by peptide-major histocompatibility complex affinity. Cancer Cell, 23(4), 516-26. 2013).

Another aspect of the application relates to the TCRs or cells expressing a TCR as defined above for use as a medicament. Thus, the present application also contemplates a pharmaceutical composition comprising the TCRs or cells expressing a TCR as described above and a pharmaceutically acceptable carrier. Certain embodiments refer to the TCRs or cells expressing a TCR as defined above for use in treating a disease involving malignant cells expressing GAGE-1, SSX-4, XAGE-1, or a mixture thereof. Thus, the application also refers to the TCRs as defined above for use in the treatment of cancer. Accordingly, the application is directed to a method of treating a patient in need of adoptive cell therapy, said method comprising administering to said patient a pharmaceutical composition as defined herein. The patient may suffer from diseases involving malignant cells expressing GAGE-1, SSX-4, XAGE-1, or a mixture thereof.

Those active components of the present invention are preferably used in such a pharmaceutical composition, in doses mixed with an acceptable carrier or carrier material, that the disease can be treated or at least alleviated. Such a composition can (in addition to the active component and the carrier) include filling material, salts, buffer, stabilizers, solubilizers and other materials, which are known state of the art.

The term "pharmaceutically acceptable" defines a non-toxic material, which does not interfere with effectiveness of the biological activity of the active component. The choice of the carrier is dependent on the application.

The pharmaceutical composition may contain additional components which enhance the activity of the active component or which supplement the treatment. Such additional components and/or factors can be part of the pharmaceutical composition to achieve synergistic effects or to minimize adverse or unwanted effects.

Techniques for the formulation or preparation and application/medication of active components of the present invention are published in "Remington's Pharmaceutical Sciences", Mack Publishing Co., Easton, Pa., latest edition. An appropriate application is a parenteral application, for example intramuscular, subcutaneous, intramedular injections as well as intrathecal, direct intraventricular, intravenous, intranodal, intraperitoneal or intratumoral injections. The intravenous injection is the preferred treatment of a patient.

According to a preferred embodiment, the pharmaceutical composition is an infusion or an injection.

An injectable composition is a pharmaceutically acceptable fluid composition comprising at least one active ingredient, e.g., an expanded T-cell population (for example autologous or allogenic to the patient to be treated) expressing a TCR. The active ingredient is usually dissolved or suspended in a physiologically acceptable carrier, and the composition can additionally comprise minor amounts of one or more non-toxic auxiliary substances, such as emulsifying agents, preservatives, and pH buffering agents and the like. Such injectable compositions that are useful for use with the fusion proteins of this disclosure are conventional; appropriate formulations are well known to those of ordinary skill in the art.

EXAMPLES

Validation of Efficient MHC Class-II Cross-Presentation by CrossTAg Vector

To obtain MHC class-II cross-presentation of RNA-encoded proteins, selected antigen DNA sequences were coupled with a MHC class-II targeting signal (CrossTAg). For this purpose, the ER-translocation signal of the human lysosomal-associated membrane protein 1 (LAMP-1) 5' was fused to the transmembrane and cytoplasmic domains of human DC-LAMP. These two signal components were separated by unique restriction sites that allow integration of selected antigen sequences in frame with CrossTAg. The LAMP-1 signal peptide was used to facilitate co-translational translocation of newly synthesized proteins into the ER. Following translocation, the cytoplasmic DC-LAMP targeting signal (YXXΦ motif; X stands for any natural occurring amino acid; Φ stands for any hydrophobic amino acid; SEQ ID NO: 38) should ensure efficient protein shuttling to the endosomal/lysosomal compartment.

We integrated a partial coding sequence of the Epstein-Barr virus nuclear antigen (EBNA)-3C, encoding a 1 kb fragment containing the known epitope for the EBNA-3C-specific CD4$^+$ T cell clone 3H10 (described in Xiaojun Yu, et al.: Antigen-armed antibodies targeting B lymphoma cells effectively activate antigen-specific CD4+ T cells. Blood 2015 Mar. 5; 125(10):1601-10.; http://www.iedb.org/assayId/2445148) which is HLA-DRB1*11:01 restricted. Additional constructs comprising only one or neither of the two signals were used to assess the necessity of each sequence for the desired MHC class-II cross-presentation (FIG. 1 a). RNA was subsequently transcribed in vitro from the linearized plasmids and transfected into different APC expressing the required restriction element HLA-DRB1*11:01. Measurement of IFN-γ production upon specific antigen recognition by clone 3H10 allowed detection of efficient MHC class-II cross-presentation of endogenously translated and processed protein in co-culture experiments with DCs, as well as mini-EBV-transformed lymphoblastoid cell lines (mLCL), transfected with the EBNA-3C CrossTAg-RNA (FIG. 1 b). Only ivt-RNA containing the LAMP-1 ER-translocation signal led to detectable T cell activation. When compared to the pronounced MHC class-II presentation achieved with EBNA-3C-CrossTAg-RNA, the LAMP-1 signal peptide alone conferred minor cross-presentation capacity. We confirmed this data using one additional CD4$^+$ T cell clone specific for a HLA-DRB1*15:01-restricted epitope of EBV-antigen BNRF1 (data not shown).

Next, we used 3H10 T cells to elucidate whether the CrossTAg signal led to MHC class-II presentation via 1) protein secretion and re-uptake or 2) cell-internal presentation pathways. For this, we transfected HLA-DRB1*11:01-positive or HLA-DRB1*11:01-negative DCs with EBNA-3C-CrossTAg-RNA. Transfected and un-transfected DCs were co-incubated in all possible combinations (HLA-DRB1*11:01-positive/-negative) and later co-cultured with 3H10 cells. Recognition of APCs was only detected when HLA-DRB1*11:01-positive DCs were transfected with antigen-CrossTAg-RNA. Recognition of untransfected HLA-DRB1*11:01-positive DCs that had potentially taken-up and processed antigen secreted by HLA-DRB1*11:01-negative DCs was not detected (FIG. 8).

Antigen-CrossTAg-Induced CD40L Expression

To develop a rapid method for selective enrichment of antigen-specific CD4$^+$ T cells, we assessed the ability of antigen-CrossTAg-RNA-transfected DCs to induce CD40L expression in responding CD4$^+$ T cells. For this, we stained 3H10 T cells with a fluorescent tracing dye and mixed them with autologous PBL to final concentrations of 10%, 5%, 1% or 0.1% of total cells (FIG. 1 c). These different fractions were co-cultured with EBNA-3C-CrossTAg ivt-RNA-transfected autologous DCs and stained for CD40L expression. At 6 h of co-culture, we detected substantial CD40L expression on EBNA-3C-specific 3H10 cells but observed only marginal CD40L expression on autologous PBL. Even at the lowest concentration of 3H10 cells (0.1%), subsequent sorting of CD40L-positive CD4$^+$ T cells resulted in a population of 66% 3H10 cells.

Alternative ER Translocation Signal Sequences

Measuring IFN-γ production upon specific antigen recognition by clone 3H10, we were able to detect efficient MHC class-II cross-presentation of endogenously translated and processed protein in co-culture experiments with APCs, transfected with different EBNA-3C tagged with CrossTAg-RNA and different alternatives to CrossTAg-RNA (FIG. 11).

Efficient MHC Class-II and MHC Class-I Presentation

We could show that the use of the CrossTAg signal facilitates not only MHC class-II presentation but also MHC class-I presentation (FIG. 12).

Efficient Presentations of Several Antigens Encoded by the Same Ivt-mRNA Molecule Further we could establish an efficient approach of presenting several epitopes originating from different antigens by the same ivt-mRNA. As shown in FIG. 12 antigen presenting cells expressing the construct, which comprises two epitopes originating from different antigens activate EBNA-3C specific clone 3H10 as well as tyrosinase specific clone IVSB. Therefore the ivt construct having two different epitopes facilitates the presentation of both epitopes.

Activation of PBL with RNA-Pulsed DCs

Enroute to a high-throughput approach, we explored the potential of using multiple candidate antigens in parallel for $CD4^+$ T cell priming. Thus, $CD4^+$ T cells present in unseparated PBL were activated using DCs transfected with ivt-RNA species encoding four different C/T-antigens (GAGE-1, MAGE-A4, SSX-4 and XAGE-1) that were fused to the CrossTAg-signal. DCs were transfected with each ivt-RNA individually via electroporation, as described (Javorovic, M. et al. (2008) Inhibitory effect of RNA pool complexity on stimulatory capacity of RNA-pulsed dendritic cells. J Immunother 31(1): 52-62.). We measured the maturation status of transfected DCs by levels of co-stimulatory molecule expression by flow cytometry. Our DCs showed a mature phenotype with high expression of co-stimulatory molecules (CD80, CD83, CD86) and HLA class II (FIG. 9a).

To evaluate transfection efficiency, antigen cDNA, derived from mRNA extracted from transfected DCs, was analyzed by quantitative RT-PCR. Acquired data showed a range of $1.5*10^5$ to $2*10^7$ fold increase in C/T-antigen mRNA copy numbers after electroporation (FIG. 9 b). Furthermore, about 68% of DCs expressed enhanced green fluorescent protein (eGFP) as detected by flow cytometry 12 hours after transfection with control eGFP ivt-RNA (data not shown).

After transfection with antigen-CrossTAg RNA, the four separate DC populations were pooled and used simultaneously to prime non-separated autologous PBL of a healthy donor. The subsequent expansion procedure included two rounds of APC stimulation. Frozen aliquots of the initial DC preparations were thawed and used for the restimulation cultures.

Isolation of Activated $CD4^+$ T Cells

After each 14-day interval of DC co-culture, primed autologous PBL displayed a 3-4 fold overall increase in cell numbers. Changes in the CD4:CD8 ratios were measured at multiple time points to track expansion of activated $CD4^+$ T cells. Additionally, PBL samples were co-incubated with antigen-loaded DCs in the presence of CD40-blocking antibody and subsequently analyzed by flow cytometry using specific mAbs for CD4, CD137 and CD40L (FIG. 2 a). Over the monitored period, the CD4:CD8 ratio inverted from 1.7 on day 0 to 0.7 on day 27, reflecting an enhanced proliferation of $CD8^+$ T cells (data not shown). However, within the $CD4^+$ T cell population, the percentage of CD40L-positive T cells rose from 4.6% on day 13 to over 30% on day 27. In contrast, the number of putative regulatory T cells (Tregs), that are described to be CD137 single-positive $CD4^+$ T cells (Schoenbrunn et al., A converse 4-1BB and CD40 ligand expression pattern delineates activated regulatory T cells (Treg) and conventional T cells enabling direct isolation of alloantigen-reactive natural Foxp3+ Treg. J Immunol. 2012; 189(12):5985-94.), dropped by about 36%.

After the third stimulation cycle, CD40L-positive $CD4^+$ T cells were enriched from the PBL culture and cloned directly into 96-well-plates by FACS (FIG. 10). The cloned $CD4^+$ T cells were expanded. Excess cells from the cloning procedure were established as bulk CD40L-positive (CD40Lpos) and CD40L-negative (CD40Lneg) $CD4^+$ T cell lines. Their analysis indicated successful enrichment of C/T-antigen-specific $CD4^+$ T lymphocytes since CD40Lpos-sorted $CD4^+$ T cells proliferated nearly four-fold during 14 days following C/T-antigen-specific restimulation and released significantly higher amounts of IFN-γ after co-culture with RNA-transfected APC compared to the CD40Lneg T cells (FIG. 2 b, c).

Screening for C/T-Antigen-Reactive $CD4^+$ T Cell Clones

We tested T cell clones that expanded in 96-well-cultures for antigen reactivity in IFN-γ release assays starting 12 days after FACS cloning (FIG. 3 a). Co-cultures using a mixture of all four antigen-CrossTAg RNA-loaded DCs indicated that, alongside non-reactive and unspecific T cell clones, multiple antigen-reactive T cell clones were present. With few exceptions, antigen-reactive T cell clones showed no background activation in co-culture with mock-transfected DCs.

To validate these observations, we re-tested selected clones one day later using ivt-RNA-transfected mLCL as an alternative source of APC. IFN-γ and GM-CSF release assays confirmed the previous findings with DCs (FIG. 3 b). Furthermore, selected T cell clones were stained for CD4 and CD8 surface expression and all were found to express the CD4 co-receptor (FIG. 3 c).

Molecular and Functional Characterization of Antigen-Specific $CD4^+$ T Cell Clones To analyze the individual antigen specificities of antigen-reactive $CD4^+$ T cell clones, we subsequently co-cultured individual clones with distinct populations of APCs transfected with single species of antigen-CrossTAg RNA. Responses were measured via IFN-γ secretion using a standard ELISA (FIG. 4). We detected antigen-specific $CD4^+$ T cell clones recognizing each of the four C/T-antigens used for priming. T cell clones showed no background activation by mock-transfected APC nor any detectable cross reactivity to the other antigens to which they were exposed during priming.

Using TCR repertoire analysis we identified 4 unique T cell receptor sequences from the multitude of isolated clones. MHC restriction assays showed that the different T cells recognized epitopes presented by different MHC class II allotypes, data not shown). We demonstrated the importance of having antigen fused to the CrossTAg signal by the fact that DC provided with ivt-RNA without this signal could not induce IFN-γ secretion by isolated $CD4^+$ T cell clones (FIG. 5 a). Activation-induced IFN-γ secretion was only elicited when $CD4^+$ T cell clones were co-cultured with APC transfected with antigen-CrossTAg RNA. One exception was the T cell clone expressing the GAGE-1-TCR-2, which also recognized APCs transfected with RNA lacking the respective sorting signals, albeit at substantially lower levels.

To confirm the antigen specificity of our isolated CD4+ T cell clones, we loaded APCs with recombinant proteins. CD4+ T cell clones showed positive IFN-γ secretion to protein-loaded APC that was comparable to activation seen in co-culture with antigen-CrossTAg RNA-transfected APC (FIG. 5 b).

Direct MHC Class-II Epitope Identification

For these 4 clones, a method for direct mapping of MHC class-II epitopes (DEPI) (Milosevic, S. et al. (2006) Identification of major histocompatibility complex class II-restricted antigens and epitopes of the Epstein-Barr virus) was used to define the epitopes they recognized in association with MHC class-II molecules. We validated the recognition of isolated antigen fragments with short overlapping Cross-TAg-RNA constructs and used these to further consign the minimal epitope sequences (FIG. 6 a, b). Hereby, GAGE-1-TCR-1 was found to recognize the GAGE-$1_{76\text{-}98}$ epitope presented by HLA-DRB5*01:01. Interestingly, the two XAGE-1-specific CD4+ T cell clones recognized an identical XAGE-$1_{37\text{-}49}$ epitope presented by two different MHC class-II allotypes (HLA-DRB1*13:02 and HLA-DRB5*01:01).

Transgenic Expression of C/T-Antigen-Specific TCRs

Following TCR repertoire analysis, we reconstructed isolated TCR sequences using TCR expression vectors. CD4+ T cells of the 3H10 clone (EBNA-3C-specific and HLA-DRB1*11:01 restricted) were transfected with corresponding TCR-α- and β-chains of the CD4+ T cell clones GAGE-1-TCR-2, XAGE-1-TCR-1 or TCR-2. TCR-engineered 3H10 cells were co-cultured with C/T-antigen-loaded APCs (FIG. 7). By measuring IFN-γ secretion, we showed that the specificities of all CD4+ T cell clones were successfully transferred to the 3H10 cells, without impairing their endogenous EBV-specific TCR. Thus, after TCR transfection, the 3H10 cells recognized EBNA-3C-CrossTAg ivt-RNA-transfected APCs as well as APCs transfected with the corresponding C/T-antigen-CrossTAg ivt-RNA.

Methods

Genetic Constructs

The pGEM-eGFP-A120 vector was used as the starting construct for the CrossTAg-vector (S. Milosevic). This polyA120 variant of the original pGEM vector renders transcribed RNA with higher stability and led to improved protein expression. The plasmid further contained a unique AgeI site at the 5' end of the eGFP cDNA, as well as a unique EcoRI site at the 3' end. The poly-A tail is followed by a SpeI site that allows linearization of the plasmid for ivt-RNA production.

The pGEM-CrossTAg-A120 plasmid was cloned by replacing eGFP with cDNA coding for the CrossTAg targeting signal. The CrossTAg sequence consists of the ER-translocation signal of the human lysosome-associated membrane protein-1 (LAMP-1, accession: NP_005552, aa 1-28) fused 5' to the transmembrane and cytoplasmic domain of DC-LAMP (accession: NP_055213, aa 376-416). For insertion of antigen-encoding cDNA, the distinct Cross-TAg sequences are separated by an 18-bp spacer containing NheI, KpnI and PstI restriction sites without disrupting the LAMP1 open reading frame (ORF). The codon optimized Cross-TAg sequence was designed virtually using computational cloning software and synthesized by GeneArt (Regensburg). The complete CrossTAg sequence was subsequently cut from plasmid DNA using AgeI (5' end) and EcoRI (3' end) restriction sites and ligated into the MCS of the equally digested pGEM-A120 vector. For cloning of various C/T antigen-CrossTAg constructs (pGEM-GAGE-1-CrossTAg-A120, pGEM-MAGE-A4-CrossTAg-A120, pGEM-NY-ESO-1-CrossTAg-A120, pGEM-SSX-4-CrossTAg-A120, pGEM-XAGE-1-CrossTAg-A120) antigen cDNA was amplified from plasmids by PCR (accessions: GAGE-1, U19142; MAGE-A4, NM_001011550; NY-ESO1, AJ003149; SSX-4, U90841; XAGE-1, AF251237) using forward and reverse gene-specific primers and ligated via NheI and PstI/NotI restriction sites. The primers used for PCR reactions are all available upon request. All antigen sequences were inserted into the split CrossTAg signal of pGEM-CrossTAg-A120 with-out disrupting the initial ORF.

For the validation of CD4+ T cell epitopes, complementary oligonucleotides were synthesized (Metabion) and annealed. Cohesive ends, generated upon annealing, were used for direct ligation of these short antigen sequences into the CrossTAg vector.

Production of Ivt-RNA

Following SpeI linearization, pGEM-plasmids were used as templates for single-species in vitro transcribed (ivt)-RNA production using the mMESSAGE mMACHINE T7 kit (Ambion), according to the manufacturer's instructions. For quality control, ivt-RNA product length was analyzed by agarose gel electrophoresis. Concentration and purity were determined by means of the Nanodrop ND-1000 spectrophotometer (Thermo Scientific).

Cell Culture

Monocyte-derived 3d mDC were generated and transfected as described in Bürdek et al. (Journal of Translational Medicine 2010, 8:90. RNA transfection of mDC and and mini-Epstein-Barr virus-(EBV)-transformed lymphoblastoid cell lines (mLCL) was achieved by electroporation as described in Bürdek et al (Three-day dendritic cells for vaccine development: Antigen uptake, processing and presentation. Journal of Translational Medicine 2010, 8:90).

mLCL were grown as suspension cultures in LCL medium as described previously (Milosevic, S. et al. (2006) Identification of major histocompatibility complex class II-restricted antigens and epitopes of the Epstein-Barr virus). Protein loading of mLCL was achieved by culturing $2*10^6$ cells in 24-well plates in 2 ml LCL medium for 16 h in the presence of 25 μg recombinant human GAGE-1, MAGE-A4, SSX-4 or XAGE-1 protein (enriched via 6×-cHis tag after expression in HEK-293T cells). At the end of the incubation period, the cells were washed twice using RPMI 1640 and co-cultured with specific CD4+ T cell clones.

Quantitative RT-PCR

Cellular RNA of transfected and un-transfected DCs was isolated and corresponding cDNA was synthesized with oligo-dT primers using the First Strand cDNA Synthesis Kit for RT-PCR (AMV) (Roche). Differences in antigen template numbers were determined by quantitative RT-PCR (qRT-PCR) using the LightCycler® 480 SYBR Green I Master Kit (Roche), according to the manufacturer's manual. Gene-specific primers (αEnolase, GAGE-1, MAGE-A4, SSX-4 and XAGE-1) used for RT-PCR reactions are all available upon request. Measurements were normalized to the house-keeping gene αEnolase and analyzed according to the AACP-method.

Surface Phenotyping of T Cells and DCs

Surface markers expressed by T cells and DCs were detected with the following antibodies: PE-conjugated CCR7-specific antibody (3D12) (eBioscience), Hz450-conjugated CD4-specific anti-body (RPA-T4), Hz500-conjugated CD8-specific antibody (RPA-T8), FITC-conjugated CD14-specific antibody (M5E2), PE-conjugated CD40-specific antibody (5C3), PE-conjugated CD40L-specific antibody (TRAP1), PE-conjugated CD80-specific antibody (L307.4), FITC-conjugated CD83-specific antibody (HB15e), FITC-conjugated CD86-specific antibody (2331), APC-conjugated CD137-specific antibody (4B4-1), FITC-conjugated DC-SIGN-specific antibody (DCN46), PE-conjugated HLA-DR-specific antibody (G46-6) (all from BD Biosciences). After washing, cells were stained for 30 min at 4° C. and propidium iodid (2 µg/ml) was added for the exclusion of dead cells. Expression of all surface markers was analyzed by flow cytometry (LSRII, BD). Post-acquisition data analysis was done using FlowJo 8 software (TreeStar). The analysis of CD40L surface expression on T cells was performed as described
(Frentsch, M. et al.
(2005) Direct access to CD4+ T cells specific for defined antigens
according to CD154 expression. Nat Med 11(10): 1118-1124) using 2 µg/ml αCD40 antibody (clone G28.5, provided by M. Frentsch, Berlin-Brandenburg Center for Regenerative Therapies) and assessed 6 h after the start of the T cell:APC co-culture.

De Novo Priming of PBL with RNA-Transfected DCs 3d mDCs of a healthy donor were transfected in separate populations with 2 single-species CrossTAg-RNA coding for the C/T-antigens GAGE-1, MAGE-A4, SSX-4 and XAGE-1. after electroporation the transfected mDCs were harvested and mixedmDCs of this mixture were co-cultured within a 1:2 ratio peripheral blood lymphocytes (PBL), which were non-adherent during the plastic adherence of PBMC in the process of mDC generation. The cells were cultured at 37° C. in a humidified at-mosphere. Inter-leukine-2 (IL-2, 20 U/ml; Chiron Behring) and 5 ng IL-7/ml (Promokine) were added after 1 day and then on every other day. Mixed mDCs that were not used for the PBL co-culture were cryopreserved and were thawed for re-stimulation of the de novo induced PBL culture.

Isolation and Expansion of Antigen-Specific CD4+ T Cells

Primed PBL were co-cultured in a 2:1 ratio with Cross-TAg-RNA-transfected mDCs (4-antigen mix) for 6 h in the presence of αCD40 antibody, as described (Frentsch, M., (2005) Direct access to CD4+ T cells specific for defined antigens according to CD154 expression. Nat Med 11(10): 1118-1124 . . . ). After the stimulation period, cells were stained with αCD4- and αCD40L-specific antibodies (SK3 and TRAP1; BD Biosciences). DAPI was added for the exclusion of dead cells. Using a FACSAria III (BD Biosciences), live CD40L-positive CD4+ T cells were sorted as single cells into wells of round-bottom 96-well plates. CD4+ T cell clones in 96-well plates were expanded using antigen-CrossTAg ivt-RNA-transfected mLCL, feeder cells and IL-2.

Cytokine Release Assay

To measure activation induced cytokine secretion, $5*10^4$ T cells were co-cultured with $1*10^5$ ivt-RNA-loaded APCs (DC/mLCL) in 200 µl T cell medium in round-bottom 96-well plates at 37° C. in a humidified atmosphere. T cells with mock-transfected APCs or without stimulator cells were used as negative controls. After 16 h of co-culture, supernatants were harvested and assessed by enzyme-linked immunosorbent assay (ELISA) using the OptEIA Human IFN-γ or GM-CSF Set (both from BD Biosciences).

Ivt-RNA-Based TCR Gene Transfer

TCR-α- and TCR-β-chain rearrangements and sequences were determined by PCR using a pan-el of TCR-Vα- and TCR-Vβ-specific primers as described (Steinle, A., et al. (1995) In vivo expansion of HLA-B35 alloreactive T cells sharing homologous T cell receptors: evidence for maintenance of an oligoclonally dominated allospecificity by persistent stimulation with an autologous MHC/peptide complex. J Exp Med 181(2): 503-513.). After substitution of the constant regions of both TCR chains by their murine counterparts, the codon-optimized TCR-α- and TCR-β-chain sequences were synthesized and cloned into an expression vector for RNA production. To validate the specificity of these TCR sequences, cells of T cell clone 3H10 (HLA-DRB1*11:01 restricted, EBV EBNA-3C-specific) were co-transfected with TCR-α- and TCR-β-ivt-RNA and used for cytokine secretion assays.

The application further comprises the following embodiments:

Embodiment 1

A method of generating human antigen-specific T lymphocytes comprising the following steps:
A) expression of at least one fusion protein comprising
    at least one antigen or a fragment thereof,
    an endoplasmatic reticulum (ER)-translocation signal sequence preceding the N-terminus of the antigen, and
    a transmembrane and cytoplasmic domain comprising an endosomal/lysosomal targeting sequence following the C-terminus of the antigen,
in antigen presenting cells; and
B) exposing of a cell population comprising T lymphocytes to the antigen presenting cells of step A) in vitro in order to activate antigen-specific T lymphocytes specific for the antigen expressed by the antigen presenting cell.

Embodiment 2

The method according to embodiment 1, wherein exposing in step B) is co-culturing the antigen presenting cells with a cell population comprising T lymphocytes.

Embodiment 3

The method according to embodiment 1 or 2, wherein the expression of step A) is transient expression or stable expression, preferably transient expression.

Embodiment 4

The method according to embodiment 3, wherein the transient expression is carried out by introducing ivt-RNA coding for the at least one fusion protein.

Embodiment 5

The method according to any one of the preceding embodiments, wherein the method further comprises the step of
C1) enrichment of activated and/or antigen specific T lymphocytes.

Embodiment 6

The method according to embodiment 5, wherein the enrichment of activated T lymphocytes comprises the following steps:
(a) contacting the cell population comprising activated antigen-specific T lymphocytes with at least one binding molecule which specifically binds to a marker protein specifically expressed by activated T lymphocytes or with at least one MHC molecules presenting an epitope of the desired antigen;
(b) isolating T lymphocytes to which the at least one binding molecule or the at least one MHC molecule presenting an epitope of the desired antigen is bound.

Embodiment 7

The method according to embodiment 6, wherein the binding molecule which specifically binds to the marker protein is an antibody, a derivative of an antibody, a fragment of an antibody, or a conjugate of the aforementioned with a further molecule.

Embodiment 8

The method according to embodiment 6 or 7, wherein the at least one marker protein specifically expressed by activated T lymphocytes is selected from the group comprising Ox40, CD137, CD40L, PD-1, IL-2 receptor, interferon γ, IL-2, GM-CSF and TNF-α.

Embodiment 9

The method according to embodiment 8, wherein in step (a) the cells are further contacted with a binding molecule that specifically binds to CD4.

Embodiment 10

The method according to embodiment 8 or 9, wherein in step (a) the cells are further contacted with a binding molecule that specifically binds to CD8.

Embodiment 11

The method according to embodiment 6, wherein selecting activated CD4 T cells comprises the following steps:
(a1) contacting the cell population of step B) with an antibody against CD40 in order to block the interaction between CD40-CD40L of the antigen presenting cells and the antigen-specific T lymphocytes and to accumulate CD40L at the surface of T lymphocytes;
(a2) contacting the cell population comprising activated antigen-specific T lymphocytes with an anti-CD40L antibody;
(b) isolating the T lymphocytes marked with an anti-CD40L antibody and an anti-CD4 antibody.

Embodiment 12

The method according to any one of the preceding embodiments, wherein the method further comprises the step
C2) identification of antigen-specific T lymphocytes, comprising the following steps:
a) incubation of expanded cell clones of the cell population comprising activated antigen-specific T lymphocytes with
　(i) antigen presenting cells as defined in step A), and
　(ii) control antigen presenting cells or in the absence of antigen presenting cells;
b) comparison of the activation profile of the incubation with (i) and (ii) for each cell clone;
c) identification of antigen-specific cell clones based on the comparison of b);
wherein the activation by (i) but not by (ii) indicates that the cell clone is antigen-specific.

Embodiment 13

The method according to any one of the preceding embodiments, wherein in step B) the antigen presenting cells are added to the cell population comprising T lymphocytes at least once, optionally at least twice, optionally at least three times, optionally three times.

Embodiment 14

The method according to embodiment 12, wherein the time interval between repeated additions of antigen presenting cells is 7 to 21 days, preferably 12 to 16 days, more preferably 13 to 15 day, even more preferably 14 days.

Embodiment 15

The method according to any one of the preceding embodiments, wherein the ER translocation signal sequence is derived from an endosomal/lysosomal associated protein.

Embodiment 16

The method according to embodiment 15, wherein the endosomal/lysosomal associated protein is selected from the group comprising LAMP1, LAMP2, DC-LAMP, CD68 and CD1b, preferably LAMP1.

Embodiment 17

The method according any one of the preceding embodiments, wherein the endosomal/lysosomal targeting sequence is derived from LAMP1 or DC-LAMP, preferably DC-LAMP.

Embodiment 18

The method according to any one of the preceding embodiments, wherein the transmembrane and cytoplasmic domain comprising an endosomal/lysosomal targeting sequence is derived from LAMP1 or DC-LAMP, preferably DC-LAMP.

Embodiment 19

The method according to any one to the preceding embodiments, wherein the ER translocation signal sequence is human.

Embodiment 20

The method according to any one of the preceding embodiments, wherein the transmembrane and cytoplasmic domain comprising an endosomal/lysosomal targeting sequence is human.

Embodiment 21

The method according to any one of the preceding embodiments, wherein the ER translocation signal comprises the sequence SEQ ID NO: 33 or a fragment thereof.

Embodiment 22

The method according to embodiment 20, wherein the ER translocation signal sequence consists of the sequence SEQ ID NO: 34.

Embodiment 23

The method according to any one of the preceding embodiments, wherein the antigen presenting cells are selected from dendritic cells, activated B cells, monocytes, macrophages, EBV-transformed lymphoblastoid cell lines, preferably dendritic cells, more preferably monocyte derived dendritic cells.

Embodiment 24

The method according to any one of the preceding embodiments, wherein the antigen presenting cells comprise different populations of antigen presenting cells, each population expressing a different antigen fusion protein.

Embodiment 25

The method according to any one of the preceding embodiments, wherein the antigen presenting cells are mature dendritic cells generated by a method comprising the following steps:
i) provision of monocytes;
ii) incubation of the monocytes of step i) with IL-4 and GM-CSF;
iii) incubation of the monocytes of step ii) with IL-4 and GM-CSF in combination with a maturation cocktail.

Embodiment 26

The method according to embodiment 25, wherein the maturation cocktail comprises a combination of IL-β, TNF-α, INF-γ, TLR7/8 agonist, PGE2 and TLR3 agonist.

Embodiment 27

The method according to embodiment 25 or 26, wherein incubation of step ii) lasts at least 2 days.

Embodiment 28

The method according to embodiments 25 to 27, wherein incubation of step iii) lasts at least 12 hours, preferably 24 hours.

Embodiment 29

The method according to embodiment 28, wherein the TLR7/8 agonist is R848 and wherein the TLR3 agonist is poly(I:C).

Embodiment 30

The method according to any one of the preceding embodiments, wherein the cell population comprising T lymphocytes is a population of peripheral blood lymphocytes.

Embodiment 31

The method according to any one of the preceding embodiments, wherein cell population comprising T lymphocytes is a population of unseparated peripheral blood lymphocytes.

Embodiment 32

The method according to any one of the preceding embodiments, wherein the cell population is enriched for T lymphocytes, preferably $CD8^+$ and/or $CD4^+$ T lymphocytes.

Embodiment 33

Method of any of the preceding embodiments, wherein the fusion protein comprises at least two antigens or fragments thereof.

Embodiment 34

A T lymphocyte obtainable by the method according to embodiments 1 to 33.

Embodiment 35

An expression vector comprising:
a human endoplasmatic reticulum (ER)-translocation signal sequence, and
a human transmembrane and cytoplasmic domain comprising an endosomal/lysosomal targeting sequence.

Embodiment 36

Expression Vector according to embodiment 1, wherein the vector comprises a promotor for in-vitro mRNA transcription.

Embodiment 37

The expression vector according to embodiment 35 or 36, wherein the ER translocation signal sequence is derived from an endosomal/lysosomal associated protein.

Embodiment 38

The expression vector according to any of embodiments 35 to 37, wherein the endosomal/lysosomal associated protein is selected from the group comprising LAMP1, LAMP2, DC-LAMP, CD68, CD1b.

Embodiment 39

The expression vector according to any of embodiments 35 to 38, wherein the endosomal/lysosomal targeting sequence is derived from LAMP1 or DC-LAMP, preferably DC-LAMP.

Embodiment 40

The expression vector according to any of embodiments 35 to 39, wherein the transmembrane and cytoplasmic domain comprising an endosomal/lysosomal targeting sequence is derived from LAMP1 or DC-LAMP, preferably DC-LAMP.

Embodiment 41

The expression vector according to any of embodiments 35 to 40, wherein the ER translocation signal sequence is human.

Embodiment 42

The expression vector according to any of embodiments 35 to 41, wherein the transmembrane and cytoplasmic domain comprising an endosomal/lysosomal targeting sequence is human.

Embodiment 43

The expression vector according to any of embodiments 35 to 42, wherein ER translocation signal sequence comprises the sequence of SEQ ID NO: 33 or a fragment thereof.

Embodiment 44

The expression vector according to any of embodiments 35 to 43, wherein ER translocation signal consists of the sequence of SEQ ID NO: 34.

Embodiment 45

The expression vector according to any of embodiments 35 to 44, wherein the endosomal/lysosomal targeting sequence comprises the motif of SEQ ID NO: 38.

Embodiment 46

The expression vector according to any of embodiments 35 to 45, wherein the endosomal/lysosomal targeting signal sequence is the sequence of SEQ ID NO: 39.

Embodiment 47

The expression vector according to any of embodiments 35 to 46, wherein the transmembrane and cytoplasmic domain comprising an endosomal/lysosomal targeting sequence comprises the sequence SEQ ID NO: 54 or a fragment thereof, such as SEQ ID NO: 35 or a fragment thereof.

Embodiment 48

The expression vector according to any of embodiments 35 to 47, further comprising a restriction site between the ER translocation signal sequence and the human transmembrane and cytoplasmic domain comprising an endosomal/lysosomal targeting sequence.

Embodiment 49

The expression vector according to any of embodiments 35 to 48, wherein the vector further comprises at least one antigen, or a fragment thereof which is inserted between human endoplasmatic reticulum (ER)-translocation signal sequence, and the human transmembrane and cytoplasmic domain comprising an endosomal/lysosomal targeting sequence.

Embodiment 50

The expression vector according to any of embodiments 49, wherein the vector comprises at least two antigens, or a fragments thereof which are inserted between human endoplasmatic reticulum (ER)-translocation signal sequence, and the human transmembrane and cytoplasmic domain comprising an endosomal/lysosomal targeting sequence.

Embodiment 51

The expression vector according to any of embodiments 35 to 50, wherein the vector comprises a nucleic acid sequence encoding a full length amino acid sequence of an antigen.

Embodiment 52

The expression vector according to any of embodiments 35 to 51, wherein the vector comprises a fragment of a nucleic acid sequence encoding an amino acid sequence of an antigen.

Embodiment 53

The expression vector according to embodiment 52, wherein the antigen is a tumor antigen or a viral antigen.

Embodiment 54

The expression vector according to embodiment 53, wherein the tumor antigen is selected from the group consisting of viral tumor antigen, tumor-specific antigen, tumor associated antigen and an antigen carrying patient specific mutations and being expressed in tumor cells of the patient.

Embodiment 55

The expression vector according to any of embodiments 35 to 54, wherein the tumor antigen is a tumor associated antigen.

Embodiment 56

The expression vector according to any of embodiments 35 to 55, wherein tumor associated antigen is a cancer/testis antigen (C/T antigen).

Embodiment 57

The expression vector according to any of embodiments 35 to 56, wherein the C/T antigen is selected from the group comprising MAGE-A1, MAGE-A3, MAGE-A4, NY-ESO1, tumor/testis-antigen 1B, GAGE-1, SSX-4, XAGE-1, BAGE, GAGE, SCP-1, SSX-2, SSX-4, CTZ9, CT10, SAGE and CAGE.

Embodiment 58

The expression vector according to any of embodiments 35 to 57, wherein the C/T antigen is selected from the group consisting of GAGE-1, SSX-4 and XAGE-1.

Embodiment 59

Use of the expression vector according to any one of embodiments 35 to 58 for in vitro generation of antigen-specific T lymphocytes.

Embodiment 60

T-lymphocytes for use in a method of preventing or treating cancer comprising administering to a mammal the T-lymphocytes according to embodiment 34.

Embodiment 61

A method for generating an antigen-specific TCR comprising steps of the method according to any one of embodiments 1 to 33 and further comprising the step of isolating a TCR from the activated antigen-specific lymphocyte.

Embodiment 62

A TCR isolated from a lymphocyte according to embodiment 34.

Embodiment 63

A TCR specific for GAGE-1 comprising
a TCR α chain comprising a CDR 3 region encoded by the nucleotide sequence set out in SEQ ID NO: 5,
a TCR β chain comprising a CDR 3 region encoded by the nucleotide sequence set out in SEQ ID NO: 6.

Embodiment 64

The TCR specific for GAGE-1 according to embodiment 63, comprising
a TCR α chain which is encoded by a nucleotide sequence being at least 80% identical to SEQ ID NO: 5, and which TCR α chain comprises a CDR 3 region encoded by the nucleotide sequence set out in SEQ ID NO: 1,
a TCR β chain which is encoded by a nucleotide sequence being at least 80% identical to SEQ ID NO: 6, and which TCR β chain comprises a CDR 3 region encoded by the nucleotide sequence set out in SEQ ID NO: 2.

Embodiment 65

A TCR specific for SSX-4 comprising
a TCR α chain comprising a CDR 3 region encoded by the nucleotide sequence set out in SEQ ID NO: 13,
a TCR β chain comprising a CDR 3 region encoded by the nucleotide sequence set out in SEQ ID NO: 14.

Embodiment 66

The TCR specific for SSX-4 according to embodiment 65, comprising
a TCR α chain which is encoded by a nucleotide sequence being at least 80% identical to SEQ ID NO: 13, and which TCR α chain comprises a CDR 3 region encoded by the nucleotide sequence set out in SEQ ID NO: 9,
a TCR β chain which is encoded by a nucleotide sequence being at least 80% identical to SEQ ID NO: 14, and which TCR β chain comprises a CDR 3 region encoded by the nucleotide sequence set out in SEQ ID NO: 10.

Embodiment 67

A TCR specific for XAGE-1 comprising
a TCR α chain comprising a CDR 3 region encoded by the nucleotide sequence set out in SEQ ID NO: 21,
a TCR β chain comprising a CDR 3 region encoded by the nucleotide sequence set out in SEQ ID NO: 22.

Embodiment 68

The TCR specific for XAGE-1 according to embodiment 66, comprising
a TCR α chain which is encoded by a nucleotide sequence being at least 80% identical to SEQ ID NO: 21, and which TCR α chain comprises a CDR 3 region encoded by the nucleotide sequence set out in SEQ ID NO: 17,
a TCR β chain which is encoded by a nucleotide sequence being at least 80% identical to SEQ ID NO: 22, and which TCR β chain comprises a CDR 3 region encoded by the nucleotide sequence set out in SEQ ID NO: 18.

Embodiment 69

A TCR specific for XAGE-1 comprising
a TCR α chain comprising a CDR 3 region encoded by the nucleotide sequence set out in SEQ ID NO: 29,
a TCR β chain comprising a CDR region encoded by the nucleotide sequence set out in SEQ ID NO: 30.

Embodiment 70

The TCR specific for XAGE-1 according to embodiment 68, comprising
a TCR α chain encoded by a nucleotide sequence being at least 80% identical to SEQ ID NO: 29, and which TCR α chain comprises a CDR 3 region encoded by the nucleotide sequence set out in SEQ ID NO: 25,
a TCR β chain which is encoded by a nucleotide sequence being at least 80% identical to SEQ ID NO: 30, and which TCR β chain comprises a CDR region encoded by the nucleotide sequence set out in SEQ ID NO: 26.

Embodiment 71

TCR according to any one of embodiments 62 to 70 for use in a method of preventing or treating cancer.

Embodiment 72

Method for preventing or treating cancer comprising the step of administering to a mammal the TCR according to any one of embodiments 62 to 70.

---

The invention claimed is:

1. A method of generating human antigen-specific T lymphocytes comprising:
   a) expressing at least one fusion protein in antigen presenting cells, wherein said fusion protein comprises
      (i) at least two antigens or fragments thereof;
      (ii) an endoplasmatic reticulum (ER)-translocation signal sequence preceding the N-terminus of the at least two antigens or fragments thereof; and
      (iii) a transmembrane and cytoplasmic domain comprising an endosomal/lysosomal targeting sequence following the C-terminus of the at least two antigens or fragments thereof;
   b) exposing a cell population comprising T lymphocytes to the antigen presenting cells of step a) in vitro to activate antigen-specific T lymphocytes specific for the at least two antigens or fragments thereof expressed by the antigen presenting cells; and
   c) enriching activated T lymphocytes, antigen specific T lymphocytes, or both activated T lymphocytes and antigen specific T lymphocytes, wherein enriching activated T lymphocytes, antigen specific T lymphocytes, or both activated T lymphocytes and antigen specific T lymphocytes comprises:
      (i) contacting the cell population comprising activated antigen-specific T lymphocytes with a binding molecule which specifically binds to a marker protein specifically expressed by activated T lymphocytes or with MHC molecules presenting an epitope of the desired antigen; and
      (ii) isolating T lymphocytes to which the binding molecule or the MHC molecule presenting an epitope of the desired antigen is bound;
   wherein each antigen is a tumor antigen or a viral antigen.

2. The method of claim 1, wherein the marker protein specifically expressed by activated T lymphocytes is selected from the group consisting of Ox40, CD137, CD40L, PD-1, IL-2 receptor, interferon y, IL-2, GM-CSF and TNF-α.

3. The method of claim 1, wherein the method further comprises identifying antigen-specific T lymphocyte cell clones.

4. The method of claim 3, wherein identifying antigen-specific T lymphocyte cell clones comprises:
   a) incubating expanded cell clones of the cell population comprising activated antigen-]specific T lymphocytes with
      (i) said antigen presenting cells, and
      (ii) control antigen presenting cells or in the absence of antigen presenting cells;
   b) comparing the activation profile of the incubation with the cells of (i) and (ii) for each cell clone; and
   c) identifying antigen-specific T lymphocyte cell clones based on step b),
   wherein the activation by the cells of (i) but not by the cells of (ii) indicates that the cell clone is antigen-specific.

5. The method of claim 1, wherein the ER translocation signal sequence is derived from an endosomal/lysosomal associated protein, and wherein the endosomal/lysosomal associated protein is selected from the group consisting of LAMP1, LAMP2, DC-LAMP, CD68, and CD 1 b.

6. The method of claim 5, wherein the endosomal/lysosomal associated protein is LAMP1.

7. The method of claim 1, wherein the transmembrane and cytoplasmic domain comprising an endosomal/lysosomal targeting sequence is derived from LAMP1 or DC-LAMP.

8. The method of claim 7, wherein the transmembrane and cytoplasmic domain comprising an endosomal/lysosomal targeting sequence is derived from DC-LAMP.

9. The method of claim 1, wherein the ER translocation signal sequence is human and wherein the transmembrane and cytoplasmic domain comprising an endosomal/lysosomal targeting sequence is human.

10. The method of claim 1, wherein the antigen presenting cells comprise different populations of antigen presenting cells, and wherein each population of antigen presenting cells expresses a different fusion protein.

11. The method of claim 1, wherein the antigen presenting cells are mature dendritic cells, and wherein the mature dendritic cells are generated by a method comprising the steps of:

i) providing monocytes;
ii) incubating the monocytes of step i) with IL-4 and GM-CSF; and
iii) incubating the monocytes of step ii) with IL-4 and GM-CSF in combination with a maturation cocktail, wherein the maturation cocktail comprises a combination of IL-β, TNF-α, INF-γ, TLR7/8 agonist, PGE2, and TLR3 agonist.

12. The method of claim 1, wherein the cell population comprising T lymphocytes is a population of unseparated peripheral blood lymphocytes.

13. The method of claim 1, wherein the cell population comprising T lymphocytes is enriched for T lymphocytes.

14. The method of claim 13, wherein the cell population comprising T lymphocytes is enriched for CD8+T lymphocytes, CD4+T lymphocytes, or both CD8+T lymphocytes and CD4+T lymphocytes.

15. The method of claim 1, further comprising isolating a TCR from the activated antigen-specific lymphocyte.

16. The method of claim 1, wherein the tumor antigen is a cancer/testis antigen (C/T antigen).

17. The method according to claim 16, wherein the C/T antigen is selected from MAGE-A1, MAGE-A3, MAGE-A4, NY-ESO1, tumor/testis-antigen 1B, GAGE-1, SSX-4, XAGE-1, BAGE, GAGE, SCP-1, SSX-2, SSX-4, CTZ9, CT10, SAGE, or CAGE.

18. The method of claim 1, wherein the fusion protein comprises, from N-terminus to C-terminus, the ER-translocation signal sequence, a first antigen or fragment thereof, a second antigen or fragment thereof, and the transmembrane and cytoplasmic domain comprising an endosomal/lysosomal targeting sequence.

19. The method of claim 1, wherein each antigen is a tumor antigen.

20. The method of claim 1, wherein each antigen is a viral antigen.

* * * * *

UNITED STATES PATENT AND TRADEMARK OFFICE
CERTIFICATE OF CORRECTION

PATENT NO. : 11,155,589 B2
APPLICATION NO. : 16/065024
DATED : October 26, 2021
INVENTOR(S) : Milosevic et al.

It is certified that error appears in the above-identified patent and that said Letters Patent is hereby corrected as shown below:

In the Claims

Column 73, in Claim 1, Line 40, replace "in vitro" with --*in vitro*--;
in Claim 2, Line 63, replace "interferon y" with --interferon γ--.

Column 74, in Claim 4, Line 28, replace "antigen-]specific" with --antigen-specific--;
in Claim 5, Line 46, replace "CD 1 b" with --CD 1b--.

Column 75, in Claim 14, Line 15, replace "CD8+T" with --$CD8^+$ T--;
in Claim 14, Line 16, replace "CD4+T lymphocytes, or both CD8+T lymphocytes" with --$CD4^+$ T lymphocytes, or both $CD8^+$ T lymphocytes--;
in Claim 14, Line 17, replace "CD4+T" with --$CD4^+$ T--.

Signed and Sealed this
Twenty-second Day of March, 2022

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 54

<210> SEQ ID NO 1
<211> LENGTH: 42
<212> TYPE: DNA
<213> ORGANISM: Homo sapiens

<400> SEQUENCE: 1
tgtgctgagc ggactcaggg cggatctgaa aagctggtct tt                           42

<210> SEQ ID NO 2
<211> LENGTH: 33
<212> TYPE: DNA
<213> ORGANISM: Homo sapiens

<400> SEQUENCE: 2
tgtgccaccc agagaaacac tgaagctttc ttt                                     33

<210> SEQ ID NO 3
<211> LENGTH: 14
<212> TYPE: PRT
<213> ORGANISM: Homo sapiens

<400> SEQUENCE: 3

Cys Ala Glu Arg Thr Gln Gly Gly Ser Glu Lys Leu Val Phe
1               5                   10

<210> SEQ ID NO 4
<211> LENGTH: 11
<212> TYPE: PRT
<213> ORGANISM: Homo sapiens

<400> SEQUENCE: 4

Cys Ala Thr Gln Arg Asn Thr Glu Ala Phe Phe
1               5                   10

<210> SEQ ID NO 5
<211> LENGTH: 825
<212> TYPE: DNA
<213> ORGANISM: Homo sapiens

<400> SEQUENCE: 5
atgatgaagt gtccacaggc tttactagct atcttttggc ttctactgag ctgggtgagc         60
agtgaagaca aggtggtaca aagccctcta tctctggttg tccacgaggg agacaccgta        120
actctcaatt gcagttatga agtgactaac tttcgaagcc tactatgta caagcaggaa         180
aagaaagctc ccacatttct atttatgcta acttcaagtg gaattgaaaa gaagtcagga        240
agactaagta gcatattaga taagaaagaa cttttccagc atcctgaacat cacagccacc       300
cagaccggag actcggccat ctacctctgt gctgagcgga ctcagggcgg atctgaaaag        360
ctggtctttg gaagggaac gaaactgaca gtaaacccat atatccagaa ccctgaccct         420
gccgtgtacc agctgagaga ctctaaatcc agtgacaagt ctgtctgcct attcaccgat        480
tttgattctc aaacaaatgt gtcacaaagt aaggattctg atgtgtatat cacagacaaa        540
actgtgctag acatgaggtc tatggacttc aagagcaaca gtgctgtggc ctggagcaac        600
aaatctgact tgcatgtgc aaacgccttc aacaacagca ttattccaga agaccttc           660
ttccccagcc cagaaagttc ctgtgatgtc aagctggtcg agaaaagctt tgaaacagat        720
acgaaccta actttcaaaa cctgtcagtg attgggttcc gaatcctcct cctgaaagtg        780
gccgggttta atctgctcat gacgctgcgg ctgtggtcca gctga                       825

<210> SEQ ID NO 6
<211> LENGTH: 927
<212> TYPE: DNA
<213> ORGANISM: Homo sapiens

<400> SEQUENCE: 6

```
atgggcacaa ggttgttctt ctatgtggcc ctttgtctcc tgtggacagg acacatggat      60
gctggaatca cccagagccc aagacacaag gtcacagaga caggaacacc agtgactctg     120
agatgtcacc agactgagaa ccaccgctat atgtactggt atcgacaaga cccggggcat     180
gggctgaggc tgatccatta ctcatatggt gttaaagata ctgacaaagg agaagtctca     240
gatggctata gtgtctctag atcaaagaca gaggatttcc tcctcactct ggagtccgct     300
accagctccc agacatctgt gtacttctgt gccacccaga gaaacactga agctttcttt     360
ggacaaggca ccagactcac agttgtagag gacctgaaaa acgtgttccc acccgaggtc     420
gctgtgtttg agccatcaga agcagagatc tcccacaccc aaaaggccac actggtgtgc     480
ctggccacag gcttctaccc cgaccacgtg agctgagct ggtgggtgaa tgggaaggag     540
gtgcacagtg gggtcagcac agacccgcag cccctcaagg agcagcccgc ctcaatgac     600
tccagatact gcctgagcag ccgcctgagg gtctcggcca ccttctggca gaaccccgc     660
aaccacttcc gctgtcaagt ccagttctac gggctctcgg agaatgacga gtggaccccag     720
gatagggcca aacctgtcac ccagatcgtc agcgccgagg cctggggtag agcagactgt     780
ggcttcacct ccgagtctta ccagcaaggg gtcctgtctg ccaccatcct ctatgagatc     840
ttgctaggga aggccacctt gtatgccgtg ctggtcagtg ccctcgtgct gatggccatg     900
gtcaagagaa aggattccag aggctga                                          927
```

```
<210> SEQ ID NO 7
<211> LENGTH: 274
<212> TYPE: PRT
<213> ORGANISM: Homo sapiens

<400> SEQUENCE: 7

Met Met Lys Cys Pro Gln Ala Leu Leu Ala Ile Phe Trp Leu Leu Leu
1               5                   10                  15

Ser Trp Val Ser Ser Glu Asp Lys Val Val Gln Ser Pro Leu Ser Leu
            20                  25                  30

Val Val His Glu Gly Asp Thr Val Thr Leu Asn Cys Ser Tyr Glu Val
        35                  40                  45

Thr Asn Phe Arg Ser Leu Leu Trp Tyr Lys Gln Glu Lys Lys Ala Pro
    50                  55                  60

Thr Phe Leu Phe Met Leu Thr Ser Ser Gly Ile Glu Lys Lys Ser Gly
65                  70                  75                  80

Arg Leu Ser Ser Ile Leu Asp Lys Lys Glu Leu Ser Ser Ile Leu Asn
                85                  90                  95

Ile Thr Ala Thr Gln Thr Gly Asp Ser Ala Ile Tyr Leu Cys Ala Glu
            100                 105                 110

Arg Thr Gln Gly Gly Ser Glu Lys Leu Val Phe Gly Lys Gly Thr Lys
        115                 120                 125

Leu Thr Val Asn Pro Tyr Ile Gln Asn Pro Asp Pro Ala Val Tyr Gln
    130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
            180                 185                 190

Asn Ser Ala Val Ala Trp Ser Asn Lys Ser Asp Phe Ala Cys Ala Asn
        195                 200                 205
```

```
Ala Phe Asn Asn Ser Ile Ile Pro Glu Asp Thr Phe Phe Pro Ser Pro
    210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
            260                 265                 270

Ser Ser

<210> SEQ ID NO 8
<211> LENGTH: 308
<212> TYPE: PRT
<213> ORGANISM: Homo sapiens

<400> SEQUENCE: 8

Met Gly Thr Arg Leu Phe Phe Tyr Val Ala Leu Cys Leu Leu Trp Thr
1               5                   10                  15

Gly His Met Asp Ala Gly Ile Thr Gln Ser Pro Arg His Lys Val Thr
            20                  25                  30

Glu Thr Gly Thr Pro Val Thr Leu Arg Cys His Gln Thr Glu Asn His
        35                  40                  45

Arg Tyr Met Tyr Trp Tyr Arg Gln Asp Pro Gly His Gly Leu Arg Leu
    50                  55                  60

Ile His Tyr Ser Tyr Gly Val Lys Asp Thr Asp Lys Gly Glu Val Ser
65                  70                  75                  80

Asp Gly Tyr Ser Val Ser Arg Ser Lys Thr Glu Asp Phe Leu Leu Thr
                85                  90                  95

Leu Glu Ser Ala Thr Ser Ser Gln Thr Ser Val Tyr Phe Cys Ala Thr
            100                 105                 110

Gln Arg Asn Thr Glu Ala Phe Phe Gly Gln Gly Thr Arg Leu Thr Val
        115                 120                 125

Val Glu Asp Leu Lys Asn Val Phe Pro Pro Glu Val Ala Val Phe Glu
130                 135                 140

Pro Ser Glu Ala Glu Ile Ser His Thr Gln Lys Ala Thr Leu Val Cys
145                 150                 155                 160

Leu Ala Thr Gly Phe Tyr Pro Asp His Val Glu Leu Ser Trp Trp Val
                165                 170                 175

Asn Gly Lys Glu Val His Ser Gly Val Ser Thr Asp Pro Gln Pro Leu
            180                 185                 190

Lys Glu Gln Pro Ala Leu Asn Asp Ser Arg Tyr Cys Leu Ser Ser Arg
        195                 200                 205

Leu Arg Val Ser Ala Thr Phe Trp Gln Asn Pro Arg Asn His Phe Arg
    210                 215                 220

Cys Gln Val Gln Phe Tyr Gly Leu Ser Glu Asn Asp Glu Trp Thr Gln
225                 230                 235                 240

Asp Arg Ala Lys Pro Val Thr Gln Ile Val Ser Ala Glu Ala Trp Gly
                245                 250                 255

Arg Ala Asp Cys Gly Phe Thr Ser Glu Ser Tyr Gln Gln Gly Val Leu
            260                 265                 270

Ser Ala Thr Ile Leu Tyr Glu Ile Leu Leu Gly Lys Ala Thr Leu Tyr
        275                 280                 285

Ala Val Leu Val Ser Ala Leu Val Leu Met Ala Met Val Lys Arg Lys
    290                 295                 300
```

Asp Ser Arg Gly
305

<210> SEQ ID NO 9
<211> LENGTH: 39
<212> TYPE: DNA
<213> ORGANISM: Homo sapiens

<400> SEQUENCE: 9
tgtgctctgc gtcaaacctc ctacgacaag gtgatattt                    39

<210> SEQ ID NO 10
<211> LENGTH: 45
<212> TYPE: DNA
<213> ORGANISM: Homo sapiens

<400> SEQUENCE: 10
tgtgccagca gcttagcgga caggggagt gaaaaactgt ttttt              45

<210> SEQ ID NO 11
<211> LENGTH: 13
<212> TYPE: PRT
<213> ORGANISM: Homo sapiens

<400> SEQUENCE: 11

Cys Ala Leu Arg Gln Thr Ser Tyr Asp Lys Val Ile Phe
1               5                   10

<210> SEQ ID NO 12
<211> LENGTH: 15
<212> TYPE: PRT
<213> ORGANISM: Homo sapiens

<400> SEQUENCE: 12

Cys Ala Ser Ser Leu Ala Asp Arg Gly Ser Glu Lys Leu Phe Phe
1               5                   10                  15

<210> SEQ ID NO 13
<211> LENGTH: 819
<212> TYPE: DNA
<213> ORGANISM: Homo sapiens

<400> SEQUENCE: 13

| | |
|---|---|
| atgaactatt ctccaggctt agtatctctg atactcttac tgcttggaag aacccgtgga | 60 |
| aattcagtga cccagatgga agggccagtg actctctcag aagaggcctt cctgactata | 120 |
| aactgcacgt acacagccac aggataccct tcccttttct ggtatgtcca atatcctgga | 180 |
| gaaggtctac agctcctcct gaaagccacg aaggctgatg acaagggaag caacaaaggt | 240 |
| tttgaagcca cataccgtaa agaaaccact tctttccact ggagaaaagg ctcagttcaa | 300 |
| gtgtcagact cagcggtgta cttctgtgct ctgcgtcaaa cctcctacga caaggtgata | 360 |
| tttgggccag ggacaagctt atcagtcatt ccaaatatcc agaaccctga ccctgccgtg | 420 |
| taccagctga gagactctaa atccagtgac aagtctgtct gcctattcac cgattttgat | 480 |
| tctcaaacaa atgtgtcaca agtaaggat tctgatgtgt atatcacaga caaaactgtg | 540 |
| ctagacatga ggtctatgga cttcaagagc aacagtgctg tggcctggag caacaaatct | 600 |
| gactttgcat gtgcaaacgc cttcaacaac agcattattc cagaagacac cttcttcccc | 660 |
| agcccagaaa gttcctgtga tgtcaagctg gtcgagaaaa gctttgaaac agatacgaac | 720 |
| ctaaactttc aaaacctgtc agtgattggg ttccgaatcc tcctcctgaa agtggccggg | 780 |

```
tttaatctgc tcatgacgct gcggctgtgg tccagctga                           819
```

<210> SEQ ID NO 14
<211> LENGTH: 936
<212> TYPE: DNA
<213> ORGANISM: Homo sapiens

<400> SEQUENCE: 14

```
atgggcacca ggctcctctg ctgggcggcc ctctgtctcc tgggagcaga actcacagaa    60
gctggagttg cccagtctcc cagatataag attatagaga aaaggcagag tgtggctttt   120
tggtgcaatc ctatatctgg ccatgctacc ctttactggt accagcagat cctgggacag   180
ggcccaaagc ttctgattca gtttcagaat aacggtgtag tggatgattc acagttgcct   240
aaggatcgat ttctgcaga gaggctcaaa ggagtagact ccactctcaa gatccagcct   300
gcaaagcttg aggactcggc cgtgtatctc tgtgccagca gcttagcgga caggggagt   360
gaaaaactgt tttttggcag tggaacccag ctctctgtct tggaggacct gaacaaggtg   420
ttcccacccg aggtcgctgt gtttgagcca tcagaagcag agatctccca cacccaaaag   480
gccacactgg tgtgcctggc cacaggcttc ttccccgacc acgtggagct gagctggtgg   540
gtgaatggga aggaggtgca cagtggggtc agcacggacc cgcagcccct caaggagcag   600
cccgccctca tgactccag  atactgcctg agcagccgcc tgagggtctc ggccaccttc   660
tggcagaacc cccgcaacca cttccgctgt caagtccagt tctacgggct ctcggagaat   720
gacgagtgga cccaggatag ggccaaaccc gtcacccaga tcgtcagcgc cgaggcctgg   780
ggtagagcag actgtggctt tacctcggtg tcctaccagc aagggtcct gtctgccacc   840
atcctctatg agatcctgct agggaaggcc accctgtatg ctgtgctggt cagcgccctt   900
gtgttgatgg ccatggtcaa gagaaaggat ttctga                              936
```

<210> SEQ ID NO 15
<211> LENGTH: 272
<212> TYPE: PRT
<213> ORGANISM: Homo sapiens

<400> SEQUENCE: 15

```
Met Asn Tyr Ser Pro Gly Leu Val Ser Leu Ile Leu Leu Leu Leu Gly
1               5                   10                  15

Arg Thr Arg Gly Asn Ser Val Thr Gln Met Glu Gly Pro Val Thr Leu
            20                  25                  30

Ser Glu Glu Ala Phe Leu Thr Ile Asn Cys Thr Tyr Thr Ala Thr Gly
        35                  40                  45

Tyr Pro Ser Leu Phe Trp Tyr Val Gln Tyr Pro Gly Glu Gly Leu Gln
    50                  55                  60

Leu Leu Leu Lys Ala Thr Lys Ala Asp Asp Lys Gly Ser Asn Lys Gly
65                  70                  75                  80

Phe Glu Ala Thr Tyr Arg Lys Glu Thr Thr Ser Phe His Leu Glu Lys
                85                  90                  95

Gly Ser Val Gln Val Ser Asp Ser Ala Val Tyr Phe Cys Ala Leu Arg
            100                 105                 110

Gln Thr Ser Tyr Asp Lys Val Ile Phe Gly Pro Gly Thr Ser Leu Ser
        115                 120                 125

Val Ile Pro Asn Ile Gln Asn Pro Asp Pro Ala Val Tyr Gln Leu Arg
    130                 135                 140

Asp Ser Lys Ser Ser Asp Lys Ser Val Cys Leu Phe Thr Asp Phe Asp
145                 150                 155                 160
```

```
Ser Gln Thr Asn Val Ser Gln Ser Lys Asp Ser Asp Val Tyr Ile Thr
                165                 170                 175

Asp Lys Thr Val Leu Asp Met Arg Ser Met Asp Phe Lys Ser Asn Ser
            180                 185                 190

Ala Val Ala Trp Ser Asn Lys Ser Asp Phe Ala Cys Ala Asn Ala Phe
        195                 200                 205

Asn Asn Ser Ile Ile Pro Glu Asp Thr Phe Phe Pro Ser Pro Glu Ser
    210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
                245                 250                 255

Lys Val Ala Gly Phe Asn Leu Leu Met Thr Leu Arg Leu Trp Ser Ser
            260                 265                 270

<210> SEQ ID NO 16
<211> LENGTH: 311
<212> TYPE: PRT
<213> ORGANISM: Homo sapiens

<400> SEQUENCE: 16

Met Gly Thr Arg Leu Leu Cys Trp Ala Ala Leu Cys Leu Leu Gly Ala
1               5                   10                  15

Glu Leu Thr Glu Ala Gly Val Ala Gln Ser Pro Arg Tyr Lys Ile Ile
            20                  25                  30

Glu Lys Arg Gln Ser Val Ala Phe Trp Cys Asn Pro Ile Ser Gly His
        35                  40                  45

Ala Thr Leu Tyr Trp Tyr Gln Gln Ile Leu Gly Gln Gly Pro Lys Leu
    50                  55                  60

Leu Ile Gln Phe Gln Asn Asn Gly Val Val Asp Asp Ser Gln Leu Pro
65                  70                  75                  80

Lys Asp Arg Phe Ser Ala Glu Arg Leu Lys Gly Val Asp Ser Thr Leu
                85                  90                  95

Lys Ile Gln Pro Ala Lys Leu Glu Asp Ser Ala Val Tyr Leu Cys Ala
            100                 105                 110

Ser Ser Leu Ala Asp Arg Gly Ser Glu Lys Leu Phe Phe Gly Ser Gly
        115                 120                 125

Thr Gln Leu Ser Val Leu Glu Asp Leu Asn Lys Val Phe Pro Pro Glu
    130                 135                 140

Val Ala Val Phe Glu Pro Ser Glu Ala Glu Ile Ser His Thr Gln Lys
145                 150                 155                 160

Ala Thr Leu Val Cys Leu Ala Thr Gly Phe Phe Pro Asp His Val Glu
                165                 170                 175

Leu Ser Trp Trp Val Asn Gly Lys Glu Val His Ser Gly Val Ser Thr
            180                 185                 190

Asp Pro Gln Pro Leu Lys Glu Gln Pro Ala Leu Asn Asp Ser Arg Tyr
        195                 200                 205

Cys Leu Ser Ser Arg Leu Arg Val Ser Ala Thr Phe Trp Gln Asn Pro
    210                 215                 220

Arg Asn His Phe Arg Cys Gln Val Gln Phe Tyr Gly Leu Ser Glu Asn
225                 230                 235                 240

Asp Glu Trp Thr Gln Asp Arg Ala Lys Pro Val Thr Gln Ile Val Ser
                245                 250                 255

Ala Glu Ala Trp Gly Arg Ala Asp Cys Gly Phe Thr Ser Val Ser Tyr
```

```
                260                 265                 270
Gln Gln Gly Val Leu Ser Ala Thr Ile Leu Tyr Glu Ile Leu Leu Gly
            275                 280                 285

Lys Ala Thr Leu Tyr Ala Val Leu Val Ser Ala Leu Val Leu Met Ala
        290                 295                 300

Met Val Lys Arg Lys Asp Phe
305                 310

<210> SEQ ID NO 17
<211> LENGTH: 42
<212> TYPE: DNA
<213> ORGANISM: Homo sapiens

<400> SEQUENCE: 17
tgtgctgtga gagataattc aggaaacaca cctcttgtct tt                              42

<210> SEQ ID NO 18
<211> LENGTH: 42
<212> TYPE: DNA
<213> ORGANISM: Homo sapiens

<400> SEQUENCE: 18
tgtgccagta gtataatcca gggcagtgct ggctacacct tc                              42

<210> SEQ ID NO 19
<211> LENGTH: 14
<212> TYPE: PRT
<213> ORGANISM: Homo sapiens

<400> SEQUENCE: 19

Cys Ala Val Arg Asp Asn Ser Gly Asn Thr Pro Leu Val Phe
1               5                   10

<210> SEQ ID NO 20
<211> LENGTH: 14
<212> TYPE: PRT
<213> ORGANISM: Homo sapiens

<400> SEQUENCE: 20

Cys Ala Ser Ser Ile Ile Gln Gly Ser Ala Gly Tyr Thr Phe
1               5                   10

<210> SEQ ID NO 21
<211> LENGTH: 810
<212> TYPE: DNA
<213> ORGANISM: Homo sapiens

<400> SEQUENCE: 21
atgtggggag ttttccttct ttatgttttcc atgaagatgg gaggcactac aggacaaaac     60
attgaccagc ccactgagat gacagctacg gaaggtgcca ttgtccagat caactgcacg    120
taccagacat ctgggttcaa cgggctgttc tggtaccagc aacatgctgg cgaagcaccc    180
acatttctgt cttacaatgt tctggatggt ttggaggaga aggtcgtttt tcttcattc     240 cttagtcggt ctaaagggta cagttacctc cttttgaagg agctccagat gaaagactct    300
gcctcttacc tctgtgctgt gagagataat tcaggaaaca cacctcttgt ctttggaaag    360
ggcacaagac tttctgtgat tgcaaatatc cagaaccctg accctgccgt gtaccagctg    420
agagactcta atccagtgaa caagtctgtc tgcctattca ccgatttga ttctcaaaca    480 aatgtgtcac aaagtaagga ttctgatgtg tatatcacag acaaaactgt gctagacatg    540
```

| | |
|---|---|
| aggtctatgg acttcaagag caacagtgct gtggcctgga gcaacaaatc tgactttgca | 600 |
| tgtgcaaacg ccttcaacaa cagcattatt ccagaagaca ccttcttccc cagcccagaa | 660 |
| agttcctgtg atgtcaagct ggtcgagaaa agctttgaaa cagatacgaa cctaaacttt | 720 |
| caaaacctgt cagtgattgg gttccgaatc ctcctcctga agtggccgg gtttaatctg | 780 |
| ctcatgacgc tgcggctgtg gtccagctga | 810 |

<210> SEQ ID NO 22
<211> LENGTH: 930
<212> TYPE: DNA
<213> ORGANISM: Homo sapiens

<400> SEQUENCE: 22

| | |
|---|---|
| atgagcaacc aggtgctctg ctgtgtggtc ctttgtttcc tgggagcaaa caccgtggat | 60 |
| ggtggaatca ctcagtcccc aaagtacctg ttcagaaagg aaggacagaa tgtgaccctg | 120 |
| agttgtgaac agaatttgaa ccacgatgcc atgtactggt accgacagga cccagggcaa | 180 |
| gggctgagat tgatctacta ctcacagata gtaaatgact tcagaaagg agatatagct | 240 |
| gaagggtaca gcgtctctcg ggagaagaag aatccttttc ctctcactgt gacatcggcc | 300 |
| caaaagaacc cgacagcttt ctatctctgt gccagtagta taatccaggg cagtgctggc | 360 |
| tacaccttcg gttcggggac caggttaacc gttgtagagg acctgaacaa ggtgttccca | 420 |
| cccgaggtcg ctgtgtttga gccatcagaa gcagagatct cccacaccca aaaggccaca | 480 |
| ctggtgtgcc tggccacagg cttcttcccc gaccacgtgg agctgagctg gtgggtgaat | 540 |
| gggaaggagt gcacagtgg ggtcagcacg gacccgcagc ccctcaagga gcagcccgcc | 600 |
| ctcaatgact ccagatactg cctgagcagc cgcctgaggg tctcggccac cttctggcag | 660 |
| aacccccgca accacttccg ctgtcaagtc cagttctacg gctctcgga gaatgacgag | 720 |
| tggacccagg atagggccaa acccgtcacc cagatcgtca gcgccgaggc ctggggtaga | 780 |
| gcagactgtg ctttacctc ggtgtcctac agcaagggg tcctgtctgc caccatcctc | 840 |
| tatgagatcc tgctagggaa ggccacctg tatgctgtgc tggtcagcgc ccttgtgttg | 900 |
| atggccatgg tcaagagaaa ggatttctga | 930 |

<210> SEQ ID NO 23
<211> LENGTH: 269
<212> TYPE: PRT
<213> ORGANISM: Homo sapiens

<400> SEQUENCE: 23

Met Trp Gly Val Phe Leu Leu Tyr Val Ser Met Lys Met Gly Gly Thr
1               5                   10                  15

Thr Gly Gln Asn Ile Asp Gln Pro Thr Glu Met Thr Ala Thr Glu Gly
            20                  25                  30

Ala Ile Val Gln Ile Asn Cys Thr Tyr Gln Thr Ser Gly Phe Asn Gly
        35                  40                  45

Leu Phe Trp Tyr Gln Gln His Ala Gly Glu Ala Pro Thr Phe Leu Ser
    50                  55                  60

Tyr Asn Val Leu Asp Gly Leu Glu Glu Lys Gly Arg Phe Ser Ser Phe
65                  70                  75                  80

Leu Ser Arg Ser Lys Gly Tyr Ser Tyr Leu Leu Leu Lys Glu Leu Gln
                85                  90                  95

Met Lys Asp Ser Ala Ser Tyr Leu Cys Ala Val Arg Asp Asn Ser Gly
            100                 105                 110

```
Asn Thr Pro Leu Val Phe Gly Lys Gly Thr Arg Leu Ser Val Ile Ala
            115                 120                 125

Asn Ile Gln Asn Pro Asp Pro Ala Val Tyr Gln Leu Arg Asp Ser Lys
    130                 135                 140

Ser Ser Asp Lys Ser Val Cys Leu Phe Thr Asp Phe Asp Ser Gln Thr
145                 150                 155                 160

Asn Val Ser Gln Ser Lys Asp Ser Asp Val Tyr Ile Thr Asp Lys Thr
                165                 170                 175

Val Leu Asp Met Arg Ser Met Asp Phe Lys Ser Asn Ser Ala Val Ala
            180                 185                 190

Trp Ser Asn Lys Ser Asp Phe Ala Cys Ala Asn Ala Phe Asn Asn Ser
            195                 200                 205

Ile Ile Pro Glu Asp Thr Phe Phe Pro Ser Pro Glu Ser Ser Cys Asp
    210                 215                 220

Val Lys Leu Val Glu Lys Ser Phe Glu Thr Asp Thr Asn Leu Asn Phe
225                 230                 235                 240

Gln Asn Leu Ser Val Ile Gly Phe Arg Ile Leu Leu Leu Lys Val Ala
                245                 250                 255

Gly Phe Asn Leu Leu Met Thr Leu Arg Leu Trp Ser Ser
            260                 265

<210> SEQ ID NO 24
<211> LENGTH: 309
<212> TYPE: PRT
<213> ORGANISM: Homo sapiens

<400> SEQUENCE: 24

Met Ser Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
            20                  25                  30

Lys Glu Gly Gln Asn Val Thr Leu Ser Cys Glu Gln Asn Leu Asn His
        35                  40                  45

Asp Ala Met Tyr Trp Tyr Arg Gln Asp Pro Gly Gln Gly Leu Arg Leu
    50                  55                  60

Ile Tyr Tyr Ser Gln Ile Val Asn Asp Phe Gln Lys Gly Asp Ile Ala
65              70                  75                  80

Glu Gly Tyr Ser Val Ser Arg Glu Lys Lys Glu Ser Phe Pro Leu Thr
                85                  90                  95

Val Thr Ser Ala Gln Lys Asn Pro Thr Ala Phe Tyr Leu Cys Ala Ser
            100                 105                 110

Ser Ile Ile Gln Gly Ser Ala Gly Tyr Thr Phe Gly Ser Gly Thr Arg
        115                 120                 125

Leu Thr Val Val Glu Asp Leu Asn Lys Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220
```

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
            245                 250                 255

Ala Trp Gly Arg Ala Asp Cys Gly Phe Thr Ser Val Tyr Gln Gln
        260                 265                 270

Gly Val Leu Ser Ala Thr Ile Leu Tyr Glu Ile Leu Gly Lys Ala
    275                 280                 285

Thr Leu Tyr Ala Val Leu Val Ser Ala Leu Val Leu Met Ala Met Val
    290                 295                 300

Lys Arg Lys Asp Phe
305

<210> SEQ ID NO 25
<211> LENGTH: 42
<212> TYPE: DNA
<213> ORGANISM: Homo sapiens

<400> SEQUENCE: 25
tgtgctgccc tccgtggagg tagcaactat aaactgacat tt                              42

<210> SEQ ID NO 26
<211> LENGTH: 42
<212> TYPE: DNA
<213> ORGANISM: Homo sapiens

<400> SEQUENCE: 26
tgcgccagca gcttggccag gggagtcaat gagcagttct tc                              42

<210> SEQ ID NO 27
<211> LENGTH: 14
<212> TYPE: PRT
<213> ORGANISM: Homo sapiens

<400> SEQUENCE: 27

Cys Ala Ala Leu Arg Gly Gly Ser Asn Tyr Lys Leu Thr Phe
1               5                   10

<210> SEQ ID NO 28
<211> LENGTH: 14
<212> TYPE: PRT
<213> ORGANISM: Homo sapiens

<400> SEQUENCE: 28

Cys Ala Ser Ser Leu Ala Arg Gly Val Asn Glu Gln Phe Phe
1               5                   10

<210> SEQ ID NO 29
<211> LENGTH: 825
<212> TYPE: DNA
<213> ORGANISM: Homo sapiens

<400> SEQUENCE: 29
atgctcctgc tgctcgtccc agtgctcgag gtgatttttta ccctgggagg aaccagagcc         60
cagtcggtga cccagcttgg cagccacgtc tctgtctctg aaggagccct ggttctgctg         120
aggtgcaact actcatcgtc tgttccacca tatctcttct ggtatgtgca ataccccaac         180
caaggactcc agcttctcct gaagtacaca tcagcggcca cctggttaa aggcatcaac          240 ggttttgagg ctgaatttaa aagagtgaa acctccttcc acctgacgaa acctcagcc           300

-continued

```
catatgagcg acgcggctga gtacttctgt gctgccctcc gtggaggtag caactataaa    360
ctgacatttg aaaaggaac tctcttaacc gtgaatccaa atatccagaa ccctgaccct    420
gccgtgtacc agctgagaga ctctaaatcc agtgacaagt ctgtctgcct attcaccgat    480
tttgattctc aaacaaatgt gtcacaaagt aaggattctg atgtgtatat cacagacaaa    540
actgtgctag acatgaggtc tatggacttc aagagcaaca gtgctgtggc ctggagcaac    600
aaatctgact tgcatgtgc aaacgccttc aacaacagca ttattccaga agacaccttc    660
ttccccagcc cagaaagttc ctgtgatgtc aagctggtcg agaaaagctt tgaaacagat    720
acgaacctaa actttcaaaa cctgtcagtg attgggttcc gaatcctcct cctgaaagtg    780
gccgggttta atctgctcat gacgctgcgg ctgtggtcca gctga                    825
```

<210> SEQ ID NO 30
<211> LENGTH: 936
<212> TYPE: DNA
<213> ORGANISM: Homo sapiens

<400> SEQUENCE: 30

```
atgggctcca ggctgctctg ttgggtgctg ctttgtctcc tgggagcagg cccagtaaag    60
gctggagtca ctcaaactcc aagatatctg atcaaaacga gaggacagca agtgacactg   120
agctgctccc ctatctctgg cataggagt gtatcctggt accaacagac cccaggacag    180
ggccttcagt tcctctttga atacttcagt gagacacaga gaaacaaagg aaacttccct    240
ggtcgattct cagggcgcca gttctctaac tctcgctctg agatgaatgt gagcaccttg    300
gagctggggg actcggccct ttatctttgc gccagcagct ggccagggg agtcaatgag    360
cagttcttcg ggcagggac acggctcacc gtgctagagg acctgaaaaa cgtgttccca   420
cccgaggtcg ctgtgtttga gccatcagaa gcagagatct cccacaccca aaaggccaca    480
ctggtgtgcc tggccacagg cttctacccc gaccacgtgg agctgagctg gtgggtgaat    540
gggaaggagg tgcacagtgg ggtcagcaca gacccgcagc ccctcaagga gcagcccgcc    600
ctcaatgact ccagatactg cctgagcagc cgcctgaggg tctcggccac cttctggcag    660
aacccccgca accacttccg ctgtcaagtc cagttctacg ggctctcgga aatgacgag    720
tggacccagg atagggccaa acctgtcacc cagatcgtca gcgccgaggc tgggtaga    780
gcagactgtg gcttcacctc cgagtcttac cagcaagggg tcctgtctgc caccatcctc    840
tatgagatct tgctagggaa ggccaccttg tatgccgtgc tggtcagtgc cctcgtgctg    900
atggccatgg tcaagagaaa ggattccaga ggctga                              936
```

<210> SEQ ID NO 31
<211> LENGTH: 274
<212> TYPE: PRT
<213> ORGANISM: Homo sapiens

<400> SEQUENCE: 31

```
Met Leu Leu Leu Leu Val Pro Val Leu Glu Val Ile Phe Thr Leu Gly
1               5                   10                  15

Gly Thr Arg Ala Gln Ser Val Thr Gln Leu Gly Ser His Val Ser Val
            20                  25                  30

Ser Glu Gly Ala Leu Val Leu Arg Cys Asn Tyr Ser Ser Ser Val
            35                  40                  45

Pro Pro Tyr Leu Phe Trp Tyr Val Gln Tyr Pro Asn Gln Gly Leu Gln
        50                  55                  60

Leu Leu Leu Lys Tyr Thr Ser Ala Ala Thr Leu Val Lys Gly Ile Asn
```

```
            65                  70                  75                  80
Gly Phe Glu Ala Glu Phe Lys Lys Ser Glu Thr Ser Phe His Leu Thr
                85                  90                  95

Lys Pro Ser Ala His Met Ser Asp Ala Ala Glu Tyr Phe Cys Ala Ala
                100                 105                 110

Leu Arg Gly Gly Ser Asn Tyr Lys Leu Thr Phe Gly Lys Gly Thr Leu
                115                 120                 125

Leu Thr Val Asn Pro Asn Ile Gln Asn Pro Asp Pro Ala Val Tyr Gln
130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
                180                 185                 190

Asn Ser Ala Val Ala Trp Ser Asn Lys Ser Asp Phe Ala Cys Ala Asn
                195                 200                 205

Ala Phe Asn Asn Ser Ile Ile Pro Glu Asp Thr Phe Phe Pro Ser Pro
210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
                260                 265                 270

Ser Ser

<210> SEQ ID NO 32
<211> LENGTH: 311
<212> TYPE: PRT
<213> ORGANISM: Homo sapiens

<400> SEQUENCE: 32

Met Gly Ser Arg Leu Leu Cys Trp Val Leu Leu Cys Leu Leu Gly Ala
1               5                   10                  15

Gly Pro Val Lys Ala Gly Val Thr Gln Thr Pro Arg Tyr Leu Ile Lys
                20                  25                  30

Thr Arg Gly Gln Gln Val Thr Leu Ser Cys Ser Pro Ile Ser Gly His
                35                  40                  45

Arg Ser Val Ser Trp Tyr Gln Gln Thr Pro Gly Gln Gly Leu Gln Phe
            50                  55                  60

Leu Phe Glu Tyr Phe Ser Glu Thr Gln Arg Asn Lys Gly Asn Phe Pro
65                  70                  75                  80

Gly Arg Phe Ser Gly Arg Gln Phe Ser Asn Ser Arg Ser Glu Met Asn
                85                  90                  95

Val Ser Thr Leu Glu Leu Gly Asp Ser Ala Leu Tyr Leu Cys Ala Ser
                100                 105                 110

Ser Leu Ala Arg Gly Val Asn Glu Gln Phe Phe Gly Pro Gly Thr Arg
                115                 120                 125

Leu Thr Val Leu Glu Asp Leu Lys Asn Val Phe Pro Pro Glu Val Ala
130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
```

```
                       165                 170                 175
Trp Trp Val Asn Gly Lys Glu Val His Ser Gly Val Ser Thr Asp Pro
            180                 185                 190
Gln Pro Leu Lys Glu Gln Pro Ala Leu Asn Asp Ser Arg Tyr Cys Leu
        195                 200                 205
Ser Ser Arg Leu Arg Val Ser Ala Thr Phe Trp Gln Asn Pro Arg Asn
210                 215                 220
His Phe Arg Cys Gln Val Gln Phe Tyr Gly Leu Ser Glu Asn Asp Glu
225                 230                 235                 240
Trp Thr Gln Asp Arg Ala Lys Pro Val Thr Gln Ile Val Ser Ala Glu
                245                 250                 255
Ala Trp Gly Arg Ala Asp Cys Gly Phe Thr Ser Glu Ser Tyr Gln Gln
            260                 265                 270
Gly Val Leu Ser Ala Thr Ile Leu Tyr Glu Ile Leu Leu Gly Lys Ala
        275                 280                 285
Thr Leu Tyr Ala Val Leu Val Ser Ala Leu Val Leu Met Ala Met Val
    290                 295                 300
Lys Arg Lys Asp Ser Arg Gly
305                 310

<210> SEQ ID NO 33
<211> LENGTH: 28
<212> TYPE: PRT
<213> ORGANISM: Homo sapiens

<400> SEQUENCE: 33

Met Ala Ala Pro Gly Ser Ala Arg Arg Pro Leu Leu Leu Leu Leu Leu
1               5                   10                  15
Leu Leu Leu Leu Gly Leu Met His Cys Ala Ser Ala
            20                  25

<210> SEQ ID NO 34
<211> LENGTH: 29
<212> TYPE: PRT
<213> ORGANISM: Homo sapiens

<400> SEQUENCE: 34

Met Ala Ala Pro Gly Ser Ala Arg Arg Pro Leu Leu Leu Leu Leu Leu
1               5                   10                  15
Leu Leu Leu Leu Gly Leu Met His Cys Ala Ser Ala Ala
            20                  25

<210> SEQ ID NO 35
<211> LENGTH: 40
<212> TYPE: PRT
<213> ORGANISM: Homo sapiens

<400> SEQUENCE: 35

Ser Ser Asp Tyr Thr Ile Val Leu Pro Val Ile Gly Ala Ile Val Val
1               5                   10                  15
Gly Leu Cys Leu Met Gly Met Gly Val Tyr Lys Ile Arg Leu Arg Cys
            20                  25                  30
Gln Ser Ser Gly Tyr Gln Arg Ile
        35                  40

<210> SEQ ID NO 36
<211> LENGTH: 14
<212> TYPE: PRT
<213> ORGANISM: Epstein-Barr virus
```

<400> SEQUENCE: 36

Val Val Arg Met Phe Met Arg Glu Arg Gln Leu Pro Gln Ser
1               5                   10

<210> SEQ ID NO 37
<211> LENGTH: 9
<212> TYPE: PRT
<213> ORGANISM: Homo sapiens

<400> SEQUENCE: 37

Tyr Met Asp Gly Thr Met Ser Gln Val
1               5

<210> SEQ ID NO 38
<211> LENGTH: 4
<212> TYPE: PRT
<213> ORGANISM: Homo sapiens
<220> FEATURE:
<221> NAME/KEY: MISC_FEATURE
<222> LOCATION: (2)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa can be any hydrophobic amino acid

<400> SEQUENCE: 38

Tyr Xaa Xaa Xaa
1

<210> SEQ ID NO 39
<211> LENGTH: 4
<212> TYPE: PRT
<213> ORGANISM: Homo sapiens

<400> SEQUENCE: 39

Tyr Gln Arg Ile
1

<210> SEQ ID NO 40
<211> LENGTH: 28
<212> TYPE: PRT
<213> ORGANISM: Homo sapiens

<400> SEQUENCE: 40

Met Val Cys Phe Arg Leu Phe Pro Val Pro Gly Ser Gly Leu Val Leu
1               5                   10                  15

Val Cys Leu Val Leu Gly Ala Val Arg Ser Tyr Ala
            20                  25

<210> SEQ ID NO 41
<211> LENGTH: 29
<212> TYPE: PRT
<213> ORGANISM: Homo sapiens

<400> SEQUENCE: 41

Met Val Cys Phe Arg Leu Phe Pro Val Pro Gly Ser Gly Leu Val Leu
1               5                   10                  15

Val Cys Leu Val Leu Gly Ala Val Arg Ser Tyr Ala Leu
            20                  25

<210> SEQ ID NO 42
<211> LENGTH: 27
<212> TYPE: PRT

<213> ORGANISM: Homo sapiens

<400> SEQUENCE: 42

Met Pro Arg Gln Leu Ser Ala Ala Ala Leu Phe Ala Ser Leu Ala
1               5                   10                  15

Val Ile Leu His Asp Gly Ser Gln Met Arg Ala
            20                  25

<210> SEQ ID NO 43
<211> LENGTH: 28
<212> TYPE: PRT
<213> ORGANISM: Homo sapiens

<400> SEQUENCE: 43

Met Pro Arg Gln Leu Ser Ala Ala Ala Leu Phe Ala Ser Leu Ala
1               5                   10                  15

Val Ile Leu His Asp Gly Ser Gln Met Arg Ala Lys
            20                  25

<210> SEQ ID NO 44
<211> LENGTH: 21
<212> TYPE: PRT
<213> ORGANISM: Homo sapiens

<400> SEQUENCE: 44

Met Arg Leu Ala Val Leu Phe Ser Gly Ala Leu Leu Gly Leu Leu Ala
1               5                   10                  15

Ala Gln Gly Thr Gly
            20

<210> SEQ ID NO 45
<211> LENGTH: 22
<212> TYPE: PRT
<213> ORGANISM: Homo sapiens

<400> SEQUENCE: 45

Met Arg Leu Ala Val Leu Phe Ser Gly Ala Leu Leu Gly Leu Leu Ala
1               5                   10                  15

Ala Gln Gly Thr Gly Asn
            20

<210> SEQ ID NO 46
<211> LENGTH: 17
<212> TYPE: PRT
<213> ORGANISM: Homo sapiens

<400> SEQUENCE: 46

Met Leu Leu Leu Pro Phe Gln Leu Leu Ala Val Leu Phe Pro Gly Gly
1               5                   10                  15

Asn

<210> SEQ ID NO 47
<211> LENGTH: 18
<212> TYPE: PRT
<213> ORGANISM: Homo sapiens

<400> SEQUENCE: 47

Met Leu Leu Leu Pro Phe Gln Leu Leu Ala Val Leu Phe Pro Gly Gly
1               5                   10                  15

Asn Ser

<210> SEQ ID NO 48
<211> LENGTH: 23
<212> TYPE: PRT
<213> ORGANISM: Homo sapiens

<400> SEQUENCE: 48

Gln Glu Gln Gly His Pro Gln Thr Gly Cys Glu Cys Glu Asp Gly Pro
1               5                   10                  15

Asp Gly Gln Glu Met Asp Pro
            20

<210> SEQ ID NO 49
<211> LENGTH: 40
<212> TYPE: PRT
<213> ORGANISM: Homo sapiens

<400> SEQUENCE: 49

Glu Asp Glu Gly Ala Ser Ala Gly Gln Gly Pro Lys Pro Glu Ala Asp
1               5                   10                  15

Ser Gln Glu Gln Gly His Pro Gln Thr Gly Cys Glu Cys Glu Asp Gly
            20                  25                  30

Pro Asp Gly Gln Glu Met Asp Pro
        35                  40

<210> SEQ ID NO 50
<211> LENGTH: 13
<212> TYPE: PRT
<213> ORGANISM: Homo sapiens

<400> SEQUENCE: 50

Pro Glu Val Trp Ile Leu Ser Pro Leu Leu Arg His Gly
1               5                   10

<210> SEQ ID NO 51
<211> LENGTH: 28
<212> TYPE: PRT
<213> ORGANISM: Homo sapiens

<400> SEQUENCE: 51

Pro Ala Thr Arg Val Pro Glu Val Trp Ile Leu Ser Pro Leu Leu Arg
1               5                   10                  15

His Gly Gly Pro His Thr Gln Thr Gln Asn His Thr
            20                  25

<210> SEQ ID NO 52
<211> LENGTH: 46
<212> TYPE: PRT
<213> ORGANISM: Homo sapiens

<400> SEQUENCE: 52

Gln Glu Gly Glu Asp Glu Gly Ala Ser Ala Gly Gln Gly Pro Lys Pro
1               5                   10                  15

Glu Ala Asp Ser Gln Glu Gln Gly His Pro Gln Thr Gly Cys Glu Cys
            20                  25                  30

Glu Asp Gly Pro Asp Gly Gln Glu Met Asp Pro Pro Asn Pro
        35                  40                  45

<210> SEQ ID NO 53
<211> LENGTH: 34
<212> TYPE: PRT
<213> ORGANISM: Homo sapiens

<400> SEQUENCE: 53

```
Ser Cys Glu Pro Ala Thr Arg Val Pro Glu Val Trp Ile Leu Ser Pro
1               5                   10                  15

Leu Leu Arg His Gly Gly Pro His Thr Gln Thr Gln Asn His Thr Ala
                20                  25                  30

Ser Pro

<210> SEQ ID NO 54
<211> LENGTH: 42
<212> TYPE: PRT
<213> ORGANISM: Homo sapiens

<400> SEQUENCE: 54

Asp Pro Ser Ser Asp Tyr Thr Ile Val Leu Pro Val Ile Gly Ala Ile
1               5                   10                  15

Val Val Gly Leu Cys Leu Met Gly Met Gly Val Tyr Lys Ile Arg Leu
                20                  25                  30

Arg Cys Gln Ser Ser Gly Tyr Gln Arg Ile
            35                  40
```